US007354903B2

(12) United States Patent
Owen

(10) Patent No.: US 7,354,903 B2
(45) Date of Patent: **\*Apr. 8, 2008**

(54) COSMETIC COMPOSITIONS CONTAINING SHORT BIOACTIVE PEPTIDES

(75) Inventor: Donald R Owen, Kenner, LA (US)

(73) Assignee: Helix BioMedix, Inc., Bothell, WA (US)

( * ) Notice: Subject to any disclaimer, the term of this patent is extended or adjusted under 35 U.S.C. 154(b) by 258 days.

This patent is subject to a terminal disclaimer.

(21) Appl. No.: 10/839,525

(22) Filed: May 5, 2004

(65) Prior Publication Data

US 2004/0229808 A1    Nov. 18, 2004

Related U.S. Application Data

(63) Continuation of application No. 09/820,053, filed on Mar. 28, 2001, now Pat. No. 6,875,744.

(51) Int. Cl.
*A61K 38/00* (2006.01)

(52) U.S. Cl. .............................. 514/16; 514/12; 514/2; 514/16; 530/350; 530/300

(58) Field of Classification Search ..................... None
See application file for complete search history.

(56) References Cited

U.S. PATENT DOCUMENTS

| | | | |
|---|---|---|---|
| 4,355,104 A | 10/1982 | Hultmark et al. | |
| 4,520,016 A | 5/1985 | Hultmark et al. | |
| 5,561,107 A | 10/1996 | Jaynes et al. | |
| 5,620,954 A | 4/1997 | Maloy | |
| 5,717,064 A | 2/1998 | Julian et al. | |
| 5,744,445 A | 4/1998 | Jaynes et al. | |
| 5,789,542 A | 8/1998 | McLaughlin | 530/326 |
| 5,861,478 A * | 1/1999 | Jaynes | 530/324 |
| 5,962,410 A | 10/1999 | Jaynes et al. | |
| 6,001,805 A | 12/1999 | Jaynes et al. | |
| 6,084,156 A | 7/2000 | Garbabino | |
| 6,191,110 B1 | 2/2001 | Jaynes et al. | |
| 6,255,282 B1 | 7/2001 | Jaynes | |
| 6,303,568 B1 | 10/2001 | Haynes et al. | |
| 6,331,440 B1 | 12/2001 | Nordstedt et al. | |
| 6,348,445 B1 * | 2/2002 | Kari et al. | 514/12 |
| 6,440,935 B1 | 8/2002 | Jaynes et al. | |
| 6,559,281 B1 | 5/2003 | Jaynes | |
| 6,566,334 B1 | 5/2003 | McLaughlin | |
| 6,635,740 B1 | 10/2003 | Enright et al. | |
| 6,958,212 B1 * | 10/2005 | Hubbell et al. | 435/6 |

FOREIGN PATENT DOCUMENTS

| | | |
|---|---|---|
| EP | 1004595 A | 5/2000 |
| WO | WO 96/03519 A | 2/1996 |
| WO | WO 01/49834 | 7/2001 |

OTHER PUBLICATIONS

Galvin, et al; "Comparative tolerance of adapalene 0.1% gel and six different tretinoin formulations." Brit. Journ. Dermatology 139 (suppl 52) 1998:34-40.*

Seffernick et al., J. Bacteriology, vol. 183, pp. 2405-2410, 2001.*
Wells, Biochemistry, vol. 29, pp. 8509-8517, 1990.*
Baghian et al., "An Amphipathic α-Helical Synthetic Peptide Analogue of Melittin Inhibits Herpes Simples Virus-1 (HSV-1)-Induced Cell Fusion and Virus Spread," *Peptides*, 18(2):177-183 (1997).
Bessalle et al., "Structure-Function Studies of Amphiphilic Antibacterial Peptides," J. Med. Chem., 1993, 36:1203-1209.
Blondelle et al., "Lipid-Induced Conformation and Lipid-Binding Properties of Cytolytic and Antimicrobial Peptides: Determination and Biological Specificity," *Biochimica et Biophysica Acta*, 1462:89-108 (1999).
Dathe et al, "Structural Features of Helical Antimicrobial Peptides: Their Potential to Modulate Activity on Model Membranes and Biological Cells," *Biochimica et Biophysica Acta* 1462:71-87 (1999).
De Lucca et al., "Fungicidal Properties, Sterol Binding, and Proteolytic Resistance on the Synthetic Peptide D4E1," *Can. J. Microbiol*, 44:514-520 (1998).
Dushay et al., "Two attacin Antibacterial Genes of *Drosophila melanogaster*," *Gene*, 246:49-57 (2000).
Ekengren et al., Drosophila Cecropin as an Antifungal Agent, *Insect Biochemistry and Molecular Biology*, 29:965-972 (1999).
Epand et al., "Diversity of Antimicrobial Peptides and Their Mechanisms of Action," *Biochimica et Biophysica Acta* 1462:11-28 (1999).
Friedrich et al., "Salt-Resistant Alpha-Helical Cationic Antimicrobial Peptides," *Antimicrobial Agents and Chemotherapy*, pp. 1542-1548 (1999).
Giacometti et al., "Antimicrobial Activity of Polycationic Peptides," *Peptide*, 20:1265-1273 (1999).
Giacometti et al., "In-Vitro Activity of Cationic Peptides Alone and in Combination with Clinically Used Antimicrobial Agents Against *Pseudomonas aeruginosa*," *Journal of Antimicrobial Chemotherapy*, 44:641-645 (1999).
Goraya et al., "Peptides with Antimicrobial Activity from Four Different Families Isolated from the Skins of the North American Frogs *Rana luteiventris, Rana berlandieri* and *Rana pipiens*," *Eur. J. Biochem*, 267:894-900 (2000).
Hancock et al., "Cationic Peptides: A New Source of Antibiotics," *Tibtech*, 16:82-88 (1998).
Hancock et al., "Peptide Antibiotics," *Antimicrobial Agents and Chemotherapy*, pp. 1317-1323 (1999).
Hancock, "Host Defence (Cationic) Peptides. What is Their Future Clinical Potential?", *Drugs* 4:469-473 (1999).
Hancock, "Peptide Antibiotics," *Lancet*, 349:418-422 (1997).
Hong et al., Structure and Organization of Hemolytic and Nonhemolytic Diastereomers of Antimicrobial Peptides in Membranes, *Biochemistry*, 38:16963-16973 (1999).
Hung et al., "Membrane Lysis by the Antibacterial Peptides on Cecropins B1 and B3: A Spin-Label Electron Spin Resonance Study on Phospholipid Bilayers," *Biophysical Journal*, 77:3120-3233 (1999).

(Continued)

*Primary Examiner*—Hope Robinson
(74) *Attorney, Agent, or Firm*—Howrey LLP

(57) ABSTRACT

Short bioactive peptides containing phenylalanine, leucine, alanine, and lysine residues are disclosed. The peptides can be used in antibacterial, antifungal, anticancer, and other biological applications.

13 Claims, No Drawings

OTHER PUBLICATIONS

Jia et al., "Antimicrobial Peptides Protect Coho Salmon from *Vibrio anguillarum* Infections," *Applied and Environmental Microbiology*, 66(5):1928-1932 (2000).

Juvvadi et al., "Structure-Activity Studies of Normal and Retro Pig Cecropin-Melittin Hybrids," *J. Peptide Res.*, 53:244-251 (1999).

Kondejewski et al, "Dissociation of Antimicrobial and Hemolytic Activities in the Cyclic Peptide Diastereomers by Systematic Alterations in Amphipathicity," *The Journal of Biological Chemistry*, 274(19):13181-13192 (1999).

Lowenberger et al., Antimicrobial Activity Spectrum, cDNA Cloning, and mRNA Expression of a Newly Isolated Member of the Cecropin Family from the Mosquito Vector *Aedes aegypti*, *The Journal of Biological Chemistry*, 274(29):20092-20097 (1999).

Martin et al., "Evaluation of the Effect of Peptidyl Membrane-Interactive Molecules of Avian Coccidia," *Parasitol Res.*, 85:331-336 (1999).

McInnes et al., "Development of the Structural Basis for Antimicrobial and Hemolytic Activities of Peptides Based on Gramicidin S and Design of Novel Analogs Using NMR Spectroscopy," *The Journal of Biological Chemistry*, 275(19):14287-14294 (2000).

Oh et al., "Activities of Synthetic Hybrid Peptides Against Anaerobic Bacteria: Aspects of Methodology and Stability," *Antimicrobial Agents and Chemotherapy*, pp. 68-72 (2000).

Oh et al., "Cationic Peptide Antimicrobials Induce Selective Transcription of micF and osmY in *Escherichia coli*," *Biochimica et Biophysica Acta*, 1463:43-54 (2000).

Oh, J.E., et al., "Design, Synthesis and Characterization—(A Model Decapeptide)," J. Peptide Res., 1999, 54:129-136.

Osapay et la., "Formation and Characterization of a Single Trp-Trp Cross-Link in Indolicidin the Confers Protease Stability Without Altering Antimicrobial Activity," *The Journal of Biological Chemistry*, 275(16):12017-12022 (2000).

Reed et al., Interleukin 2 Promoter/Enhancer Controlled Expression of a Synthetic Cecropin-Class Lytic Peptide in Transgenic Mice and Subsequent Resistance to *Brucella abortus*, *Transgenic Research*, 6:337-347 (1997).

Robertson et al., "Peptidyl Membrane-Interactive Molecules are Cytotoxic to Prostatic Cancer Cells in vitro," *World J. Urol.*, 16:405-409 (1998).

Rocca et al., "Simulation Studies of the Interaction of Antimicrobial Peptides and Lipid Bilayers," *Biochimica et Biophysica Acta*, 1462:185-200 (1999).

Schwab et al., "In Vitro Activities of Designated Antimicrobial Peptides Against Multidrug-Resistant Cystic Fibrosis Pathogens," *Antimicrobial Agents and Chemotherapy*, pp. 1435-1440 (1999).

Scott et al., "Biological Properties of Structurally Related α-Helical Cationic Antimicrobial Peptides," *Infection and Immunity*, 67(4):2005-2009 (1999).

Scott et al., "Cutting Edge: Cationic Antimicrobial Peptides Block the Binding of Lipopolysaccharide (LPS) to LPS Binding Protein," *The Journal of Immunology*, pp. 549-533 (2000).

Shin et al., "Effects of the Hinge Region of Cecropin A(1-8)-Magainin 2(1-12), a Synthetic Antimicrobial Peptide, on Liposomes; Barterial and Tumor Cells," *Biochimica et Biophysica Acta*, 1463:209-218 (2000).

Shin et al., "Structure-Antibacterial, Antitumor and Hemolytic Activity Relationships of Cecropin A-magainin 2 and Cecropin A-Melittin Hybrid Peptides," *J. Peptide Res.*, 53:82-90 (1999).

Silvestro, et al. "Antibacterial and Antimembrane Activities of Cecropin A in *Escherichia coli*", *Antimicrobial Agents and Chemotherapy*, pp. 602-607 (2000).

Wang et al, "The Effect of pH on the Structure, Binding and Model Membrane Lysis by Cecropin B and Analogs," *Biochimica et Biophysica Acta* 1473:418-430 (1999).

Wu et al., "Improved Derivatives of Bactenecin, a Cyclic Dodecameric Antimicrobial Cationic Peptide," *Antimicrobial Agents and Chemotherapy*, pp. 1274-1276 (1999).

Wu et al., Mechanism of Interaction of Different Classes of Cationic Antimicrobial Peptides with Planar Bilayers and with the Cytoplasmic Membrane of *Escherichia coli*, 38:7235-7242 (1999).

Zboinska et al., Antibacterial activity of phosphono dipeptides based on 1-amino-1-methylethanephosphonic acid. FEMS Microbiology Letters. 1990, vol. 70, pp. 23-28, especially pp. 23 and 25-27.

Zhang et al, "Determinants of Recombinant Production of Antimicrobial Cationic Peptides and Creation of Peptide Variants in Bacteria," *Biochemical and Biophysical Research Communications*, 274:674-680 (1998).

Zhang et al., "Influence of Proline Residues on the Antibacterial and Synergistic Activities of α-Helical Peptides," *Biochemistry*, 38:8102-8111 (1999).

Supplementary European Search Report for EP 02 72 5386 dated Jul. 28, 2005.

Katayama, Lou et al., "A Pentapeptide from Type I Procollagen Promotes Extracellular Matrix Production," *The Journal of Biological Chemistry*, 268(14):9941-9944 (1993).

* cited by examiner

COSMETIC COMPOSITIONS CONTAINING SHORT BIOACTIVE PEPTIDES

CROSS REFERENCE TO RELATED APPLICATIONS

The present application is a continuation of U.S. patent application Ser. No. 09/820,053 filed Mar. 28, 2001, now U.S. Pat. No. 6,875,744, the contents of which are incorporated herein by reference.

FIELD OF THE INVENTION

The invention relates to short length peptides containing phenylalanine, leucine, alanine, and lysine amino acid residues (F, L, A, and K; "FLAK peptides") in their primary sequence. In particular, FLAK peptides having desirable antimicrobial, antifungal, anticancer, and other biological activities are disclosed.

BACKGROUND OF THE INVENTION

Various bioactive peptides have been reported in both the scientific literature and in issued patents. Peptides historically have been isolated from natural sources, and have recently been the subject of structure-function relationship studies. Additionally, natural peptides have served as starting points for the design of synthetic peptide analogs.

A review of peptide antibiotics was published by R. E. W. Hancock in 1997 (*Lancet* 349: 418-422). The structure, function, and clinical applications of various classes of peptides were discussed. An additional review of cationic peptide antibiotics was published in 1998 (Hancock, R. E. W. and Lehrer, R. *Trends Biotechnol.* 16: 82-88). The peptides are typically cationic amphipathic molecules of 12 to 45 amino acids in length. The peptides permeabilize cell membranes leading to the control of microbial agents. The clinical potential of host defense cationic peptides was discussed by R. E. W. Hancock in 1999 (*Drugs* 57(4): 469-473; *Antimicrobial Agents and Chemotherapy* 43(6): 1317-1323). The antibacterial, antifungal, antiviral, anticancer, and wound healing properties of the class of peptides are discussed.

Reviews of the structural features of helical antimicrobial peptides, and their presumed mechanisms of action have been published (see, for example, Dathe, M. and Wieprecht, T. *Biochimica et Biophysica Acta* 1462: 71-87 (1999); Epand, R. M. and Vogel H. J. *Biochimica et Biophysica Acta* 1462: 11-28 (1999)). Structural parameters believed to be capable of modulating activity and selectivity include helicity, hydrophobic moment, hydrophobicity, angle subtended by the hydrophilic/hydrophobic helix surfaces, and charge.

A wide array of naturally occurring alpha helical peptides have been reported. The following are representative of the many references in the field.

Cecropins are a family of α-helical peptides isolated from insects. Cecropins are known for their antibacterial properties, as described in U.S. Pat. Nos. 4,355,104 and 4,520,016. The cecropins were generally found to have activity against gram-negative bacteria, but not against all gram-negative bacteria. Cecropins were found not to have activity against eucaryotic cells (Andreu, et al., *Biochemistry* 24: 163-188 (1985); Boman, et al., *Developmental and Comparative Immunol.* 9: 551-558 (1985); Steiner et al., *Nature* 292: 246-248 (1981)). Cecropins from *Drosophila* and *Hyalphora* were presented as having activity against various strains of fungi (Ekengren, S. and Hultmark, D., *Insect Biochem. and Molec. Biol.* 29: 965-972 (1999)). Cecropin A from mosquito *Aedes aegypti* is reportedly different from most insect cecropins in that it lacks tryptophan and C-terminal amidation (Lowenberger, C. et al., *J. Biol. Chem.* 274(29): 20092-20097 (1999)).

Frogs from the genus *Rana* produce a wide array of antimicrobial peptides in their skin (Goraya, J. et al., *Eur. J. Biochem.* 267: 894-900 (2000)). Peptides as short as 13 amino acids were reported, and were grouped into structural families. The sequences showed little or no sequence identity to peptides isolated from frogs of other genera, such as the magainin and dermaseptin peptides.

U.S. Pat. No. 5,962,410 disclosed the inhibition of eucaryotic pathogens, and the stimulation of lymphocytes and fibroblasts with lytic peptides such as cecropins and sarcotoxins. Various peptides presented include Cecropin B, Cecropin SB-37, Cecropin A, Cecropin D, Shiva-1, Lepidopteran, Sarcotoxin 1A, Sarcotoxin 1B, and Sarcotoxin 1C.

Transgenic mice producing the Shiva-1 cecropin class lytic peptide were reported by Reed, W. A. et al., *Transgenic Res.* 6: 337-347 (1997). Infection of the transgenic mice with a *Brucella abortus* challenge resulted in a reduction of the number of bacteria relative to infection of non-transgenic mice.

Magainin is an α-helical 23 amino acid peptide isolated from the skin of the African frog *Xenopus laevis* (Zasloff, M. *Proc. Natl. Acad. Sci. U.S.A.* 84: 5449-5453 (1987).

Cathelin associated α-helical peptides of 23 to 38 amino acids are found in the blood cells of sheep, humans, cattle, pigs, mice, and rabbits (Zanetti, M. et al., *FEBS Lett.* 374: 1-5 (1995)).

The antimicrobial activities of buforin II, cecropin P1, indolicidin, magainin II, nisin, and ranalexin were reported by Giacomette, A. et al. (*Peptides* 20: 1265-1273 (1999)). The peptides showed variable activities against bacteria and yeast.

Various synthetic peptides have been prepared and assayed both in vitro and in vivo.

U.S. Pat. No. 5,861,478 disclosed synthetic lytic peptides of about 20 to 40 amino acids which adopt an α-helical conformation. The peptides are effective in the treatment of microbial infections, wounds, and cancer. The peptides disclosed include cecropin B, SB-37*, LSB-37, SB-37, Shiva 1 and 10-12, β-fibrin signal peptide, Manitou 1-2, Hecate 1-3, Anubis 1-5 and 8, and Vishnu 1-3 and 8.

Hecate was described as a synthetic peptide analog of melittin by Baghian, A. et al. (*Peptides* 18(2): 177-183 (1997)). The peptides differ in their charge distribution, but not in their amphipathic alpha helical conformation. Hecate inhibited herpes simplex virus (HSV-1) while not adversely affecting cell growth and protein synthesis.

Synthetic peptides D2A21, D4E1, D2A22, D5C, D5C1, D4E, and D4B were described in Schwab, U. et al., *Antimicrob. Agents and Chemotherapy* 43(6): 1435-1440 (1999). Activities against various bacterial strains were presented.

Hybrid peptides made of cecropin and melittin peptides were reportedly prepared and assayed by Juvvadi, P. et al. (*J. Peptide Res.* 53: 244-251 (1999)). Hybrids were synthesized to investigate the effects of sequence, amide bond direction (helix dipole), charge, amphipathicity, and hydrophobicity on channel forming ability and on antibacterial activity. Sequence and amide bond direction were suggested to be important structural requirements for the activity of the hybrids.

A 26 amino acid insect cecropin—bee melittin hybrid, and analogs thereof, were described in a study of salt resistance (Friedrich, C. et al., *Antimicrobial Agents and Chemotherapy* 43(7): 1542-1548 (1999)). A tryptophan residue in the second position was found to be critical for activity. Modest changes in sequence were found to lead to substantial changes in the properties of the peptides.

The effects of proline residues on the antibacterial properties of α-helical peptides has been published (Zhang, L. et al., *Biochem.* 38: 8102-8111 (1999)). The addition of prolines was reported to change the membrane insertion properties, and the replacement of a single proline may change an antimicrobial peptide into a toxin.

A series of peptides having between 18 and 30 amino acids were prepared in order to test the effects of changes in sequence and charge on antibacterial properties (Scott, M. G., et al., *Infect. Immun.* 67(4): 2005-2009 (1999)). No significant correlation was found between length, charge, or hydrophobicity and the antimicrobial activity of the peptides. A general trend was found that shorter peptides were less active than longer peptides, although the authors expressed that this effect would probably be sequence dependent.

"Modellins", a group of synthetic peptides were prepared and assayed to compare sequence and structure relationships (Bessalle, R. et al. *J. Med. Chem.* 36: 1203-1209 (1993)). Peptides of 16 and 17 amino acids having hydrophobic and hydrophilic opposite faces were highly hemolytic and antibacterial. Smaller peptides tended to have lower biological activities.

A cecropin-melittin hybrid peptide and an amidated flounder peptide were found to protect salmon from *Vibrio anguillarum* infections in vivo (Jia, X. et al., *Appl. Environ. Microbiol.* 66(5): 1928-1932 (2000)). Osmotic pumps were used to deliver a continuous dose of either peptide to the fish.

Amphipathic peptides have been reported as being capable of enhancing wound healing and stimulating fibroblast and keratinocyte growth in vivo (U.S. Pat. Nos. 6,001,805 and 5,561,107). Transgenic plants have been reportedly prepared expressing lytic peptides as a fusion protein with ubiquitin (U.S. Pat. No. 6,084,156). Methylated lysine rich lytic peptides were reportedly prepared, displaying improved proteolytic resistance (U.S. Pat. No. 5,717,064).

While a number of natural and synthetic peptides exist, there exists a need for improved bioactive peptides and methods for their use.

SUMMARY OF THE INVENTION

Short (i.e. no more than 23 amino acids in length) peptides containing phenylalanine, leucine, alanine, and lysine amino acid residues in their primary sequence are disclosed. The peptides display desirable antibacterial, antifungal, anticancer biological activities, and also cause stimulation and proliferation of human fibroblasts and lymphocytes.

DESCRIPTION OF THE SEQUENCE LISTINGS

The following sequence listings form part of the present specification and are included to further demonstrate certain aspects of the present invention. The invention may be better understood by reference to one or more of these sequences in combination with the detailed description of specific embodiments presented herein.

TABLE 1

| SEQ ID NO: | Name | P-No. | Primary sequence |
|---|---|---|---|
| 1 | Hecate AC #1010 | 1 | FALALKALKKALKKLKKALKKAL-COOH |
| 2 | Hecate AM | 2 | FALALKALKKALKKLKKALKKAL-NH2 |
| 3 | SB-37 AC #1018 | 5 | MPKWKVFKKIEKVGRNIRNGIVKAGPAIAVLGEAKALG-COOH |
| 4 | Shiva 10 AM | 11 | FAKKLAKKLKKLAKKLAKLALAL-NH2 |
| 5 | SB-37 AM | 12 | MPKWKVFKKIEKVGRNIRNGIVIKAGPAIAVLGEAKALG-NH2 |
| 6 | Shiva 10 AC #1015 | 13 | FAKKLAKKLKKLAKKLAKLALAL-COOH |
| 7 | Magainin 2 | 16 | GIGKFLHSAKKFGKAFVGGIMNS-NH2 |
| 8 | FLAK01 AM | 23 | FALAAKALKKLAKKLKKLAKKAL-NH2 |
| 9 | FLAK03 AM | 24 | FALALKALKKLLKKLKKLAKKAL-NH2 |
| 10 | FLAK04 AM | 25 | FALALKALKKLAKKLKKLAKKAL-NH2 |
| 11 | FLAK05 AM | 26 | FALAKLAKKAKAKLKKALKAL-NH2 |
| 12 | FLAK06 AM | 27 | FALALKALKKLKKALKKAL-NH2 |
| 13 | FLAK06 AC | 27B | FALALKALKKLKKALKKAL-COOH |
| 14 | FLAK06 R-AC | 27C | FAKKLAKKLKKLAKLALAL-COOH |
| 15 | KAL V | 30 | VALALKALKKALKKLKKALKKAL-NH2 |
| 16 | FLAK 17 AM | 34 | FALALKKALKALKKAL-NH2 |

TABLE 1-continued

| SEQ ID NO: | Name | P-No. | Primary sequence |
|---|---|---|---|
| 17 | FLAK 26 AM | 35 | FAKKLAKLAKKLAKLAL-NH2 |
| 18 | FLAK 25 AM | 36 | FAKKLAKLAKKLAKLALAL-NH2 |
| 19 | Hecate 2DAc | 37 | FALALKALKKAL-(D)-K-(D)-KLKKALKKAL-COOH |
| 20 | FLAK43 AM | 38 | FAKKLAKLAKKLLAL-NH2 |
| 21 | FLAK44 AM | 39 | FAKKLAKLAKKALAL-NH2 |
| 22 | FLAK62 AM | 40 | FALAKKALKKAKKAL-NH2 |
| 23 | FLAK 06R-AM | 41 | FAKKLAKKLKKLAKLALAK-NH2 |
| 24 | MSI-78 AM | 42 | GIGKFLKKAKKFGKAFVKILKK-NH2 |
| 25 | FLAK50 | 43 | FAKLLAKLAKKLL-NH2 |
| 26 | FLAK51 | 44 | FAKKLAKLALKLAKL-NH2 |
| 27 | FLAK57 | 45 | FAKKLAKKLAKLAL-NH2 |
| 28 | FLAK71 | 46 | FAKKLKKLAKLAKKL-NH2 |
| 29 | FLAK77 | 47 | FAKKALKALKKL-NH2 |
| 30 | FLAK50V | 48 | VAKLLAKLAKKLL-NH2 |
| 31 | FLAK50F | 49 | FAKLLAKLAKKL-NH2 |
| 32 | FLAK26V AM | 50 | VAKKLAKLAKKLAKLAL-NH2 |
| 33 | CAME-15 | 53 | KWKLFKKIGAVLKVL-NH2 |
| 34 | FLAK50C | 54 | FAKLLAKLAKKAL-NH2 |
| 35 | FLAK50D | 55 | FAKLLAKALKKLL-NH2 |
| 36 | FLAK50E | 56 | FAKLLKLAAKKLL-NH2 |
| 37 | FLAK80 | 57 | FAKLLAKKLL-NH2 |
| 38 | FLAK81 | 58 | FAKKLAKALL-NH2 |
| 39 | FLAK82 | 59 | FAKKLAKKLL-NH2 |
| 40 | FLAK83M | 60 | FAKLAKKLL-NH2 |
| 41 | FLAK 26 Ac | 61 | FAKKLAKLAKKLAKLAL-COOH |
| 42 | Indolicidin | 63 | ILPWKWPWWPWRR-NH2 |
| 43 | FLAK 17C | 64 | FAKALKALLKALKAL-NH2 |
| 44 | FLAK 50H | 65 | FAKLLAKLAKAKL-NH2 |
| 45 | FLAK 50G | 66 | FAKLLAKLAKLKL-NH2 |
| 46 | Shiva Deny P69 + KWKL | 70 | FAKKLAKKLKKLAKKLAKKWKL-NH2 |
| 47 | Shiva 10 (1-18 AC) | 71 | FAKKLAKKLKKLAKKLAK-COOH |
| 48 | Shiva 10 peptide 71 + KWKL | 72 | FAKKLAKKLKKLAKKLAKKWKL-COOH |
| 49 | CA(1-7)Shiva 10 (1-16) | 73 | KWKLFKKKTKLFKKFAKKLAKKL-NH2 |
| 50 | FLAK 54 | 74 | FAKKLAKKLAKAL-NH2 |
| 51 | FLAK 56 | 75 | FAKKLAKKLAKLL-NH2 |
| 52 | FLAK 58 | 76 | FAKKLAKKLAKAAL-NH2 |
| 53 | FLAK 72 | 77 | FAKKLAKKAKLAKKL-NH2 |

TABLE 1-continued

| SEQ ID NO: | Name | P-No. | Primary sequence |
|---|---|---|---|
| 54 | FLAK 75 | 79 | FAKKLKKLAKKL-NH2 |
| 55 | Shiva 10 (1-16) Ac | 80 | KTKLFKKFAKKLAKKLKKLAKKL-COOH |
| 56 | CA(1-7)Shiva10 (1-16)-COOH | 81 | KWKLFKKKTKLFKKFAKKLAKKL-COOH |
| 57 | Indolocidin-ac | 91 | ILPWKWPWWPWRR-COOH |
| 58 | FLAK50B | 92 | FAKALAKLAKKLL-NH2 |
| 59 | FLAK50J | 93 | FAKLLAKLAKKAA-NH2 |
| 60 | FLAK50I | 94 | FAKLLALALKLKL-NH2 |
| 61 | FLAK50K | 95 | FAKLLAKLAKAKA-NH2 |
| 62 | FLAK50L | 96 | FAKLLAKLAKAKG-NH2 |
| 63 | Shiva-11 | 98 | FAKKLAKKLKKLAKKLAKLALALKALALKAL-NH2 |
| 64 | Shiva 11 [(1-16)ME(2-9)-COOH | 99 | FAKKLAKKLKKLAKKLIGAVLKV-COOH |
| 65 | FLAK 50N | 101 | FAKLLAKALKLKL-NH2 |
| 66 | FLAK 50O | 102 | FAKLLAKALKKAL-NH2 |
| 67 | FLAK 50P | 103 | FAKLLAKALKKL-NH2 |
| 68 | CA(1-&Hecate(11/23) | 104 | KWKLFKKALKKLKKALKKAL-NH2 |
| 69 | PYL-ME | 105 | KIAKVALAKLGIGAVLKVLTTGL-NH2 |
| 70 | FLAG26-D1 | 106 | FAKKLAKLAKKL-NH2 |
| 71 | Vishnu3 | 107 | MPKEKVFLKIEKMGRNIRN-NH2 |
| 72 | Melittin | 108 | GIGAVLKVLTTGLPALISWIKRKRQQ-NH2 |
| 73 | FLAK26-D2 | 109 | FAKKLAKLAKKLAKAL-NH2 |
| 74 | FLAG26-D3 | 110 | FAKKLLAKALKL-NH2 |
| 75 | FLAK50 Q1 | 111 | FAKFLAKFLKKAL-NH2 |
| 76 | FLAK50 Q2 | 112 | FAKLLFKALKKAL-NH2 |
| 77 | FLAK50 Q3 | 113 | FAKLLAKFLKKAL-NH2 |
| 78 | FLAK50 Q4 | 114 | FAKLLAKAFKKAL-NH2 |
| 79 | FLAK50 Q5 | 117 | FAKLFAKAFKKAL-NH2 |
| 80 | FLAK50 Q6 | 118 | FAKLLAKALKKFL-NH2 |
| 81 | FLAK50 Q7 | 119 | FAKLLAKALKKFAL-NH2 |
| 82 | FLAK50 Q8 | 120 | FAKLLAKLAKKFAL-NH2 |
| 83 | FLAK50 Q9 | 121 | FAKLFAKLAKKFAL-NH2 |
| 84 | FLAK50 Q10 | 122 | FKLAFKLAKKAFL-NH2 |
| 85 | FLAK50 T1 | 123 | FAKLLAKLAK-NH2 |
| 86 | FLAK50 T2 | 124 | FAKLLAKLAKKVL-NH2 |
| 87 | FLAK50 T3 | 125 | FAKLLAKLAKKIL-NH2 |
| 88 | FLAK50 T4 | 126 | FAKLLAKLAKKEL-NH2 |
| 89 | FLAK50 T5 | 127 | FAKLLAKLAKKSL-NH2 |

TABLE 1-continued

| SEQ ID NO: | Name | P-No. | Primary sequence |
|---|---|---|---|
| 90 | FLAK90 | 128 | FAKLA-NH2 |
| 91 | FLAK91 | 129 | FAKLF-NH2 |
| 92 | FLAK92 | 130 | KAKLF-NH2 |
| 93 | FLAK93 | 131 | KWKLF-NH2 |
| 94 | FLAK50 Z1 | 132 | FGKGIGKVGKKLL-NH2 |
| 95 | FLAK50 Z2 | 133 | FAFGKGIGKVGKKLL-NH2 |
| 96 | FLAK50 Z3 | 134 | FAKAIAKIAFGKGIGKVGKKLL-NH2 |
| 97 | FLAK50 Z4 | 135 | FAKLWAKLAFGKGIGKVGKKLL-NH2 |
| 98 | FLAK50 Z5 | 136 | FAKLWAKLAKKL-NH2 |
| 99 | FLAK50 Z6 | 137 | FAKGVGKVGKKAL-NH2 |
| 100 | FLAK50 Z7 | 138 | FAFGKGIGKIGKKGL-NH2 |
| 101 | FLAK50 Z8 | 139 | FAKIIAKIAKIAKKIL-NH2 |
| 102 | FLAK50 Z9 | 140 | FAFAKIIAKIAKKII-NH2 |
| 103 | FLAK94 | 141 | FALALKA-NH2 |
| 104 | FLAK93B | 142 | KWKLAKKALALL-NH2 |
| 105 | FLAK50 Z10 | 143 | FAKIIAKIAKKI-NH2 |
| 106 | FLAK96 | 144 | FALALKALKKAL-NH2 |
| 107 | FLAK97 | 145 | FALKALKK-NH2 |
| 108 | FLAK98 | 146 | KYKKALKKLAKLL-NH2 |
| 109 | FKRLA | 147 | FKRLAKIKVLRLAKIKR-NH2 |
| 110 | FLAK91B | 148 | FAKLAKKALAKLL-NH2 |
| 111 | FLAK92B | 149 | KAKLAKKALAKLL-NH2 |
| 112 | FLAK99 | 150 | KLALKLALKALKAAKLA-NH2 |
| 113 | FLAK50T6 | 151 | FAKLLAKLAKK-NH2 |
| 114 | FLAK50T7 | 152 | FAKLLAKLAKKGL-NH2 |
| 115 | FLAK95 | 153 | FALKALKKLKKALKKAL-NH2 |
| 116 | FLAK50T8 | 154 | VAKLLAKLAKKVL-NH2 |
| 117 | FLAK50T9 | 155 | YAKLLAKLAKKAL-NH2 |
| 118 | FLAK100-CO2H | 156 | KLLKLLLKLYKKLLKLL-COOH |
| 119 | FAGVL | 157 | FAVGLRAIKRALKKLRRGVRKVAKDL-NH2 |
| 120 | Modelin-5 | 159 | KLAKKLAKLAKLAKAL-NH2 |
| 121 | Modelin-5-CO2H | 160 | KLAKKLAKLAKLAKAL-COOH |
| 122 | Modelin-8 | 161 | KWKKLAKKW-NH2 |
| 123 | Modelin-8-CO2H | 162 | KWKKLAKKW-COOH |
| 124 | Modelin-1 | 163 | KLWKKWAKKWLKLWKAW-NH2 |
| 125 | Modelin-1-CO2H | 164 | KLWKKWAKKWLKLWKA-COOH |
| 126 | FLAK120 | 165 | FALALKALKKL-NH2 |
| 127 | FLAK121 | 166 | FALAKALKKAL-NH2 |

TABLE 1-continued

| SEQ ID NO: | Name | P-No. | Primary sequence |
|---|---|---|---|
| 128 | FLAK96B | 167 | FALALKLAKKAL-NH2 |
| 129 | FLAK96G | 168 | FALLKL-NH2 |
| 130 | FLAK96F | 169 | FALALKALKK-NH2 |
| 131 | FLAK96C | 170 | FALKALKKAL-NH2 |
| 132 | FLAK96D | 171 | FALLKALKKAL-NH2 |
| 133 | Modelin-8B | 172 | KWKK-NH2 |
| 134 | Modelin-8C | 173 | KWKKL-NH2 |
| 135 | Modelin-8D | 174 | KFKKLAKKF-NH2 |
| 136 | Modelin-8E | 175 | KFKKLAKKW-NH2 |
| 137 | Flak 96 | 176 | FALALKALKKA-NH2 |
| 138 | Flak 96I | 177 | FALLKALLKKAL-NH2 |
| 139 | Flak 96J | 178 | FALALKLAKKL-NH2 |
| 140 | Flak 96L | 179 | LKKLAKLALAF-NH2 |
| 141 | FLAK-120G | 180 | VALALKALKKL-NH2 |
| 142 | FLAK-120D | 181 | FALALKLKKL-NH2 |
| 143 | FLAK-120C | 182 | FALALKAKKL-NH2 |
| 144 | FLAK-120B | 183 | FALA-NH2 |
| 145 | FLAK-120F | 184 | WALAL-NH2 |
| 146 | Magainin2wisc | 300 | GIGKFLHAAKKFAKAFVAEIMNS-NH2 |
| 147 | D2A21 | 301 | FAKKFAKKFKKFAKKFAKFAFAF-NH2 |
| 148 | KSL-1 | 302 | KKVVFKVKFK-NH2 |
| 149 | KSL-7 | 303 | FKVKFKVKVK-NH2 |
| 150 | LSB-37 | 306 | LPKWKVFKKIEKVGRNIRNGIVKAGPAIAVLGEAKALG-NH2 |
| 151 | Anubis-2 | 307 | FAKKLAKKLKKLAKKLAKLAKKL-NH2 |
| 152 | FLAK17CV | 501 | VAKALKALLKALKAL-NH2 |
| 153 | FLAK50Q1V | 502 | VAKFLAKFLKKAL-NH2 |
| 154 | D2A21V | 503 | VAKKFAKKFKKFAKKFAKFAFAF-NH2 |
| 155 | FLAK25AMV | 504 | VAKKLAKLAKKLAKLALAL-NH2 |
| 156 | FLAK43AMV | 505 | VAKKLAKLAKKLLAL-NH2 |
| 157 | FLAK50DV | 506 | VAKLLAKALKKLL-NH2 |
| 158 | HECATE AMV | 507 | VALALKALKKALKKLKKALKKAL-NH2 |
| 159 | HECATE ACV | 508 | VALALKALKKALKKLKKALKKAL-COOH |
| 160 | FLAK04AMV | 509 | VALALKALKKLAKKLKKLAKKAL-NH2 |
| 161 | FLAK03AMV | 510 | VALALKALKKLLKKLKKLAKKAL-NH2 |
| 162 | D-Shiva 10 AC | 67 | (D)-FAKKLAKKLKKLAKKLAKLALAL-COOH |
| 163 | Shiva 11 AC | 100 | FAKKLAKKLKKLAKKLAKLALALKALALKA-COOH |

TABLE 1-continued

| SEQ ID NO: | Name | P-No. | Primary sequence |
|---|---|---|---|
| 164 | Shiva 10 (1-18)AM | 69 | FAKKLAKKLKKLAKKLAK-NH2 |
| 165 | FLAK 50M | 97 | FAKLLALALKKAL-NH2 |

DETAILED DESCRIPTION OF THE INVENTION

The invention is generally directed towards peptides having desirable biological properties, and their use. It is surprising that the peptides are efficacious due to their short length as compared to other peptides described in the art.

Peptides

One embodiment of the invention is directed towards an isolated peptide comprising phenylalanine, leucine, alanine, and lysine residues, wherein the peptide is about 5 to about 23 amino acids in length. The peptide can have a minimum length of about 5, 6, 7, 8, 9, 10, 11, 12, 13, 14, 15, 16, 17, or about 18 amino acids. The peptide can have a maximum length of about 5, 6, 7, 8, 9, 10, 11, 12, 13, 14, 15, 16, 17, 18, 19, 20, 21, 22, or about 23 amino acids. The peptide can be about 5 to about 20 amino acids in length. The peptide can consist essentially of, or consist of phenylalanine, leucine, alanine, and lysine residues. The peptide can have a percent amino acid composition of phenylalanine, leucine, alanine, and lysine residues of at least about 50%, 55%, 60%, 65%, 70%, 75%, 80%, 85%, 90%, 95%, 96%, 97%, 98%, 99%, or 100%. The peptide can generally be any of the listed SEQ ID NOS which fall within these various guidelines, and more preferably is SEQ ID NO:1, SEQ ID NO:2, SEQ ID NO:4, SEQ ID NO:5, SEQ ID NO:6, SEQ ID NO:8, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:23, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:34, SEQ ID NO:35, SEQ ID NO:36, SEQ ID NO:41, SEQ ID NO:43, SEQ ID NO:45, SEQ ID NO:46, SEQ ID NO:50, SEQ ID NO:51, SEQ ID NO:52, SEQ ID NO:55, SEQ ID NO:56, SEQ ID NO:57, SEQ ID NO:58, SEQ ID NO:59, SEQ ID NO:60, SEQ ID NO:61, SEQ ID NO:65, SEQ ID NO:66, SEQ ID NO:67, SEQ ID NO:68, SEQ ID NO:71, SEQ ID NO:74, SEQ ID NO:75, SEQ ID NO:77, SEQ ID NO:80, SEQ ID NO:81, SEQ ID NO:84, SEQ ID NO:85, SEQ ID NO:86, SEQ ID NO:87, SEQ ID NO:90, SEQ ID NO:91, SEQ ID NO:92, SEQ ID NO:93, SEQ ID NO:106, SEQ ID NO:108, SEQ ID NO:112, SEQ ID NO:115, SEQ ID NO:116, SEQ ID NO:126, SEQ ID NO:127, SEQ ID NO:128, SEQ ID NO:129, SEQ ID NO:131, SEQ ID NO:132, SEQ ID NO:137, SEQ ID NO:138, SEQ ID NO:139, SEQ ID NO:140, SEQ ID NO:141, SEQ ID NO:142, SEQ ID NO:143, SEQ ID NO:144, SEQ ID NO:145, SEQ ID NO:152, SEQ ID NO:159, SEQ ID NO:162, SEQ ID NO:163, SEQ ID NO:164, and SEQ ID NO:165. The peptide is preferably not hecate-1, anubis-1, anubis-2, anubis-5, anubis-8, vishnu-1, vishnu-2, vishnu-3, vishnu-8, or shiva-10.

The peptide can be similar to any of the above described peptides, and preferably is similar to SEQ ID NO:2 (or SEQ ID NO:16 or SEQ ID NO:126), SEQ ID NO:4 (or SEQ ID NO:14 or SEQ ID NO:17), SEQ ID NO:25, SEQ ID NO:43, SEQ ID NO:75, SEQ ID NO:84, SEQ ID NO:115, or SEQ ID NO:132 as determined by percent identity. The percent identity between the peptides is preferably at least about 70%, 75%, 80%, 85%, 90%, 95%, 96%, 97%, 98%, 99%, or 100%. Percent identity is determined using a sequence alignment by the commercial product CLUSTALW. The number of aligned amino acids are divided by the length of the shorter peptide, and the result is multiplied by 100% to determine percent identity. If the length of the shorter peptide is less than 10 amino acids, the number of aligned amino acids are divided by 10, and the result is multiplied by 100% to determine percent identity.

The peptides can comprise D- or L-amino acids. The peptides can comprise all D-amino acids. The peptides can have an acid C-terminus (—$CO_2H$) or an amide C-terminus (—$CONH_2$, —CONHR, or —$CONR_2$).

Methods of Use

An additional embodiment of the invention is directed towards methods of using the above described peptides. The methods of use preferably do not cause injury or kill normal uninfected mammalian cells. The methods of use at therapeutic dose levels preferably do not cause injury to or kill normal uninfected or non-neoplastic mammalian cells. The methods of use may involve the use of a single peptide, or may involve the use of multiple peptides.

An embodiment of the invention is the use of the above described peptides to inhibit or kill microbial cells (microorganisms). The microorganisms may be bacterial cells, fungal cells, protozoa, viruses, or eucaryotic cells infected with pathogenic microorganisms. The method generally is directed towards the contacting of microorganisms with the peptide. The contacting step can be performed in vivo, in vitro, topically, orally, transdermally, systemically, or by any other method known to those of skill in the art. The contacting step is preferably performed at a concentration sufficient to inhibit or kill the microorganisms. The concentration of the peptide can be at least about 0.1 µM, at least about 0.5 µM, at least about 1 µM, at least about 10 µM, at least about 20 µM, at least about 50 µM, or at least about 100 µM. The methods of use can be directed towards the inhibition or killing of microorganisms such as bacteria, gram positive bacteria, gram negative bacteria, mycobacteria, yeast, fungus, algae, protozoa, viruses, and intracellular organisms. Specific examples include, but are not limited to, Staphylococcus, Staphylococcus aureus, Pseudomonas, Pseudomonas aeruginosa, Escherichia coli, Chlamydia, Candida albicans, Saccharomyces, Saccharomyces cerevisiae, Schizosaccharomyces pombe, Trypanosoma cruzi, or Plasmodium falciparum. The contacting step can be performed by systemic injection, oral, subcutaneous, IP, IM, IV injection, or by topical application. For injection, the dosage can be between any of the following concentrations: about 1 mg/kg, about 5 mg/kg, about 10 mg/kg, about 25 mg/kg, about 50 mg/kg, about 75 mg/kg, and about 100 mg/kg. The contacting step can be performed on a mammal, a cat, a dog, a cow, a horse, a pig, a bird, a chicken, a plant, a fish, or a human.

Preferred peptides for antibacterial applications include SEQ ID NO:1, SEQ ID NO:2, SEQ ID NO:4, SEQ ID NO:6, SEQ ID NO:8, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:23, SEQ ID NO:25, SEQ ID NO:26, SEQ ID NO:27, SEQ ID NO:28, SEQ ID NO:30, SEQ ID NO:31, SEQ ID NO:32, SEQ ID NO:34, SEQ ID NO:35, SEQ ID NO:36, SEQ ID NO:41, SEQ ID NO:43, SEQ ID NO:45, SEQ ID NO:46, SEQ ID NO:50, SEQ ID NO:51, SEQ ID NO:52, SEQ ID NO:55, SEQ ID NO:56, SEQ ID NO:57, SEQ ID NO:58, SEQ ID NO:60, SEQ ID NO:65, SEQ ID NO:66, SEQ ID NO:67, SEQ ID NO:68, SEQ ID NO:74, SEQ ID NO:75, SEQ ID NO:77, SEQ ID NO:80, SEQ ID NO:81, SEQ ID NO:84, SEQ ID NO:86, SEQ ID NO:87, SEQ ID NO:93, SEQ ID NO:106, SEQ ID NO:108, SEQ ID NO:112, SEQ ID NO:115, SEQ ID NO:126, SEQ ID NO:128, SEQ ID NO:162, SEQ ID NO:163, SEQ ID NO:164, and SEQ ID NO:165.

Preferred peptides for antifungal applications include SEQ ID NO:2, SEQ ID NO:10, SEQ ID NO:11, SEQ ID NO:12, SEQ ID NO:13, SEQ ID NO:16, SEQ ID NO:17, SEQ ID NO:25, SEQ ID NO:30, SEQ ID NO:35, SEQ ID NO:58, SEQ ID NO:66, SEQ ID NO:67, SEQ ID NO:80, SEQ ID NO:81, SEQ ID NO:84, SEQ ID NO:85, SEQ ID NO:86, SEQ ID NO:106, SEQ ID NO:108, SEQ ID NO:115, SEQ ID NO:116, SEQ ID NO:126, SEQ ID NO:128, SEQ ID NO:131, SEQ ID NO:143, SEQ ID NO:163, and SEQ ID NO:165.

An additional embodiment of the invention is the use of any of the above described peptides to inhibit or kill cancer cells. The method generally is directed towards the contacting of cancer cells with the peptide. The contacting step can be performed in vivo, in vitro, topically, orally, transdermally, systemically, or by any other method known to those of skill in the art. The contacting step is preferably performed at a concentration sufficient to inhibit or kill the cancer cells. The concentration of the peptide can be at least about at least about 0.1 µM, at least about 0.5 µM, at least about 1 µM, at least about 10 µM, at least about 20 µM, at least about 50 µM, or at least about 100 µM. The cancer cells can generally be any type of cancer cells. The cancer cells can be sarcomas, lymphomas, carcinomas, leukemias, breast cancer cells, colon cancer cells, skin cancer cells, ovarian cancer cells, cervical cancer cells, testicular cancer cells, lung cancer cells, prostate cancer cells, and skin cancer cells. The contacting step can be performed by subcutaneous, IP injection, IM injection, IV injection, direct tumor injection, or topical application. For injection, the dosage can be between any of the following concentrations: about 0.1 mg/kg, about 1 mg/kg, about 5 mg/kg, about 10 mg/kg, about 25 mg/kg, about 50 mg/kg, about 75 mg/kg, and about 100 mg/kg. The contacting step can be performed on a mammal, a cat, a dog, a cow, a horse, a pig, a bird, a chicken, a plant, a fish, a goat, a sheep, or a human. The inhibition of cancer cells can generally be any inhibition of growth of the cancer cells as compared to the cancer cells without peptide treatment. The inhibition is preferably at least about 10%, 20%, 30%, 40%, 50%, 60%, 70%, 80%, 90%, 95%, 96%, 97%, 98%, 99%, and ideally 100% inhibition of growth. The inhibition may be achieved by lysis of the cancer cells or by other means. The cancer inhibiting peptide can be used synergistically with other cancer chemotherapeutic agents.

Preferred peptides for anticancer applications include SEQ ID NO:1, SEQ ID NO:2, SEQ ID NO:8, SEQ ID NO:11, SEQ ID NO:13, SEQ ID NO:16, SEQ ID NO:17, SEQ ID NO:18, SEQ ID NO:19, SEQ ID NO:20, SEQ ID NO:25, SEQ ID NO:26, SEQ ID NO:29, SEQ ID NO:30, SEQ ID NO:32, SEQ ID NO:35, SEQ ID NO:46, SEQ ID NO:51, SEQ ID NO:56, SEQ ID NO:57, SEQ ID NO:58, SEQ ID NO:60, SEQ ID NO:68, SEQ ID NO:75, SEQ ID NO:86, SEQ ID NO:152, and SEQ ID NO:162

An additional embodiment of the invention is directed towards a method for promoting the stimulation and/or proliferation of cells. The method can comprise contacting the cells and a composition, wherein the composition comprises a peptide. The peptide can be any of the above described peptides. The concentration of the peptide in the composition can be about 0.01 µM to about 500 µM, about 0.1 µM to about 100 µM, about 1 µM to about 50 µM, or about 1 µM to about 10 µM. The cells can generally be any type of cells, and preferably are mammalian cells, specifically including, but not limited to fibroblast and leukocyte cells, including lymphocyte and phagocytic cells. The metabolic stimulation and/or proliferation of the cells is preferably increased by at least about 10%, 20%, 30%, 40%, 50%, 60%, 70%, 80%, 90%, 100%, 125%, 150%, 175%, or 200% relative to the same cells not contacted with the composition. The composition can further comprise a growth factor. The stimulatory and proliferative properties of some of the FLAK peptides hold promise for their application in skin care, wound healing, and in immunomodulation of compromised mammalian immune systems.

Preferred peptides for stimulation and proliferation applications include SEQ ID NO:1, SEQ ID NO:2, SEQ ID NO:5, SEQ ID NO:6, SEQ ID NO:8, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:20, SEQ ID NO:27, SEQ ID NO:28, SEQ ID NO:30, SEQ ID NO:32, SEQ ID NO:34, SEQ ID NO:45, SEQ ID NO:46, SEQ ID NO:50, SEQ ID NO:51, SEQ ID NO:55, SEQ ID NO:56, SEQ ID NO:57, SEQ ID NO:58, SEQ ID NO:59, SEQ ID NO:60, SEQ ID NO:61, SEQ ID NO:65, SEQ ID NO:66, SEQ ID NO:71, SEQ ID NO:74, SEQ ID NO:75, SEQ ID NO:77, SEQ ID NO:80, SEQ ID NO:81, SEQ ID NO:87, SEQ ID NO:90, SEQ ID NO:91, SEQ ID NO:92, SEQ ID NO:115, SEQ ID NO:116, SEQ ID NO:126, SEQ ID NO:127, SEQ ID NO:129, SEQ ID NO:132, SEQ ID NO:137, SEQ ID NO:138, SEQ ID NO:139, SEQ ID NO:140, SEQ ID NO:141, SEQ ID NO:142, SEQ ID NO:143, SEQ ID NO:144, SEQ ID NO:145, SEQ ID NO:159, SEQ ID NO:162, and SEQ ID NO:164.

An additional embodiment of the invention is directed towards a method for promoting wound healing of skin or ocular and internal body tissues damaged by normal aging, disease, injury, or by surgery or other medical procedures. The method can comprise administering to the wound of an animal a composition, wherein the composition comprises any of the above described peptides. The concentration of the peptide in the composition can be about 0.01 µM to about 500 µM, about 0.1 µM to about 100 µM, about 1 µM to about 50 µM, or about 1 µM to about 10 µM. The composition can be administered to the wound topically or by systemic delivery. The animal can generally be any kind of animal, preferably is a mammal, and more preferably is a human, cow, horse, cat, dog, pig, goat, or sheep. The promotion of wound healing is preferably at least 10%, 20%, 30%, 40%, 50%, 60%, 70%, 80%, 90%, 100%, 125%, 150%, 175%, or 200% relative to the same wound not contacted with the composition.

Preferred peptides for wound healing applications include SEQ ID NO:1, SEQ ID NO:2, SEQ ID NO:5, SEQ ID NO:6, SEQ ID NO:8, SEQ ID NO:10, SEQ ID NO:11, SEQ ID NO:12, SEQ ID NO:13, SEQ ID NO:14, SEQ D NO:15, SEQ ID NO:16, SEQ ID NO:17, SEQ ID NO:20, SEQ ID NO:27, SEQ ID NO:28, SEQ ID NO:30, SEQ ID NO:32, SEQ ID NO:34, SEQ ID NO:45, SEQ ID NO:46, SEQ ID NO:50, SEQ ID NO:51, SEQ ID NO:55, SEQ ID NO:56, SEQ ID NO:57, SEQ ID NO:58, SEQ ID NO:59, SEQ ID NO:60, SEQ ID NO:61, SEQ ID NO:65, SEQ ID NO:66, SEQ ID NO:71, SEQ ID NO:74, SEQ ID NO:75, SEQ ID NO:77, SEQ ID NO:80, SEQ ID NO:81, SEQ ID NO:87, SEQ ID NO:90, SEQ ID NO:91, SEQ ID NO:92, SEQ ID NO:93, SEQ ID NO:115, SEQ ID NO:116, SEQ ID NO:126, SEQ ID NO:127, SEQ ID NO:129, SEQ ID NO:132, SEQ ID NO:137, SEQ ID NO:138, SEQ ID NO:139, SEQ ID NO:140, SEQ ID NO:141, SEQ ID NO:142, SEQ ID NO:143, SEQ ID NO:144, SEQ ID NO:145, SEQ ID NO:159, SEQ ID NO:162, and SEQ ID NO:164.

A further embodiment of the invention is directed towards methods for the additive or synergistic enhancement of the activity of a therapeutic agent. The method can comprise preparing a composition, wherein the composition comprises a peptide and a therapeutic agent. Alternatively, the method may comprise co-therapy treatment with a peptide (or peptides) used in conjunction with other therapeutic agents. The peptide can be any of the above described peptides. The therapeutic agent can generally be any therapeutic agent, and preferably is an antibiotic, an antimicrobial agent, a growth factor, a chemotherapy agent, an antimicrobial agent, lysozyme, a chelating agent, or EDTA. Preferably, the activity of the composition is higher than the activity of the same composition containing the therapeutic agent but lacking the peptide. The composition or co-therapy can be used in in vitro, in vivo, topical, oral, IV, IM, IP, and transdermal applications. The enhancement of the activity of the composition containing the therapeutic agent and the peptide is preferably at least 10%, 20%, 30%, 40%, 50%, 60%, 70%, 80%, 90%, 100%, 125%, 150%, 175%, or 200% relative to the activity of the therapeutic agent alone.

Generally, any peptide which is active on a stand-alone basis against a target is preferred for use to increase either additively or synergistically the activity of another therapeutic agent against that target. If several peptides are candidates for a given synergy application, then the less toxic peptides would be more favorably considered.

The following Examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1

Antimicrobial Assays

The data for the antimicrobial assay of the peptides have been obtained by making OD measurements in in vitro cell culture experiments with and without added peptide. The protocol used is as follows.

Cell lines included *Staphylococcus aureus* ATCC 6538 or 25923, *Pseudomonas aeruginosa* ATCC 9027 or 29853. Medium used were Antibiotic Medium 3 (Difco), Antibiotic Medium 2 (Difco), and 0.85% saline. Controls used were physiological saline, and gentamycin at 50, 25, 10, 5, 1, and 0.1 ppm.

The preparation of all media, stock solutions, and dilutions took place in a laminar flow hood to prevent contamination. Bacterial cells were freshly grown on antibiotic medium 2 agar slants (pH 7.0 at 25° C.). Bacteria were suspended and diluted in antibiotic medium 3 to about $10^4$ cfu/ml and used as the inoculum. Sample solutions (100 μl/well) were added to plates according to the plate layout. Inoculum (100 μl/well) was added to achieve a final concentration of $5 \times 10^3$ cfu/ml. Negative controls received 100 μl saline and 100 μl growth medium. Positive controls received 100 μl saline and 100 μl inoculum. Bacterial plates were incubated at 37° C. for 24 hours.

Absorbance was read at 620 nm after shaking to resuspend cells. The minimum inhibitory concentration (MIC) was defined as the lowest concentration of peptide that completely inhibits the growth of the test organism.

The yeast assay was performed in RPMI 1640 media (pH 7.0 at 25° C.).

The data presented in Table 2 were obtained using the above protocol. However, the data for Table 3 were obtained with a modified protocol wherein the medium was tryptic soy broth, inoculum strength was approximately $10^4$ CFU per ml, and values determined were minimum bactericidal concentrations (MBC) or minimum fungicidal concentrations (MFC).

The following Table 2 describes the antimicrobial properties of the peptides measured as MIC or MFC values in μg/mL. Staph6538 is *Staphylococcus aureus* ATCC accession number 6538; paerug9027 is *Pseudomonas aeruginosa* ATCC accession number 9027, yeast is *Saccharomyces cerevisiae*.

TABLE 2

| Name | SEQ ID NO: | P Number | staph6538 | paerug9027 | yeast |
|---|---|---|---|---|---|
| Hecate AC #1010 | 1 | 1 | 5 | 10 | > |
| Hecate AM | 2 | 2 | 25 | 100 | 25 |
| SB-37 AC #1018 | 3 | 5 | 100 | 50 | > |
| SB-37 AM | 5 | 12 | > | 100 | > |
| Shiva 10 AC #1015 | 6 | 13 | 10 | > | > |
| FLAK01 AM | 8 | 23 | 5 | 50 | 100 |
| FLAK04 AM | 10 | 25 | 10 | 5 | 25 |
| FLAK05 AM | 11 | 26 | 10 | 15 | > |
| FLAK06 AM | 12 | 27 | 10 | 10 | 25 |
| KAL V | 15 | 30 | > | > | ND |
| FLAK 17 AM | 16 | 34 | 5 | 50 | 25 |
| FLAK 26 AM | 17 | 35 | 5 | 200 | 25 |
| Hecate 2DAc | 19 | 37 | 5 | 100 | 50 |
| FLAK43 AM | 20 | 38 | 5 | 50 | 50 |
| FLAK44 AM | 21 | 39 | 100 | 25 | 100 |
| FLAK62 AM | 22 | 40 | 100 | 25 | 100 |
| FLAK 06R-AM | 23 | 41 | 10 | 10 | ND |
| MSI-78 AM | 24 | 42 | 10 | > | 200 |
| FLAK50 | 25 | 43 | 5 | 100 | 25 |
| FLAK51 | 26 | 44 | 5 | 5 | 50 |
| FLAK57 | 27 | 45 | 5 | 100 | 100 |
| FLAK71 | 28 | 46 | 10 | 5 | 50 |
| FLAK77 | 29 | 47 | 200 | 100 | 50 |
| FLAK50V | 30 | 48 | 5 | 5 | 25 |
| FLAK50F | 31 | 49 | 10 | 200 | 50 |
| FLAK26V AM | 32 | 50 | 5 | 15 | 50 |
| CAME-15 | 33 | 53 | 5 | 15 | 50 |
| FLAK50C | 34 | 54 | 5 | 50 | 50 |
| FLAK50D | 35 | 55 | 5 | 5 | 25 |
| FLAK 50E | 36 | 56 | 200 | 5 | 50 |
| FLAK80 | 37 | 57 | 100 | 200 | 200 |

TABLE 2-continued

| Name | SEQ ID NO: | P Number | staph6538 | paerug9027 | yeast |
|---|---|---|---|---|---|
| FLAK81 | 38 | 58 | 100 | 100 | 200 |
| FLAK82 | 39 | 59 | > | > | > |
| FLAK83M | 40 | 60 | 200 | 100 | 200 |
| FLAK 17 C | 43 | 64 | 5 | > | 200 |
| FLAK 50H | 44 | 65 | 15 | 50 | 200 |
| FLAK 50G | 45 | 66 | 5 | 50 | 100 |
| Shiva deriv P69 + KWKL | 46 | 70 | 10 | > | 100 |
| Shiva 10 (1-18_AC | 47 | 71 | 15 | 15 | 200 |
| CA(1-7)Shiva10(1-16) | 49 | 73 | 50 | 15 | 100 |
| FLAK 54 | 50 | 74 | 15 | 5 | 100 |
| FLAK 56 | 51 | 75 | 5 | 5 | 50 |
| FLAK 58 | 52 | 76 | 10 | 100 | 200 |
| FLAK 72 | 53 | 77 | 200 | 100 | 200 |
| FLAK 75 | 54 | 79 | 100 | 200 | 100 |
| Shiva 10 (1-16) Ac | 55 | 80 | 10 | 100 | 100 |
| CA(1-7)Shiva10(1-16)-COOH | 56 | 81 | 10 | > | > |
| Indolocidin-ac | 57 | 91 | 10 | > | > |
| FLAK50B | 58 | 92 | 5 | 5 | 50 |
| FLAK50I | 60 | 94 | 10 | > | > |
| FLAK50K | 61 | 95 | 100 | 200 | > |
| FLAK50L | 62 | 96 | > | > | > |
| Shiva-11 | 63 | 98 | > | > | > |
| Shiva 11 [(1-16)ME(2-9)]-COOH | 64 | 99 | 100 | > | > |
| FLAK 50N | 65 | 101 | 10 | 25 | 100 |
| FLAK 50O | 66 | 102 | 5 | 10 | 50 |
| FLAK 50P | 67 | 103 | 10 | 25 | 100 |
| CA(1-&Hecate(11/23) | 68 | 104 | 10 | 10 | 200 |
| PYL-ME | 69 | 105 | 200 | 200 | > |
| FLAG26-D1 | 70 | 106 | 100 | 25 | 100 |
| Vishnu3 | 71 | 107 | > | > | > |
| Melittin | 72 | 108 | 5 | > | 25 |
| FLAK26-D2 | 73 | 109 | > | 200 | 200 |
| FLAG26-D3 | 74 | 110 | > | 200 | 200 |
| FLAK50 Q1 | 75 | 111 | 5 | 100 | 200 |
| FLAK50 Q2 | 76 | 112 | 50 | 200 | 100 |
| FLAK50 Q3 | 77 | 113 | 10 | 200 | 200 |
| FLAK50 Q4 | 78 | 114 | 50 | 15 | 100 |
| FLAK50 Q5 | 79 | 117 | 100 | 200 | 200 |
| FLAK50 Q6 | 80 | 118 | 10 | 100 | 100 |
| FLAK50 Q7 | 81 | 119 | 50 | 25 | 50 |
| FLAK50 Q8 | 82 | 120 | 50 | 200 | 200 |
| FLAK50 Q9 | 83 | 121 | 50 | > | 100 |
| FLAK50 T1 | 85 | 123 | 50 | 200 | 100 |
| FLAK50 T2 | 86 | 124 | 5 | 100 | 100 |
| FLAK50 T3 | 87 | 125 | 10 | 100 | 50 |
| FLAK50 T4 | 88 | 126 | > | > | > |
| FLAK50 T5 | 89 | 127 | 100 | 25 | 100 |
| FLAK90 | 90 | 128 | > | 100 | 200 |
| FLAK91 | 91 | 129 | 100 | 25 | 100 |
| FLAK92 | 92 | 130 | 200 | 200 | 200 |
| FLAK93 | 93 | 131 | 25 | 10 | 100 |
| FLAK50 Z1 | 94 | 132 | > | 100 | > |
| FLAK50 Z2 | 95 | 133 | > | > | > |
| FLAK50 Z3 | 96 | 134 | 100 | > | 200 |
| FLAK50 Z4 | 97 | 135 | 15 | 10 | 50 |
| FLAK50 Z5 | 98 | 136 | 100 | 50 | 100 |
| FLAK50 Z6 | 99 | 137 | > | > | > |
| FLAK50 Z7 | 100 | 138 | > | > | > |
| FLAK50 Z8 | 101 | 139 | 50 | 25 | 200 |
| FLAK50 Z9 | 102 | 140 | > | > | > |
| FLAK94 | 103 | 141 | 15 | 50 | 200 |
| FLAK93B | 104 | 142 | 100 | 50 | 100 |
| FLAK50 Z10 | 105 | 143 | 100 | 50 | 200 |
| FLAK96 | 106 | 144 | 5 | 50 | 50 |
| FLAK97 | 107 | 145 | 200 | 100 | 200 |
| FLAK98 | 108 | 146 | 10 | 10 | 50 |
| FKRLA | 109 | 147 | 5 | 5 | 200 |
| FLAK91B | 110 | 148 | > | 200 | 200 |
| FLAK92B | 111 | 149 | 50 | 100 | 200 |
| FLAK99 | 112 | 150 | 100 | 10 | > |
| FLAK50T6 | 113 | 151 | > | > | 200 |
| FLAK50T7 | 114 | 152 | 100 | 50 | 100 |
| FLAK95 | 115 | 153 | 5 | 25 | 100 |
| FLAK50T8 | 116 | 154 | 100 | 100 | 50 |
| FLAK50T9 | 117 | 155 | > | > | > |
| FLAK100-CO2H | 118 | 156 | 15 | > | > |
| FAGVL | 119 | 157 | 200 | > | > |
| FLAK120 | 126 | 165 | 10 | 25 | 25 |
| FLAK121 | 127 | 166 | > | > | > |
| FLAK96B | 128 | 167 | 10 | 25 | 100 |
| FLAK96G | 129 | 168 | 50 | 100 | > |
| FLAK96F | 130 | 169 | 100 | 100 | 100 |
| FLAK96C | 131 | 170 | 200 | 100 | 100 |
| FLAK96D | 132 | 171 | 25 | 50 | 100 |
| FLAK 96 | 137 | 176 | > | > | > |
| FLAK 96J | 139 | 178 | 200 | 100 | > |
| FLAK 96L | 140 | 179 | 50 | 50 | 100 |
| FLAK-120G | 141 | 180 | 200 | > | > |
| FLAK-120D | 142 | 181 | 100 | 200 | 100 |
| FLAK-120C | 143 | 182 | > | > | > |
| FLAK-120B | 144 | 183 | 200 | 100 | 200 |
| FLAK-120F | 145 | 184 | 25 | 100 | 100 |
| FLAK 50M | 165 | 97 | 5 | 50 | 50 |

> indicates greater than 200 μg/mL;
ND = not determined.

The following Table 3 describes describes the antimicrobial properties of the peptides measured as minimum bactericidal or minimum fungicidal (*Candida*) concentrations. MBC or MFC values are in μg/mL. *E. coli* is *Escherichia coli* ATCC accession number 25922; *P. aerug* is *Pseudomonas aeruginosa* ATCC accession number 27853, *S. aur.* is *Stapholococcus aureus* ATCC accession number 25923; *Candida* is *Candida albicans* ATCC accession number 10231.

TABLE 3

| SEQ ID NO: | P # | E. coli A.25922 | P. aerug A.27853 | S. aur A.25923 | Candida A.10231 |
|---|---|---|---|---|---|
| 1 | 1 | 25 | 30 | 25 | >50 |
| 2 | 2 | 25 | 10 | 25 | >50 |
| 3 | 5 | 50 | >60 | 40 | ND |
| 4 | 11 | 40 | 25 | 25 | >50 |
| 5 | 12 | 50 | >60 | 75 | ND |
| 6 | 13 | 8 | 15 | 30 | >50 |
| 8 | 23 | 15 | 25 | 30 | >50 |
| 9 | 24 | >80 | 30 | >40 | >50 |
| 10 | 25 | 40 | 30 | 40 | >50 |
| 11 | 26 | >80 | >40 | >40 | >50 |
| 12 | 27 | 10 | 8 | 8 | >50 |
| 13 | 27B | 40 | 10 | >40 | >40 |
| 14 | 27C | 10 | 4 | >40 | >40 |
| 15 | 30 | 10 | 15 | 40 | >50 |
| 16 | 34 | 15 | 15 | 40 | >40 |
| 17 | 35 | 8 | 8 | 10 | >40 |
| 18 | 36 | 30 | 15 | 10 | >40 |
| 19 | 37 | 8 | 8 | 40 | >50 |
| 20 | 38 | 15 | 30 | 15 | ND |
| 21 | 39 | >40 | >40 | >40 | ND |
| 22 | 40 | 30 | 40 | >40 | ND |
| 23 | 41 | 40 | 40 | 40 | ND |
| 24 | 42 | 10 | 30 | 10 | ND |
| 25 | 43 | 8 | 15 | 4 | 15 |
| 26 | 44 | 10 | 55 | 30 | >50 |
| 27 | 45 | 30 | 40 | 80 | >50 |
| 29 | 47 | >50 | >50 | >50 | >50 |
| 30 | 48 | 8 | 25 | 4 | 10 |

TABLE 3-continued

| SEQ ID NO: | P # | E. coli A.25922 | P. aerug A.27853 | S. aur A.25923 | Candida A.10231 |
|---|---|---|---|---|---|
| 31 | 49 | 40 | 30 | 50 | 30 |
| 32 | 50 | 50 | 25 | 25 | >50 |
| 33 | 53 | 15 | 15 | 10 | 30 |
| 34 | 54 | 15 | 40 | 15 | 30 |
| 35 | 55 | 4 | 10 | 4 | 25 |
| 36 | 56 | 50 | 10 | 55 | 30 |
| 37 | 57 | >50 | >50 | >50 | >50 |
| 38 | 58 | >50 | >50 | >50 | >50 |
| 39 | 59 | >50 | >50 | >50 | >50 |
| 40 | 60 | >50 | >50 | >50 | >50 |
| 41 | 61 | 4 | 50 | >80 | >40 |
| 42 | 63 | 10 | 50 | 15 | 60 |
| 43 | 64 | 10 | 30 | 4 | >50 |
| 44 | 65 | >55 | >50 | >55 | >50 |
| 45 | 66 | 40 | 50 | 30 | 40 |
| 46 | 70 | 40 | 30 | 40 | >50 |
| 47 | 71 | 50 | 40 | >50 | >50 |
| 48 | 72 | >50 | 40 | >50 | >50 |
| 50 | 74 | >55 | 50 | >55 | >55 |
| 51 | 75 | 40 | 30 | >55 | 30 |
| 52 | 76 | 40 | >55 | >55 | >50 |
| 53 | 77 | >50 | >50 | >50 | >50 |
| 54 | 79 | >50 | >50 | >50 | >50 |
| 55 | 80 | 30 | 15 | >50 | >50 |
| 58 | 92 | 40 | 25 | 15 | 25 |
| 59 | 93 | >50 | >50 | >50 | >50 |
| 60 | 94 | >50 | >50 | >50 | >50 |
| 61 | 95 | >50 | >50 | >50 | >50 |
| 62 | 96 | >50 | >50 | >50 | >50 |
| 65 | 101 | 300 | >50 | >50 | 40 |
| 66 | 102 | 25 | 30 | 25 | 15 |
| 67 | 103 | 30 | 30 | >50 | 25 |
| 69 | 105 | 25 | >50 | ND | >50 |
| 70 | 106 | 50 | >50 | ND | >50 |
| 71 | 107 | ND | >50 | >50 | >50 |
| 72 | 108 | >50 | >50 | 25 | >50 |
| 73 | 109 | ND | ND | 80 | >50 |
| 74 | 110 | 8 | >50 | >50 | >50 |
| 75 | 111 | 30 | ND | 40 | INACT |
| 76 | 112 | 30 | INACT | INACT | INACT |
| 77 | 113 | INACT | INACT | INACT | 40 |
| 79 | 117 | INACT | INACT | INACT | INACT |
| 80 | 118 | 8 | 25 | 10 | 25 |
| 81 | 119 | 15 | 30 | 4 | 25 |
| 82 | 120 | INACT | INACT | INACT | INACT |
| 83 | 121 | INACT | INACT | INACT | 50 |
| 84 | 122 | 30 | 30 | 25 | 15 |
| 85 | 123 | 40 | INACT | INACT | 25 |
| 86 | 124 | 10 | 40 | 8 | 15 |
| 87 | 125 | 40 | 40 | INACT | 40 |
| 88 | 126 | INACT | INACT | INACT | INACT |
| 89 | 127 | INACT | INACT | INACT | INACT |
| 90 | 128 | INACT | INACT | INACT | INACT |
| 91 | 129 | INACT | INACT | INACT | INACT |
| 92 | 130 | INACT | INACT | INACT | INACT |
| 93 | 131 | INACT | INACT | INACT | INACT |
| 94 | 132 | INACT | INACT | INACT | INACT |
| 95 | 133 | INACT | INACT | INACT | INACT |
| 96 | 134 | INACT | INACT | INACT | INACT |
| 97 | 135 | INACT | 40 | INACT | 25 |
| 98 | 136 | INACT | INACT | INACT | INACT |
| 99 | 137 | INACT | INACT | INACT | INACT |
| 100 | 138 | INACT | INACT | INACT | INACT |
| 101 | 139 | INACT | INACT | INACT | INACT |
| 102 | 140 | INACT | INACT | INACT | INACT |
| 103 | 141 | INACT | INACT | INACT | INACT |
| 104 | 142 | INACT | INACT | INACT | INACT |
| 105 | 143 | INACT | INACT | INACT | INACT |
| 106 | 144 | 10 | 25 | 25 | 25 |
| 107 | 145 | INACT | INACT | INACT | 100 |
| 108 | 146 | 10 | >250 | 75 | 10 |
| 109 | 147 | 25 | 75 | >250 | >250 |
| 110 | 148 | 150 | >250 | >250 | 100 |
| 111 | 149 | 150 | >250 | >250 | 100 |
| 112 | 150 | 75 | >250 | >250 | 50 |
| 113 | 151 | >250 | >250 | >250 | 100 |
| 114 | 152 | 150 | 150 | >250 | 50 |
| 115 | 153 | 10 | 25 | >5 | 25 |
| 116 | 154 | 50 | 100 | >250 | 25 |
| 117 | 155 | >250 | >250 | >250 | >250 |
| 118 | 156 | 100 | >250 | >250 | >250 |
| 119 | 157 | 75 | >250 | >250 | >250 |
| 120 | 159 | 10 | 10 | >250 | 50 |
| 121 | 160 | >250 | >250 | >250 | >250 |
| 122 | 161 | 150 | >250 | >250 | 25 |
| 123 | 162 | 50 | >250 | >250 | 100 |
| 124 | 163 | 25 | 50 | 25 | 25 |
| 125 | 164 | 25 | 25 | 25 | 25 |
| 126 | 165 | 10 | 25 | 25 | 10 |
| 127 | 166 | >250 | >250 | >250 | >250 |
| 128 | 167 | 25 | >250 | 10 | 25 |
| 129 | 168 | 75 | 100 | >250 | 150 |
| 130 | 169 | 200 | >250 | >250 | 75 |
| 131 | 170 | 25 | >250 | 150 | 25 |
| 132 | 171 | 75 | 100 | >250 | 50 |
| 133 | 172 | >250 | >250 | >250 | >250 |
| 134 | 173 | >250 | >250 | >250 | 150 |
| 162 | 67 | 25 | 30 | 30 | >50 |
| 165 | 97 | 25 | >50 | 25 | 25 |

INACT refers to no detectable activity.
ND indicates no data available.

Example 2

Anti-cancer Assays

Cancer cell assays were performed in a manner similar to the anti-microbial assays described above, except that the assay procedure used the MTT dye protocol. Viability of cells is determined by the dye response. In the following procedure, approximately $1.5 \times 10^4$ cells per well were added and viability was determined with the cells in a semi-confluent state. The assay was performed in a 96-well microtiter plate. After addition of peptide, the plate was set for 24 hours. MTT (5 mg/ml in phenol red-free RPMI-1640, 20 µl) was added to each well including positive control wells untreated with peptide. The plate was incubated at 37° C. for 4 hours. The liquid contents of each well was removed, and isopropanol with 0.1 M HCl (100 µl) was added to each well. The plate was sealed with parafilm to prevent evaporation of the isopropanol. The plate is allowed to rest for 5-10 minutes in order to solubilize the precipitate. Purified water (100 µl) was added to each well. Absorbance was determined with an ELISA Reader instrument. Color intensity at 540 nm is proportional to viability of cells. Results for each concentration of peptide are plotted relative to untreated controls, and LD50 values are determined from the graphs.

WI38 (ATCC No. CCL75) is a normal fibroblast line of lung diploid cells, MCF7 (ATCC No. HTB22) is a breast adenocarcinoma tumor cell line, SW480 (ATCC No. CCL228) is a colon adenocarcinoma tumor cell line, BMKC is a cloned melanoma line derived from Bowes melanoma line HMCB (ATCC No. CRL9607), H1299 (ATCC No. CRL5803) is a lung large cell carcinoma tumor line, HeLaS3 (ATCC No. CCL2.2) is a cervical epitheleal carcinoma tumor cell line, and PC3 (ATCC No. CRL1435) is a prostate adenocarcinoma tumor cell line. Numbers are $LD_{50}$ values (µg/mL). Data on the six targets are presented in the following Tables 4 and 5.

TABLE 4

| Name | SEQ ID NO: | P No. | WI38 | MCF7 | SW480 | BMKC |
|---|---|---|---|---|---|---|
| HECATE AC | 1 | 1 | 27 | 54 | 6 | 72 |
| HECATE AM | 2 | 2 | 66 | 23 | 46 | 128 |
| SB37COOH | 3 | 5 | 130 | 175 | 82 | 120 |
| SB-37 AM | 5 | 12 | 950 | 540 | > | > |
| SHIVA 10 AC | 6 | 13 | 57 | > | ND | ND |
| FLAK01 AM | 8 | 23 | 34 | 62 | 5 | 27 |
| FLAK03 AM | 9 | 24 | 55 | 26 | 38 | 85 |
| FLAK04 AM | 10 | 25 | 24 | 10 | 12 | 36 |
| FLAK05 AM | 11 | 26 | 96 | 74 | 8 | 94 |
| FLAK06 AM | 12 | 27 | 37 | 14 | 26 | 44 |
| FLAK06 AC | 13 | 27B | 101 | 65 | 59 | 93 |
| FLAK06 R-AC | 14 | 27C | 520 | 140 | 210 | 300 |
| KAL V | 15 | 30 | 93 | 72 | 62 | 140 |
| FLAK 17 AM | 16 | 34 | 40 | 21 | 35 | 53 |
| FLAK 26 AM | 17 | 35 | 8 | 9 | 14 | 7 |
| FLAK 25 AM | 18 | 36 | 19 | 9 | 30 | 56 |
| HECATE 2DAc | 19 | 37 | 80 | 14 | 57 | 150 |
| FLAK43 AM | 20 | 38 | 12 | 17 | 13 | 21 |
| FLAK44 AM | 21 | 39 | 300 | 130 | 435 | 510 |
| FLAK62 AM | 22 | 40 | > | 760 | > | > |
| FLAK 06R-AM | 23 | 41 | 175 | 98 | 120 | 290 |
| MSI-78 AM | 24 | 42 | 67 | 31 | 34 | 140 |
| FLAK50 | 25 | 43 | 5 | 9 | 9 | 7 |
| FLAK51 | 26 | 44 | 36 | 140 | 32 | 47 |
| FLAK57 | 27 | 45 | 200 | 260 | 180 | 160 |
| FLAK71 | 28 | 46 | 200 | 300 | 160 | 150 |
| FLAK77 | 29 | 47 | > | 575 | > | 700 |
| FLAK50V | 30 | 48 | 41 | 23 | 47 | 43 |
| FLAK50F | 31 | 49 | 135 | 40 | 100 | 115 |
| FLAK26V AM | 32 | 50 | 43 | 32 | 46 | 40 |
| CAME-15 | 33 | 53 | 32 | 45 |  | 40 |
| FLAK50C | 34 | 54 | 97 | 60 |  | 90 |
| FLAK50D | 35 | 55 | 32 | 16 | 14 | 16 |
| FLAK 50E | 36 | 56 | 250 | 500 | 215 | 205 |
| FLAK80 | 37 | 57 | 900 | > | 740 | 740 |
| FLAK81 | 38 | 58 | > | > | > | > |
| FLAK82 | 39 | 59 | 77 | 31 | 42 | 155 |
| FLAK83M | 40 | 60 | > | > | > | > |
| FLAK 26 Ac | 41 | 61 | 93 | 105 | 100 | 140 |
| INDOLICIDIN | 42 | 63 | ND | 64 | 345 | 200 |
| FLAK 17 C | 43 | 64 | 37 | 80 |  | 35 |
| FLAK 50H | 44 | 65 | 320 | 475 | 345 | 250 |
| FLAK 50G | 45 | 66 | 240 | 90 | 145 | 200 |
| SHIVA DERIV P69 + KWKL | 46 | 70 | 34 | 44 | 11 | 94 |
| SHIVA 10 (1-18_AC | 47 | 71 | 355 | 190 | 250 | 445 |
| SHIVA 10 PEPTIDE 71 + KWKL | 48 | 72 | 125 | 93 | 82 | 290 |
| CA(1-7)Shiva10(1-16) | 49 | 73 | 160 | 150 | 70 | 360 |
| FLAK 54 | 50 | 74 | 335 | 465 | 340 | 460 |
| FLAK 56 | 51 | 75 | 80 | 42 | 17 | 24 |
| FLAK 58 | 52 | 76 | 445 | 970 | 400 | 750 |
| FLAK 72 | 53 | 77 | > | > | > | 125 |
| FLAK 75 | 54 | 79 | > | 540 | > | 830 |
| SHIVA 10 (1-16) Ac | 55 | 80 | 28 | 29 | 35 | 76 |
| CA(1-7)Shiva10(1-16)-COOH | 56 | 81 | 8 | 63 | 13 | 12 |
| INDOLOCIDIN-ac | 57 | 91 | 9 | 12 | 30 | 180 |
| FLAK50B | 58 | 92 | 43 | 23 | 51 | 46 |
| FLAK50I | 60 | 94 | 6 | 65 | ND | 11 |
| FLAK50K | 61 | 95 | 250 | > | > | 820 |
| FLAK50L | 62 | 96 | > | > | > | > |
| Shiva-11 | 63 | 98 | 47 | 96 | 125 | 94 |
| SHIVA 11 [(1-16)ME(2-9)-COOH | 64 | 99 | 34 | 95 | 120 | 94 |
| FLAK 50N | 65 | 101 | 300 | 250 | 170 | 160 |
| FLAK 50O | 66 | 102 | 73 | 60 | 57 | 60 |
| FLAK 50P | 67 | 103 | 26 | 46 | 90 | 75 |
| CA(1-&HECATE(11/23) | 68 | 104 | 24 | 11 | 54 | 100 |
| PYL-ME | 69 | 105 | 430 | 635 | > | ND |
| FLAG26-D1 | 70 | 106 | > | 620 | 570 | 690 |
| VISHNU3 | 71 | 107 | > | > | > | > |
| MELITTIIN | 72 | 108 | 16 | 9 | 23 | 18 |
| FLAK26-D2 | 73 | 109 | > | > | > | > |
| FLAG26-D3 | 74 | 110 | 45 | 180 | 325 | 400 |
| FLAK50 Q1 | 75 | 111 | 24 | 35 | 27 | 26 |
| FLAK50 Q2 | 76 | 112 | 420 | 500 | 800 | 445 |
| FLAK50 Q3 | 77 | 113 | 170 | 150 | 180 | 115 |
| FLAK50 Q4 | 78 | 114 | > | 730 | > | > |
| FLAK50 Q5 | 79 | 117 | > | > | > | > |
| FLAK50 Q6 | 80 | 118 | 170 | 70 | 115 | 135 |
| FLAK50 Q7 | 81 | 119 | 45 | 54 | 46 | 36 |
| FLAK50 Q8 | 82 | 120 | 600 | 730 | 630 | 660 |
| FLAK50 Q9 | 83 | 121 | 625 | 400 | 800 | 670 |
| FLAK50 Q10 | 84 | 122 | 720 | 360 | 570 | 700 |
| FLAK50 T1 | 85 | 123 | 600 | 615 | > | 635 |
| FLAK50 T2 | 86 | 124 | 21 | 18 | 9 | 10 |
| FLAK50 T3 | 87 | 125 | 90 | 90 | 125 | 220 |
| FLAK50 T4 | 88 | 126 | > | > | > | > |
| FLAK50 T5 | 89 | 127 | 760 | 440 | 400 | 535 |
| FLAK90 | 90 | 128 | 500 | 500 | 530 | 330 |
| FLAK91 | 91 | 129 | > | > | 550 | > |
| FLAK92 | 92 | 130 | > | > | > | > |
| FLAK93 | 93 | 131 | > | 600 | 555 | > |
| FLAK50 Z1 | 94 | 132 | > | > | > | > |
| FLAK50 Z2 | 95 | 133 | > | > | > | > |
| FLAK50 Z3 | 96 | 134 | > | > | 740 | > |
| FLAK50 Z4 | 97 | 135 | 110 | 54 | 80 | 155 |
| FLAK50 Z5 | 98 | 136 | > | 500 | 600 | 530 |
| FLAK50 Z6 | 99 | 137 | > | > | > | > |
| FLAK50 Z7 | 100 | 138 | > | > | > | > |
| FLAK50 Z8 | 101 | 139 | 550 | 625 | > | 525 |
| FLAK50 Z9 | 102 | 140 | > | > | > | > |
| FLAK94 | 103 | 141 | 420 | 430 | 560 | 465 |
| FLAK93B | 104 | 142 | 73 | 44 | 38 | 38 |
| FLAK50 Z10 | 105 | 143 | > | > | > | > |
| FLAK96 | 106 | 144 | 750 | 150 | 285 | 250 |
| FLAK97 | 107 | 145 | > | > | > | > |
| FLAK98 | 108 | 146 | 270 | 110 | 380 | 185 |
| FKRLA | 109 | 147 | 83 | 106 | 185 | 110 |
| FLAK91B | 110 | 148 | 380 | 315 | > | 330 |
| FLAK92B | 111 | 149 | > | > | > | > |
| FLAK99 | 112 | 150 | 125 | 160 | 235 | 190 |
| FLAK50T6 | 113 | 151 | > | > | > | > |
| FLAK50T7 | 114 | 152 | 620 | 430 | 740 | > |
| FLAK95 | 115 | 153 | 130 | 64 | 61 | 165 |
| FLAK50T8 | 116 | 154 | 600 | 315 | 750 | 330 |
| FLAK50T9 | 117 | 155 | > | > | > | > |
| FLAK100-CO2H | 118 | 156 | 230 | 135 | 345 | 520 |
| FAGVL | 119 | 157 | 500 | 240 | 530 | 600 |
| Modelin-5 | 120 | 159 | 82 | 61 | 140 | 140 |
| Modelin-5-CO2H | 121 | 160 | 700 | 320 | 370 | 220 |
| FLAK120 | 126 | 165 | 470 | 360 | 240 | 240 |
| FLAK121 | 127 | 166 | > | > | > | > |
| FLAK96B | 128 | 167 | 260 | 230 | 360 | 240 |
| FLAK96G | 129 | 168 | > | 630 | > | 590 |
| FLAK96F | 130 | 169 | > | 510 | > | 530 |
| FLAK96C | 131 | 170 | > | 940 | > | > |
| FLAK96D | 132 | 171 | 615 | 305 | 770 | 600 |
| Modelin-8D | 135 | 174 | > | > | > | > |
| Modelin-8E | 136 | 175 | > | > | 70 | > |
| Flak 96H | 137 | 176 | > | > | > | > |
| Flak 96I | 138 | 177 | 270 | 190 | 310 | 310 |
| Flak 96J | 139 | 178 | 405 | 770 | > | 640 |
| Flak 96L | 140 | 179 | 540 | 555 | > | 920 |
| FLAK-120G | 141 | 180 | 940 | 950 | 600 | 770 |
| FLAK-120D | 142 | 181 | 500 | 550 | 870 | 830 |
| FLAK-120C | 143 | 182 | > | > | > | > |
| FLAK-120B | 144 | 183 | > | > | > | > |
| FLAK-120F | 145 | 184 | 800 | 260 | 440 | 600 |
| Magainin2wisc | 146 | 300 | 52 | 22 | 60 | 130 |
| D2A21 | 147 | 301 | 66 | 64 | 76 | 140 |
| KSL-1 | 148 | 302 | 800 | 340 | > | 700 |
| KSL-7 | 149 | 303 | 355 | 315 | 530 | 330 |
| LSB-37 | 150 | 306 | 320 | 50 | 240 | 170 |
| Anubis-2 | 151 | 307 | 75 | 38 | 73 | 83 |

TABLE 4-continued

| Name | SEQ ID NO: | P No. | WI38 | MCF7 | SW480 | BMKC |
|---|---|---|---|---|---|---|
| FLAK 17 CV | 152 | 501 | 26 | 23 | ND | ND |
| FLAK50 Q1 V | 153 | 502 | 64 | 92 | ND | ND |
| D2A21V | 154 | 503 | 150 | 210 | ND | ND |
| FLAK 25 AM V | 155 | 504 | 110 | 130 | ND | ND |
| FLAK43 AM V | 156 | 505 | 85 | 86 | ND | ND |
| FLAK50D V | 157 | 506 | 75 | 45 | ND | ND |
| HECATE AM V | 158 | 507 | 285 | 340 | ND | ND |
| HECATE AC V | 159 | 508 | 190 | 160 | ND | ND |
| FLAK04 AM V | 160 | 509 | 95 | 84 | ND | ND |
| 03 AM V | 161 | 510 | 77 | 62 | ND | ND |
|  | 162 | 67 | 4 | 7 | ND | ND |
|  | 163 | 100 | 95 | 175 | 82 | 120 |
|  | 164 | 69 | 101 | 45 | 63 | 66 |

Note:
> indicates greater than 1000;
ND indicates not determined;
numbers are in µg/mL.

TABLE 5

| Name | SEQ ID NO: | P No. | WI38 | H1299 | HeLaS3 | PC3 |
|---|---|---|---|---|---|---|
| HECATE AC | 1 | 1 | 27 | 44 | 95 | 61 |
| HECATE AM | 2 | 2 | 66 | 140 | 50 | 44 |
| SB37COOH | 3 | 5 | 130 | 220 | 150 | ND |
| SB-37 AM | 5 | 12 | 950 | 720 | > | 630 |
| SHIVA 10 AC | 6 | 13 | 57 | > | > | 83 |
| FLAK01 AM | 8 | 23 | 34 | 64 | 82 | 41 |
| FLAK03 AM | 9 | 24 | 55 | 72 | 145 | 38 |
| FLAK04 AM | 10 | 25 | 24 | 37 | 20 | 12 |
| FLAK05 AM | 11 | 26 | 96 | 84 | 150 | 125 |
| FLAK06 AM | 12 | 27 | 37 | 16 | 25 | 8 |
| FLAK06 AC | 13 | 27B | 101 | 54 | 80 | 16 |
| FLAK06 AM | 14 | 27C | 520 | 170 | 260 | 280 |
| KAL V | 15 | 30 | 93 | 125 | 190 | 65 |
| FLAK 17 AM | 16 | 34 | 40 | 24 | 62 | 9 |
| FLAK 26 AM | 17 | 35 | 8 | 16 | 27 | 5 |
| FLAK 25 AM | 18 | 36 | 19 | 57 | ND | 19 |
| HECATE 2DAc | 19 | 37 | 80 | 150 | ND | 64 |
| FLAK43 AM | 20 | 38 | 12 | 33 | 35 | 10 |
| FLAK44 AM | 21 | 39 | 300 | 420 | 620 | 310 |
| FLAK62 AM | 22 | 40 | > | > | > | 435 |
| FLAK 06R-AM | 23 | 41 | 175 | 245 | 185 | 140 |
| MSI-78 AM | 24 | 42 | 67 | 150 | ND | 66 |
| FLAK50 | 25 | 43 | 5 | 6 | 15 | 12 |
| FLAK51 | 26 | 44 | 36 | 72 | 22 | 45 |
| FLAK57 | 27 | 45 | 200 | 330 | 160 | 170 |
| FLAK71 | 28 | 46 | 200 | 290 | 280 | 280 |
| FLAK77 | 29 | 47 | > | > | > | > |
| FLAK50V | 30 | 48 | 41 | 17 | 44 | 32 |
| FLAK50F | 31 | 49 | 135 | 140 | ND | 77 |
| FLAK26V AM | 32 | 50 | 43 | 7 | 33 | 54 |
| CAME-15 | 33 | 53 | 32 | 65 | 30 | 40 |
| FLAK50C | 34 | 54 | 97 | 80 | 190 | 90 |
| FLAK50D | 35 | 55 | 32 | 7 | 15 | 47 |
| FLAK 50E | 36 | 56 | 250 | 370 | 300 | 435 |
| FLAK80 | 37 | 57 | 900 | > | 830 | > |
| FLAK81 | 38 | 58 | > | > | > | > |
| FLAK82 | 39 | 59 | 77 | 180 | ND | 81 |
| FLAK83M | 40 | 60 | > | > | > | > |
| FLAK 26 Ac | 41 | 61 | 93 | 127 | 170 | 66 |
| INDOLICIDIN | 42 | 63 | ND | 270 | 345 | 290 |
| FLAK 17 C | 43 | 64 | 37 | 30 | 30 | 46 |
| FLAK 50H | 44 | 65 | 320 | 450 | 210 | 470 |
| FLAK 50G | 45 | 66 | 240 | 130 | 140 | 170 |
| SHIVA DERIV P69 + KWKL | 46 | 70 | 34 | 63 | 28 | 82 |
| SHIVA 10 (1-18_ AC | 47 | 71 | 355 | 320 | 570 | 270 |
| SHIVA 10 PEPTIDE 71 + KWKL | 48 | 72 | 125 | 160 | 240 | 63 |
| CA(1-7)Shiva10(1-16) | 49 | 73 | 160 | 115 | 270 | 97 |
| FLAK 54 | 50 | 74 | 335 | 670 | 260 | 660 |
| FLAK 56 | 51 | 75 | 80 | 80 | 74 | 54 |
| FLAK 58 | 52 | 76 | 445 | 860 | 380 | 675 |
| FLAK 72 | 53 | 77 | > | > | > | > |
| FLAK 75 | 54 | 79 | > | > | > | > |
| SHIVA 10 (1-16) Ac | 55 | 80 | 28 | 64 | 97 | 28 |
| CA(1-7)Shiva10(1-16)-COOH | 56 | 81 | 8 | 22 | 19 | 170 |
| Indolocidin-ac | 57 | 91 | 9 | 64 | 20 | 31 |
| FLAK50B | 58 | 92 | 43 | 25 | 670 | 83 |
| FLAK50J | 59 | 93 | 530 | 320 | > | 690 |
| FLAK50I | 60 | 94 | 6 | ND | > | ND |
| FLAK50K | 61 | 95 | 250 | > | > | > |
| FLAK50L | 62 | 96 | > | > | > | > |
| Shiva-11 | 63 | 98 | 47 | 53 | 175 | 52 |
| SHIVA 11 [(1-16)ME(2-9)]-COOH | 64 | 99 | 34 | 54 | 180 | 28 |
| FLAK 50N | 65 | 101 | 300 | 340 | 170 | 730 |
| FLAK 50O | 66 | 102 | 73 | 27 | 43 | 66 |
| FLAK 50P | 67 | 103 | 26 | 150 | 70 | 330 |
| CA(1-&HECATE(11/23) | 68 | 104 | 24 | 52 | 130 | 18 |
| PYL-ME | 69 | 105 | 430 | > | > | ND |
| FLAG26-D1 | 70 | 106 | > | 920 | 700 | > |
| VISHNU3 | 71 | 107 | > | > | > | > |
| MELITTIIN | 72 | 108 | 16 | 25 | 35 | 13 |
| FLAK26-D2 | 73 | 109 | > | > | > | > |
| FLAG26-D3 | 74 | 110 | 45 | 95 | 540 | > |
| FLAK50 Q1 | 75 | 111 | 24 | 8 | 7 | 11 |
| FLAK50 Q2 | 76 | 112 | 420 | 470 | 660 | 640 |
| FLAK50 Q3 | 77 | 113 | 170 | 50 | 190 | 240 |
| FLAK50 Q4 | 78 | 114 | > | > | > | > |
| FLAK50 Q5 | 79 | 117 | > | > | > | > |
| FLAK50 Q6 | 80 | 118 | 170 | 74 | 87 | 330 |
| FLAK50 Q7 | 81 | 119 | 45 | 33 | 30 | 140 |
| FLAK50 Q8 | 82 | 120 | 600 | 620 | 810 | > |
| FLAK50 Q9 | 83 | 121 | 625 | 460 | 830 | > |
| FLAK50 Q10 | 84 | 122 | 720 | 830 | 780 | 800 |
| FLAK50 T1 | 85 | 123 | 600 | > | 940 | > |
| FLAK50 T2 | 86 | 124 | 21 | 30 | 14 | 10 |
| FLAK50 T3 | 87 | 125 | 90 | 76 | 220 | 145 |
| FLAK50 T4 | 88 | 126 | > | > | > | > |
| FLAK50 T5 | 89 | 127 | 760 | 770 | 610 | > |
| FLAK90 | 90 | 128 | 500 | > | 700 | > |
| FLAK91 | 91 | 129 | > | 790 | 550 | > |
| FLAK92 | 92 | 130 | > | > | > | > |
| FLAK93 | 93 | 131 | > | > | > | > |
| FLAK50 Z1 | 94 | 132 | > | > | > | > |
| FLAK50 Z2 | 95 | 133 | > | > | > | > |
| FLAK50 Z3 | 96 | 134 | > | > | > | > |
| FLAK50 Z4 | 97 | 135 | 110 | 115 | 215 | 310 |
| FLAK50 Z5 | 98 | 136 | > | 450 | 400 | 900 |
| FLAK50 Z6 | 99 | 137 | > | > | > | > |
| FLAK50 Z7 | 100 | 138 | > | > | > | > |
| FLAK50 Z8 | 101 | 139 | 550 | 850 | > | > |
| FLAK50 Z9 | 102 | 140 | > | > | 285 | > |
| FLAK94 | 103 | 141 | 420 | > | > | ND |
| FLAK93B | 104 | 142 | 73 | 115 | 55 | 60 |
| FLAK50 Z10 | 105 | 143 | > | > | > | > |
| FLAK96 | 106 | 144 | 750 | 225 | 275 | 350 |
| FLAK97 | 107 | 145 | > | > | 240 | > |
| FLAK98 | 108 | 146 | 270 | 93 | 640 | 440 |
| FKRLA | 109 | 147 | 83 | 93 | > | 340 |
| FLAK91B | 110 | 148 | 380 | 660 | > | > |
| FLAK92B | 111 | 149 | > | > | > | > |
| FLAK99 | 112 | 150 | 125 | 185 | 320 | 74 |
| FLAK50T6 | 113 | 151 | > | > | > | > |
| FLAK50T7 | 114 | 152 | 620 | 410 | > | > |
| FLAK95 | 115 | 153 | 130 | 50 | 140 | 97 |
| FLAK50T8 | 116 | 154 | 600 | 400 | > | 640 |
| FLAK50T9 | 117 | 155 | > | > | > | ND |
| FLAK100-CO2H | 118 | 156 | 230 | ND | > | 260 |

TABLE 5-continued

| Name | SEQ ID NO: | P No. | WI38 | H1299 | HeLaS3 | PC3 |
|---|---|---|---|---|---|---|
| FAGVL | 119 | 157 | 500 | 315 | > | 375 |
| Modelin-5 | 120 | 159 | 82 | 74 | 275 | 145 |
| Modelin-5-CO2H | 121 | 160 | 700 | 470 | 550 | 450 |
| FLAK120 | 126 | 165 | 470 | 56 | 400 | 340 |
| FLAK121 | 127 | 166 | > | > | > | > |
| FLAK96B | 128 | 167 | 260 | 300 | 325 | 320 |
| FLAK96G | 129 | 168 | > | > | > | > |

TABLE 6

FLAK peptides showing substantial activity against cancer cell lines

| LD50 values | Number of "active" peptides | Percent of 150 peptides tested |
|---|---|---|
| < or = 50 µg/ml | 44 | 29% |
| < or = 25 µg/ml | 26 | 17% |
| < or = 10 µg/ml | 16 | 11% |

TABLE 7

Activity and specificity of FLAK peptides against six cancer cell targets

| | Number of active peptides per target | | | | | |
|---|---|---|---|---|---|---|
| LD50 | MCF7 (breast) | SW480 (colon) | BMKC (melanoma) | H1299 (lung) | HeLaS3 (cervix) | PC3 (prostate) |
| < or = 50 µg/ml | 31 | 25 | 19 | 19 | 17 | 20 |
| < or = 25 µg/ml | 17 | 13 | 8 | 10 | 8 | 11 |
| < or = 10 µg/ml | 6 | 5 | 3 | 4 | 1 | 5 |

TABLE 5-continued

| Name | SEQ ID NO: | P No. | WI38 | H1299 | HeLaS3 | PC3 |
|---|---|---|---|---|---|---|
| FLAK96F | 130 | 169 | > | 640 | > | > |
| FLAK96C | 131 | 170 | > | > | > | > |
| FLAK96D | 132 | 171 | 615 | 540 | 820 | 600 |
| Modelin-8D | 135 | 174 | > | > | > | > |
| Modelin-8E | 136 | 175 | > | > | 510 | > |
| Flak 96H | 137 | 176 | > | > | > | > |
| Flak 96I | 138 | 177 | 270 | 240 | 380 | 120 |
| Flak 96J | 139 | 178 | 405 | > | > | > |
| Flak 96L | 140 | 179 | 540 | > | > | > |
| FLAK-120G | 141 | 180 | 940 | > | 760 | > |
| FLAK-120D | 142 | 181 | 500 | > | > | > |
| FLAK-120C | 143 | 182 | > | > | > | > |
| FLAK-120B | 144 | 183 | > | > | > | > |
| FLAK-120F | 145 | 184 | 800 | 370 | 302 | 570 |
| Magainin2wisc | 146 | 300 | 52 | 60 | 125 | 45 |
| D2A21 | 147 | 301 | 66 | 77 | 170 | 45 |
| KSL-1 | 148 | 302 | 800 | 720 | > | > |
| KSL-7 | 149 | 303 | 355 | 345 | > | 530 |
| LSB-37 | 150 | 306 | 320 | 120 | 250 | 370 |
| Anubis-2 | 151 | 307 | 75 | 160 | 100 | 66 |
| | 163 | | 100 | 95 | 220 | 150 | ND |
| | 164 | | 69 | 101 | 71 | 190 | 81 |

Note:
> indicates greater than 1000;
ND indicates not determined;
numbers are in µg/mL.

It can be seen from Tables 4 and 5 that all targets challenged were inhibited by one or more of the peptides to an appreciable extent (i.e. LD50 less than 50 µg/ml). Table 6 below shows that 44 (29%) of the 150 peptides tested were active with some LD50 values at or below 50; 26 of the peptides were active on some targets at or below the LD50 value of 25; and 16 peptides were very active on one or more target strains with LD50 values at or below 10.

Table 7 below shows a broad spectrum of activity against six cancer cell types for various active peptides. It is noted that each target has one or more lead candidate peptides inhibitory to cell growth at an LD50 level of 10 or less.

Example 3

Stimulation and Proliferation of Leukocytes

In vitro viability of human leukocyte cells in the presence of different peptides at different concentrations was determined by an Alamar Blue protocol. Alamar Blue (Promega, Madison, Wis.) is an indicator dye, formulated to measure quantitatively the proliferation and cytotoxicity of the cells. The dye consists of an oxidation-reduction (redox) indicator that yields a calorimetric change and a fluorescent signal in response to cellular metabolic activity.

Assay protocol: Blood from a 50 year old male human was drawn and centrifuged at 1500 rpm for 15 minutes at room temperature. The buffy coat cells at the plasma-red blood cell interface were aspirated. Buffy coat cells (mainly lymphocyte cells) were then transferred into 15 ml centrifuge tubes containing 5 ml of RPMI-1640 medium+10% Fetal Bovine Serum (Gibco, Grand Island, N.Y.). Additional medium was added to the tubes to bring the volume up to 10 ml. The buffy coat suspension was then carefully layered on 5 ml of Histopaque (Sigma Chemical Co., St. Louis, Mo.) and centrifuged at 1500 rpm for 30 minutes at room temperature. The interface which is mostly PBMCs (peripheral mononuclear cells) was aspirated and transferred to a 15 ml conical centrifuge tube and, resuspended in 2 ml cold RPMI-1640 and brought up to 15 ml with cold RPMI-1640 medium. Cells were centrifuged at 1500 rpm for 10 minutes. The supernatant was then aspirated and discarded. The cell pellet was re-suspended in 1 ml of cold RPMI 1640 and brought up to 15 ml with RPMI medium. This step was repeated twice, except that in the last step, the cells were resuspended with 1 ml of cold RPMI-1640 medium and cell counts were performed with a hemocytometer according to the Sigma cell culture catalogue.

Pokewood mitogen was used as a control along with positive and negative controls. Negative control cells were killed with 70% methanol. Positive (+) control cells were incubated in RPMI medium (untreated). 20 ml of Alamar-Blue was added to the cells, and readings were taken after 24 hours, 48 hours, 72 hours, and 96 hours using a fluorimeter (excitation 544/transmission 590 nm).

Calculations were Performed Using the Following Formula:

$$\% \text{ treated cell viability} = \frac{\text{Peptide treated sample (adj. for negative control)}}{\text{Positive control (adj. for negative control)}} \times 100\%$$

Using the protocol described immediately above, about 100-150 peptides were screened for their stimulatory and/or inhibitory actions upon the growth of human leukocyte ("WBC") cells as compared to the growth of untreated positive control cells. The data in Table 8 below show that various selected FLAK peptides are stimulatory at low concentrations (0.1 to 1.0 µg/ml), whereas certain of the peptides become inhibitory (causing cell death) at higher concentrations. Several of the peptides (i.e. SEQ ID NOS:5, 143, and 160) are stimulatory (and/or proliferative) at all concentrations through 500 µg/ml.

The Alamar Blue stain used-in the protocol permeates both cell and nuclear membranes, and is metabolized in the mitochondria to cause the change in color. The resulting fluorometric response is therefore a result of total mitochondrial activity caused by cell stimulation and/or mitosis (cell proliferation). The increase in values (for treated cells, as a percent of values for untreated cells) with increased incubation time (120 hours vs. 48 hours) may be attributed to increased cell proliferation in addition to stimulation of cell metabolic activity caused by the peptide.

Table 8 presents viability data, as percent of untreated positive control, for human leukocytes (white blood cells, "WBC") in the presence of selected FLAK peptides. The table also shows for each of these peptides its toxicity (LD50 values) to human red blood cells (RBC) and to human fibroblast cells (WI38). Those certain peptides which are stimulatory to WBCs at low peptide concentrations (i.e. 10 µg/ml or less) and are inhibitory or toxic to WBCs at higher concentrations are also relatively more toxic to RBCs and to fibroblasts than those peptides which are stimulatory and not inhibitory to WBC growth even at concentrations as high as 500 µg/ml.

In limited experiments with other than the Alamar Blue protocol described above, it has been qualitatively determined that those peptides which cause stimulation and proliferation of leukocytes are active upon both the phagocytic and lyphocyte cell components of the mammalian lymphatic system. As such, certain of the stimulatory FLAK peptides which are relatively non-toxic to mammalian cells at therapeutic dose levels may be used as immunomodulators to treat humans or other mammals with compromised immune systems. Such treatment may be administered systemically in vivo or by extra-corporeal treatment of whole blood or blood components to be reinfused to the donor. Such therapy would serve to counteract immune deficiency in neutropenic patients caused by age, disease, or chemotherapy and would stimulate natural immune responses to prevent or combat pathogenic infections and growth of certain cancer cell lines or to enhance wound healing processes involving the lymphoid system. Table 9 is a more detailed example (with one peptide, SEQ ID NO:10) of the phenomenon showing the relationships of concentration and time as they effect stimulation, proliferation, and inhibition of the leukocytes.

TABLE 8

Human leukocyte (WBC) stimulation/proliferation & inhibition by selected FLAK peptides

| SEQ ID NO: | Peptide conc. P Number | 0.1 µg/ml 48 hours | 0.1 µg/ml 120 hours | 1 µg/ml 48 hours | 1 µg/ml 120 hours | 10 µg/ml 48 hours | 10 µg/ml 120 hours |
|---|---|---|---|---|---|---|---|
| 5 | 12 | 111 | 124 | 115 | 136 | 118 | 141 |
| 10 | 25 | 117 | 135 | 104 | 118 | 99 | 119 |
| 12 | 27 | 108 | 117 | 110 | 126 | 99 | 114 |
| 17 | 35 | 115 | 113 | 119 | 105 | 114 | 81 |
| 20 | 38 | 115 | 110 | 119 | 117 | 114 | 109 |
| 25 | 43 | 115 | 100 | 119 | 114 | 114 | 104 |
| 58 | 92 | 112 | 120 | 112 | 114 | 98 | 99 |
| 66 | 102 | 100 | 89 | 102 | 90 | 97 | 110 |
| 143 | 182 | 101 | 134 | 96 | 117 | 101 | 133 |
| 150 | 306 | 97 | 94 | 101 | 113 | 94 | 109 |

| SEQ ID NO: | Peptide conc. P Number | 100 µg/ml 48 hours | 100 µg/ml 120 hours | 500 µg/ml 48 hours | 500 µg/ml 120 hours | RBC toxicity LD50 | WI-38 toxicity LD50 |
|---|---|---|---|---|---|---|---|
| 5 | 12 | 116 | 151 | 101 | 119 | >1000 | 950 |
| 10 | 25 | 27 | 43 | 27 | 45 | 60 | 24 |
| 12 | 27 | 30 | 43 | 23 | 39 | 125 | 37 |
| 17 | 35 | 73 | 42 | 72 | 43 | 200 | 8 |
| 20 | 38 | 73 | 60 | 72 | 57 | 350 | 12 |
| 25 | 43 | 73 | 39 | 72 | 37 | 20 | 5 |
| 58 | 92 | 35 | 30 | 26 | 26 | 300 | 125 |
| 66 | 102 | 37 | 32 | 17 | 15 | 300 | 73 |
| 143 | 182 | 109 | 150 | 105 | 132 | >1000 | 660 |
| 150 | 306 | 109 | 140 | 112 | 140 | >1000 | 320 |

TABLE 9

Human leukocyte (WBC) stimulation/proliferation and inhibition by FLAK peptide SEQ ID NO: 10 (P25)

| Time of incubation | 0.1 µg/ml | 1 µg/ml | 10 µg/ml | 100 µg/ml | 500 µg/ml |
|---|---|---|---|---|---|
| 24 hours | 111 | 98 | 88 | 10 | 10 |
| 48 hours | 117 | 104 | 99 | 27 | 27 |
| 72 hours | 119 | 105 | 102 | 31 | 32 |
| 96 hours | 128 | 112 | 110 | 38 | 40 |
| 120 hours | 135 | 118 | 119 | 43 | 45 |

Note:
Number values are percent cell viability relative to control cells.

Example 4

Stimulation and Proliferation of Fibroblasts

The cyQUANT cell proliferation assay provides a convenient, rapid and sensitive procedure for determining the density of cells in culture. The assay has a linear detection range extending from 50 or fewer to at least 50,000 cells in 200 µl volumes using a single dye concentration. The assay is ideal for cell proliferation studies as well as for routine cell counts and can be used to monitor the adherence of cells to surfaces.

Procedure: Different cell lines were maintained with different medium according to the ATCC. Cells were trypsinized with 8 ml of Trypsin (0.25%, Fisher, Pittsburgh, Pa.). The cell suspension was centrifuged for 10 minutes at 100 rpm. The supernatant was removed and discarded without disturbing the cell pellet. A concentrated cell suspension was prepared in 1.0 ml of medium to obtain a density of about $10^5$ to $10^6$ cells/ml. The actual cell density was determined by counting the cells using a hemocytometer with the Trypan Blue method. Cell numbers were adjusted to obtain equal number of cells per 200 µl volume. Cells were plated with 0% FBS, 2.5% FBS, 5% FBS and 10% FBS. The plates were incubated at 37° C. for a time sufficient to allow the cells to attach. For long-term proliferation studies, 100 µl of medium was removed from each well each day and replaced with fresh medium.

At the desired time, the medium was removed from the adherent cells in a 96 well plate. These cells were already treated with test agents. The cells were frozen in the plate at −70° C. for 30 minutes. The cells were thawed at room temperature. CyQuant GR dry/Cell Lysis Buffer (200 µl) was added to each sample cell. The cells were incubated at room temperature for 15 minutes while protected from the light. Fluorescence was measured using fmax at 485-538 nm.

The above CyQuant protocol was used to examine possible peptide stimulation of fibroblasts. In the following Table 10, data are shown for selected peptides demonstrating their effect on human fibroblast cells (WI38). In the table, the substantial stimulatory and/or proliferative property of selected peptides, as a function of concentration is evident. The values are viability of treated cells expressed as percent (%) above or below positive control (untreated cells). Table 11 shows that the fibroblast stimulation and/or proliferation effect is enhanced for certain peptides in the presence of other growth factors. This is shown by the addition of Fetal Bovine Serum (FBS) to the medium. Negative values indicate inhibitory action of the peptide, especially at concentrations above 10 µg/ml.

TABLE 10

Human fibroblast (WI-38) cell stimulation by selected FLAK peptides

| SEQ ID NO: | P Number | % FBS in serum | Peptide concentration | | | |
|---|---|---|---|---|---|---|
| | | | 0.1 µg/ml | 1 µg/ml | 10 µg/ml | 100 µg/ml |
| 2 | 2 | 0 | −27 | −3 | 27 | −82 |
| | | 2.5 | 26 | 57 | 23 | −66 |
| 4 | 11 | 0 | 19 | 34 | 50 | −40 |
| | | 2.5 | 50 | 52 | 62 | 14 |
| 6 | 13 | 0 | 76 | 68 | 93 | 95 |
| 8 | 23 | 0 | 21 | 78 | 10 | −48 |
| | | 2.5 | 16 | 23 | 58 | 75 |
| 10 | 25 | 0 | 50 | 59 | 29 | −27 |
| 14 | 27C | 0 | 60 | 85 | 90 | 63 |
| 15 | 30 | 0 | 60 | 75 | 20 | 35 |
| 17 | 35 | 0 | 45 | 70 | 65 | 50 |
| 20 | 38 | 0 | 44 | 22 | 75 | 53 |
| 35 | 55 | 0 | 1 | 12 | 30 | 76 |
| 5 | 12 | 0 (24 h inc) | 93 | 90 | 116 | 65 |
| 58 | 92 | 0 (24 h inc) | 109 | 114 | 132 | 36 |
| 71 | 107 | 0 | 18 | 27 | 26 | 24 |
| 80 | 118 | 0 | 12 | −4 | −7 | −1 |
| | | 0 (24 h inc) | 24 | 55 | 48 | 24 |
| | | 3 | 61 | 70 | 68 | 72 |
| 126 | 165 | 0 | 51 | 77 | 115 | 50 |

Note:
Number values are percent cell viability above or below control.

Incubations were 48 hours unless otherwise indicated. SEQ ID NOS:5 and 71 are not FLAK peptides.

TABLE 11

Effect of growth factors on human fibroblast (WI38) cell stimulation

| SEQ ID NO: | P Number | % FBS in serum | Peptide concentration | | | |
|---|---|---|---|---|---|---|
| | | | 0.1 µg/ml | 1 µg/ml | 10 µg/ml | 100 µg/ml |
| 2 | 2 | 0 | −27 | −3 | 27 | −82 |
| | | 2.5 | 26 | 57 | 23 | −66 |
| 4 | 11 | 0 | 19 | 34 | 50 | −40 |
| | | 2.5 | 50 | 52 | 62 | 14 |
| 8 | 23 | 0 | 21 | 78 | 10 | −48 |
| | | 2.5 | 16 | 23 | 58 | 75 |
| 80 | 118 | 0 | 12 | −4 | −7 | −1 |
| | | 3 | 61 | 70 | 68 | 72 |

Note:
Number values are percent cell viability above or below control.

Example 5

Toxicity Assay—Red Blood Cell (RBC) Hemolysis, and Leukocyte (WBC) and Fibroblast (WI38) Inhibition Table 12 below summarizes the RBC, WBC, and WI38 toxicity data for typical FLAK peptides. The three RBC, WBC, and WI38 values (LD50) are generally consistent directional indicators of peptide toxicity. In choosing a peptide for possible treatment of a given indication it is important to match the therapeutic activity and specificity of the peptide with its possible toxic properties. The SEQ ID NO:5 peptide is not a FLAK peptide, but rather it is SB-37, a close homolog of Cecropin B. It has previously been shown not to be as active as the FLAK peptides as an antibacterial agent, but to possess wound healing properties as demonstrated in vivo in a rat model. This probably results from its stimulatory and proliferative effects on both mammalian leukocytes and fibroblasts.

The protocols for WBC and WI38 stimulation have been discussed above. The RBC protocol follows Table 12.

TABLE 12

In vitro toxicity of selected FLAK peptides on red blood cells (RBC), human leukocytes (WBC), and human fibroblasts (WI38)

| SEQ ID NO: | P Number | RBC LD50 µg/ml | WBC LD50 µg/ml | WI38 LD50 µg/ml |
|---|---|---|---|---|
| 5 | 12 | >1000 | >500 | 60 |
| 10 | 25 | 60 | 79 | 60 |
| 11 | 26 | 900 | 185 | 100 |
| 12 | 27 | 125 | 78 | 60 |
| 16 | 34 | 200 | 77 | 200 |
| 17 | 35 | 200 | 64 | 25 |
| 20 | 38 | 350 | 160 | 100 |
| 25 | 43 | 20 | 70 | 25 |
| 30 | 48 | 130 | 78 | 70 |
| 35 | 55 | 30 | 80 | 28 |
| 58 | 92 | 300 | 51 | 400 |
| 66 | 102 | 300 | 115 | 45 |

RBC protocol is as follows. Well positions of each dilution and untreated control are recorded on the lid of a 96-well plate. When the cells were confluent, the media is removed, and replaced with freshly prepared sample dilutions to a final volume of 200 µl. Test agent was added into designed wells of the 96-well plate. The 200 µl fresh medium was added to positive control wells; and 200 µl of 70% ethanol was added to negative control wells. The plate was incubated overnight at 37° C., 5% $CO_2$, and at least 90% humidity. Room temperature AlamarBlue solution (20 µl) was added to all wells. The plates were read spectrofluorometrically (excitation 544 nm, emission 590 nm). The plates were incubated for 3 hours at 37° C., 5% $CO_2$, and at least 90% humidity. The plates were read again at 3 and 24 hours incubation. The LD50 endpoint was determined from the graph by reading from where the 50 percent point intercepts the Dose Response Curve to the concentration along the x-axis. That concentration is the LD50 value. The LD50 value for test agents within a single test agent class can be used to rank-order their relative toxicities or to correlate with in vivo data.

This hemolytic assay is based upon that presented in *Journal of Peptide Research* 53: 82-90 (1999). Preparation of all media, stock solutions and dilutions were performed in a laminar flow hood to minimize or prevent contamination. All procedures were performed according to safety protocols pertaining to the handling and disposal of human body fluids.

Red blood cells (RBCs) were washed three times with PBS (35 mM phosphate buffer 0.15 M NaCl, pH 7.0). RBCs suspended in PBS (0.4% (v/v); about 10 ml per 15 peptides) were prepared. Suspensions (100 µl) were aliquoted to each sample and control tube. Serially diluted peptide solutions (100 µl) were pipetted into the sample tubes. Negative control tubes contained 100 µl PBS; positive control tubes contained 100 µl 1% Triton-X100 detergent. All tubes were incubated for 1 hour at 37° C. The tubes were removed from the incubator and centrifuged at 1000 g for 5 minutes. Supernatant (100 µl) was pipetted to a 96-well polyvinyl chloride plate. The absorbance at 414 nm ($A_{414}$) was measured, and used to calculate the percent hemolysis according to the following formula.

$$\frac{(A_{414} \text{ in peptide solution} - A_{414} \text{ in } PBS)}{(A_{414} \text{ in Triton-}X100 - A_{414} \text{ in } PBS)} \times 100\%$$

Percent hemolysis is plotted against peptide concentration, and the concentration at which 50% hemolysis is determined ($LD_{50}$). The following Table 13 details the results of the hemolytic assay using the peptides discussed herein.

TABLE 13

| Peptide name | SEQ ID NO: | P Number | $LD_{50}$ µg/mL |
|---|---|---|---|
| Hecate AC #1010 | 1 | 1 | 100 |
| Hecate AM | 2 | 2 | 10 |
| SB-37 AC #1018 | 3 | 5 | > |
| Shiva 10 AM | 4 | 11 | 76 |
| SB-37 AM | 5 | 12 | > |
| Shiva 10 AC #1015 | 6 | 13 | 50 |
| Magainin 2 | 7 | 16 | 550 |
| FLAK01 AM | 8 | 23 | 300 |
| FLAK03 AM | 9 | 24 | 10 |
| FLAK04 AM | 10 | 25 | 16 |
| FLAK05 AM | 11 | 26 | 90 |
| FLAK06 AM | 12 | 27 | 125 |
| FLAK06 AC | 13 | 27B | 700 |
| FLAK06 R-AC | 14 | 27C | 250 |
| KALV | 15 | 30 | 150 |
| FLAK 17 AM | 16 | 34 | 200 |
| FLAK 26 AM | 17 | 35 | 200 |
| FLAK 25 AM | 18 | 36 | 85 |
| Hecate 2DAc | 19 | 37 | 30 |
| FLAK43 AM | 20 | 38 | 350 |
| FLAK44 AM | 21 | 39 | > |
| FLAK62 AM | 22 | 40 | > |
| FLAK 06R-AM | 23 | 41 | 40 |
| MSI-78 AM | 24 | 42 | 300 |
| FLAK50 | 25 | 43 | 20 |
| FLAK51 | 26 | 44 | 90 |
| FLAK57 | 27 | 45 | 700 |
| FLAK71 | 28 | 46 | 900 |
| FLAK77 | 29 | 47 | > |
| FLAK50V | 30 | 48 | 200 |
| FLAK50F | 31 | 49 | 225 |
| FLAK26V AM | 32 | 50 | 420 |
| CAME-15 | 33 | 53 | 20 |
| FLAK50C | 34 | 54 | 250 |
| FLAK50D | 35 | 55 | 20 |
| FLAK50E | 36 | 56 | 600 |
| FLAK80 | 37 | 57 | > |
| FLAK81 | 38 | 58 | > |
| FLAK82 | 39 | 59 | 1000 |
| FLAK83M | 40 | 60 | > |
| FLAK 26 Ac | 41 | 61 | 390 |
| Indolicidin | 42 | 63 | 375 |
| FLAK 17 C | 43 | 64 | 6 |
| FLAK 50H | 44 | 65 | 950 |
| FLAK 50G | 45 | 66 | 600 |
| Shiva deriv P69 + KWKL | 46 | 70 | 80 |
| Shiva 10 (1-18_AC | 47 | 71 | > |
| Shiva 10 peptide 71 + KWKL | 48 | 72 | 110 |
| CA(1-7)Shiva10(1-16) | 49 | 73 | 90 |
| FLAK 54 | 50 | 74 | > |
| FLAK 56 | 51 | 75 | 750 |
| FLAK 58 | 52 | 76 | > |
| FLAK 72 | 53 | 77 | > |
| FLAK 75 | 54 | 79 | > |
| Shiva 10 (1-16) Ac | 55 | 80 | 900 |
| CA(1-7)Shiva10(1-16)-COOH | 56 | 81 | 8 |
| Indolocidin-ac | 57 | 91 | 40 |
| FLAK50B | 58 | 92 | 300 |
| FLAK50J | 59 | 93 | > |
| FLAK50I | 60 | 94 | 350 |
| FLAK50K | 61 | 95 | > |
| FLAK50L | 62 | 96 | > |

TABLE 13-continued

| Peptide name | SEQ ID NO: | P Number | LD$_{50}$ µg/mL |
|---|---|---|---|
| Shiva-11 | 63 | 98 | 60 |
| Shiva 11[(1-16)ME(2-9)]-COOH | 64 | 99 | 25 |
| FLAK 50N | 65 | 101 | 550 |
| FLAK 50O | 66 | 102 | 500 |
| FLAK 50P | 67 | 103 | 650 |
| CA(1-&Hecate(11/23) | 68 | 104 | 70 |
| PYL-ME | 69 | 105 | ND |
| FLAG26-D1 | 70 | 106 | > |
| Vishnu3 | 71 | 107 | > |
| Melittin | 72 | 108 | <1 |
| FLAK26-D2 | 73 | 109 | > |
| FLAG26-D3 | 74 | 110 | > |
| FLAK50 Q1 | 75 | 111 | 60 |
| FLAK50 Q2 | 76 | 112 | > |
| FLAK50 Q3 | 77 | 113 | 1000 |
| FLAK50 Q4 | 78 | 114 | > |
| FLAK50 Q5 | 79 | 117 | > |
| FLAK50 Q6 | 80 | 118 | 700 |
| FLAK50 Q7 | 81 | 119 | 400 |
| FLAK50 Q8 | 82 | 120 | > |
| FLAK50 Q9 | 83 | 121 | > |
| FLAK50 Q10 | 84 | 122 | > |
| FLAK50 T1 | 85 | 123 | 1000 |
| FLAK50 T2 | 86 | 124 | 55 |
| FLAK50 T3 | 87 | 125 | > |
| FLAK50 T4 | 88 | 126 | > |
| FLAK50 T5 | 89 | 127 | > |
| FLAK90 | 90 | 128 | > |
| FLAK91 | 91 | 129 | > |
| FLAK92 | 92 | 130 | > |
| FLAK93 | 93 | 131 | > |
| FLAK50 Z1 | 94 | 132 | > |
| FLAK50 Z2 | 95 | 133 | > |
| FLAK50 Z3 | 96 | 134 | > |
| FLAK50 Z4 | 97 | 135 | 900 |
| FLAK50 Z5 | 98 | 136 | > |
| FLAK50 Z6 | 99 | 137 | > |
| FLAK50 Z7 | 100 | 138 | 20 |
| FLAK50 Z8 | 101 | 139 | > |
| FLAK50 Z9 | 102 | 140 | > |
| FLAK94 | 103 | 141 | 900 |
| FLAK93B | 104 | 142 | 900 |
| FLAK50 Z10 | 105 | 143 | > |
| FLAK96 | 106 | 144 | 600 |
| FLAK97 | 107 | 145 | > |
| FLAK98 | 108 | 146 | 180 |
| FKRLA | 109 | 147 | 300 |
| FLAK91B | 110 | 148 | > |
| FLAK92B | 111 | 149 | > |
| FLAK99 | 112 | 150 | 650 |
| FLAK50T6 | 113 | 151 | > |
| FLAK50T7 | 114 | 152 | 880 |
| FLAK95 | 115 | 153 | 800 |
| FLAK50T8 | 116 | 154 | 450 |
| FLAK50T9 | 117 | 155 | > |
| FLAK100-CO2H | 118 | 156 | 10 |
| FAGVL | 119 | 157 | 850 |
| Modelin-5 | 120 | 159 | ND |
| Modelin-5-CO2H | 121 | 160 | > |
| FLAK120 | 126 | 165 | 350 |
| FLAK121 | 127 | 166 | > |
| FLAK96B | 128 | 167 | 200 |
| FLAK96G | 129 | 168 | 600 |
| FLAK96F | 130 | 169 | > |
| FLAK96C | 131 | 170 | > |
| FLAK96D | 132 | 171 | 550 |
| Modelin-8D | 135 | 174 | > |
| Modelin-8E | 136 | 175 | > |
| Flak 96 | 137 | 176 | > |
| Flak 96I | 138 | 177 | 400 |
| Flak 96J | 139 | 178 | > |
| Flak 96L | 140 | 179 | 850 |
| FLAK-120G | 141 | 180 | > |
| FLAK-120D | 142 | 181 | > |
| FLAK-120C | 143 | 182 | > |
| FLAK-120B | 144 | 183 | > |
| FLAK-120F | 145 | 184 | 850 |
| Magainin2wisc | 146 | 300 | 250 |
| D2A21 | 147 | 301 | 10 |
| KSL-1 | 148 | 302 | > |
| KSL-7 | 149 | 303 | 500 |
| LSB-37 | 150 | 306 | > |
| Anubis-2 | 151 | 307 | > |
| FLAK17CV | 152 | 501 | 15 |
| FLAK50Q1V | 153 | 502 | 100 |
| D2A21V | 154 | 503 | 20 |
| FLAK25AMV | 155 | 504 | 70 |
| FLAK43AMV | 156 | 505 | 620 |
| FLAK50DV | 157 | 506 | 120 |
| HECATE AMV | 158 | 507 | 20 |
| HECATE ACV | 159 | 508 | 70 |
| FLAK04AMV | 160 | 509 | 40 |
| FLAK03AMV | 161 | 510 | 10 |
| D-Shiva 10 AC | 162 | 67 | 40 |
| Shiva 11 AC | 163 | 100 | > |
| Shiva 10 (1-18)AM | 164 | 69 | 900 |

Note:
>indicates greater than 1000;
ND = not determined.

Example 6

Effects of Valine Substitution

Changing a peptide sequence where the first amino acid is valine, and particularly when the first amino acid is changed from phenylalanine to valine, can lead to desirable properties. The red blood cell and fibroblast cell (WI38) toxicity can be decreased, while not significantly decreasing other desirable properties. Table 14 below shows numerous examples (14) of reducing the indicated toxicity of a peptide as seen from increase in viability of both red blood cells and fibroblast cells when treated with peptide. LD50 values are in µg/ml.

TABLE 14

| SEQ. ID NO: | P No. | Sequence | Hemolysis RBC LD50 | WI-38 LD50 |
|---|---|---|---|---|
| 2 | 2 | FALALKALKKALKKLKKALKKAL-NH2 | 12 | 66 |
| 15 | 30 | VALALKALKKALKKLKKALKKAL-NH2 | 150 | 93 |
| 17 | 35 | FAKKLAKLAKKLAKLAL-NH2 | 150 | 25 |

TABLE 14-continued

| SEQ. ID NO: | P No. | Sequence | Hemolysis RBC LD50 | WI-38 LD50 |
|---|---|---|---|---|
| 32 | 50 | VAKKLAKLAKKLAKLAL-NH2 | 420 | 45 |
| 25 | 43 | FAKLLAKLAKKLL-NH2 | 20 | 25 |
| 30 | 48 | VAKLLAKLAKKLL-NH2 | 130 | 160 |
| 86 | 124 | FAKLLAKLAKKVL-NH2 | 55 | 21 |
| 116 | 154 | VAKLLAKLAKKVL-NH2 | 870 | 110 |
| 126 | 165 | FALALKALKKL-NH2 | 350 | 850 |
| 141 | 180 | VALALKALKKL-NH2 | 850 | 1000 |
| 43 | 64 | FAKALKALLKALKAL-NH2 | 6 | 37 |
| 152 | 501 | VAKALKALLKALKAL-NH2 | 15 | 26 |
| 75 | 111 | FAKFLAKFLKKAL-NH2 | 5 | 25 |
| 153 | 502 | VAKFLAKFLKKAL-NH2 | 100 | 64 |
| 147 | 301 | FAKKFAKKFKKFAKKFAKFAFAF-NH2 | 10 | 66 |
| 154 | 503 | VAKKFAKKFKKFAKKFAKFAFAF-NH2 | 20 | 150 |
| 18 | 36 | FAKKLAKLAKKLAKLALAL-NH2 | 12 | 19 |
| 155 | 504 | VAKKLAKLAKKLAKLALAL-NH2 | 70 | 110 |
| 20 | 38 | FAKKLAKLAKKLLAL-NH2 | 350 | 100 |
| 156 | 505 | VAKKLAKLAKKLLAL-NH2 | 620 | 85 |
| 35 | 55 | FAKLLAKALKKLL-NH2 | 20 | 32 |
| 157 | 506 | VAKLLAKALKKLL-NH2 | 120 | 75 |
| 1 | 1 | FALALKALKKALKKLKKALKKAL-COOH | 20 | 27 |
| 159 | 508 | VALALKALKKALKKLKKALKKAL-COOH | 70 | 190 |
| 10 | 25 | FALALKALKKLAKKLKKLAKKAL-NH2 | 16 | 24 |
| 160 | 509 | VALALKALKKLAKKLKKLAKKAL-NH2 | 40 | 95 |
| 9 | 24 | FALALKALKKLLKKLKKLAKKAL-NH2 | 10 | 55 |
| 161 | 510 | VALALKALKKLLKKLKKLAKKAL-NH2 | 10 | 77 |

Although the effects of reduction of toxicity to mammalian cells by valine substitution is accompanied by modest reductions of therapeutic activity against microbial pathogens and cancer cells, there are some cases in which the valine substitution results in a desirable increase in therapeutic activity. This can be seen in the following Table 15 where it is shown that the valine substitution in some cases has increased the peptide's activity against the gram negative bacterium *Pseudomonas*.

Hemolysis and WI38 values represent LD50 values. P. aerug values represent MIC values in µg/mL against *Pseudomonas aeruginosa* ATCC accession number 9027.

TABLE 15

| SEQ ID NO: | P No. | Sequence | Hemolysis | WI38 | P. aerug |
|---|---|---|---|---|---|
| 17 | 35 | FAKKLAKLAKKLAKLAL | 100 | 25 | 200 |
| 32 | 50 | VAKKLAKLAKKLAKLAL | 420 | 45 | 15 |
| 25 | 43 | FAKLLAKLAKKLL | 20 | 25 | 100 |
| 30 | 48 | VAKLLAKLAKKLL | 200 | 160 | 5 |

TABLE 15-continued

| SEQ ID NO: | P No. | Sequence | Hemolysis | WI38 | P. aerug |
|---|---|---|---|---|---|
| 86 | 124 | FAKLLAKLAKKVL | 300 | 21 | 100 |
| 116 | 154 | VAKLLAKLAKKVL | 450 | 110 | 100 |

Example 7

Preferred Peptides

Preferred peptides can be selected from the above described experimental data. Preferred antimicrobial peptides for gram positive or gram negative bacteria can be selected as having MIC values of less than or equal to about 10 µg/ml, or as having MBC values of less than or equal to about 25 µg/ml. Preferred antifungal peptides can be selected as having MIC or MBC values of less than or equal to about 25 µg/ml. Preferred anticancer peptides can be selected as having LD50 values of less than or equal to about 25 µg/ml.

The following Table 16 lists representative preferred peptides, where an 'X' indicates that the peptide is a preferred peptide for that column's property. The peptide's "length" is the number of amino acid residues in the sequence.

TABLE 16

| SEQ ID NO: | P-number | Length (AA) | Anti-bacterial | Anti-fungal | Anti-cancer |
|---|---|---|---|---|---|
| 1 | 1 | 23 | X | | X |
| 2 | 2 | 23 | X | X | X |
| 4 | 11 | 23 | X | | |
| 6 | 13 | 23 | X | | |
| 8 | 23 | 23 | X | | X |
| 10 | 25 | 23 | X | X | |
| 11 | 26 | 21 | X | X | X |
| 12 | 27 | 19 | X | X | |
| 13 | 27B | 19 | X | X | X |
| 14 | 27C | 19 | X | | |
| 15 | 30 | 23 | X | | |
| 16 | 34 | 16 | X | X | X |
| 17 | 35 | 17 | X | X | X |
| 18 | 36 | 19 | X | | X |
| 19 | 37 | 23 | X | | X |
| 20 | 38 | 15 | X | | X |
| 23 | 41 | 19 | X | | |
| 25 | 43 | 13 | X | X | X |
| 26 | 44 | 15 | X | | X |
| 27 | 45 | 14 | X | | |
| 28 | 46 | 15 | X | | |
| 29 | 47 | 12 | | | X |
| 30 | 48 | 13 | X | X | X |
| 31 | 49 | 12 | X | | |
| 32 | 50 | 17 | X | | X |
| 34 | 54 | 13 | X | | |
| 35 | 55 | 13 | X | X | X |
| 36 | 56 | 13 | X | | |
| 41 | 61 | 15 | X | | |
| 43 | 64 | 15 | X | | |
| 45 | 66 | 13 | X | | |
| 46 | 70 | 23 | X | | X |
| 50 | 74 | 13 | X | | |
| 51 | 75 | 13 | X | | X |
| 52 | 76 | 14 | X | | |
| 55 | 80 | 23 | X | | |
| 56 | 81 | 23 | X | | X |
| 57 | 91 | 15 | X | | X |
| 58 | 92 | 13 | X | X | X |

TABLE 16-continued

| SEQ ID NO: | P-number | Length (AA) | Anti-bacterial | Anti-fungal | Anti-cancer |
|---|---|---|---|---|---|
| 60 | 94 | 13 | X | | X |
| 65 | 101 | 13 | X | | |
| 66 | 102 | 13 | X | X | |
| 67 | 103 | 12 | X | X | |
| 68 | 104 | 20 | X | | X |
| 74 | 110 | 12 | X | | |
| 75 | 111 | 13 | X | | X |
| 77 | 113 | 13 | X | | |
| 80 | 118 | 13 | X | X | |
| 81 | 119 | 14 | X | X | |
| 84 | 122 | 13 | X | | |
| 85 | 123 | 10 | | X | |
| 86 | 124 | 13 | X | X | X |
| 87 | 125 | 13 | X | | |
| 93 | 131 | 5 | X | | |
| 106 | 144 | 12 | X | X | |
| 108 | 146 | 13 | X | X | |
| 112 | 150 | 17 | X | | |
| 115 | 153 | 17 | X | X | |
| 116 | 154 | 13 | | X | |
| 126 | 165 | 11 | X | X | |
| 128 | 167 | 12 | X | X | |
| 131 | 170 | 10 | | X | |
| 143 | 182 | 10 | | X | |
| 152 | 501 | 15 | | | X |
| 162 | 67 | 23 | X | | X |
| 163 | 100 | 13 | X | X | |
| 164 | 69 | 23 | X | | |
| 165 | 97 | 13 | X | X | |

Preferred peptides for stimulation and proliferation can also be selected. The following Table 17 lists representative preferred peptides, where an 'X' indicates that the peptide is a preferred peptide for that column's property. Peptides which are stimulatory for leukocytes at 0.1 µg/ml to 1.0 µg/ml concentration are preferred, as at this concentration the peptides are not toxic to red blood cells, WI-38 fibroblasts, or to human leukocytes. Peptides which are stimulatory for fibroblasts at 0.1 µg/ml to 1.0 µg/ml are preferred, as at this concentration the peptides are not toxic.

TABLE 17

Preferred peptides for leukocyte and fibroblast stimulation/proliferation

| SEQ ID NO: | P-number | Length | Leukocyte | Fibroblast |
|---|---|---|---|---|
| 1 | 29 | 23 | X | X |
| 2 | 2 | 23 | X | X |
| 5 | 12 | 38 | X | X |
| 6 | 13 | 23 | X | X |
| 8 | 23 | 23 | X | X |
| 10 | 25 | 23 | X | X |
| 11 | 26 | 21 | X | X |
| 12 | 27 | 19 | X | X |
| 13 | 27B | 19 | X | X |
| 14 | 27C | 19 | X | X |
| 15 | 30 | 23 | X | X |

TABLE 17-continued

Preferred peptides for leukocyte and fibroblast stimulation/proliferation

| SEQ ID NO: | P-number | Length | Leukocyte | Fibroblast |
|---|---|---|---|---|
| 16 | 34 | 16 | X | X |
| 17 | 35 | 17 | X | X |
| 20 | 38 | 15 |   | X |
| 27 | 45 | 14 |   | X |
| 28 | 46 | 15 |   | X |
| 30 | 48 | 13 |   | X |
| 32 | 50 | 17 |   | X |
| 34 | 54 | 13 | X |   |
| 45 | 66 | 13 | X | X |
| 46 | 70 | 23 | X | X |
| 50 | 74 | 13 | X | X |
| 51 | 75 | 13 | X | X |
| 55 | 80 | 23 |   | X |
| 56 | 81 | 23 |   | X |
| 57 | 91 | 15 | X | X |
| 58 | 92 | 13 | X | X |
| 59 | 93 | 13 |   | X |
| 60 | 94 | 13 |   | X |
| 61 | 95 | 13 | X | X |
| 65 | 101 | 13 |   | X |
| 66 | 102 | 13 |   | X |
| 71 | 107 | 19 | X | X |
| 74 | 110 | 12 |   | X |
| 75 | 111 | 13 |   | X |
| 77 | 113 | 13 |   | X |
| 80 | 118 | 13 |   | X |
| 81 | 119 | 14 |   | X |
| 87 | 125 | 13 | X | X |
| 90 | 128 | 5 | X | X |
| 91 | 129 | 5 |   | X |
| 92 | 130 | 5 |   | X |
| 115 | 153 | 17 |   | X |
| 116 | 154 | 13 | X |   |
| 126 | 165 | 11 |   | X |
| 127 | 166 | 11 |   | X |
| 129 | 168 | 6 | X | X |
| 132 | 171 | 11 |   | X |
| 137 | 176 | 11 | X |   |
| 138 | 177 | 12 | X |   |
| 139 | 178 | 11 | X | X |
| 140 | 179 | 11 | X | X |
| 141 | 180 | 11 | X | X |
| 142 | 181 | 10 | X | X |
| 143 | 182 | 10 | X | X |
| 144 | 183 | 5 | X | X |
| 145 | 184 | 5 | X | X |
| 159 | 508 | 23 | X | X |
| 162 | 67 | 23 | X | X |
| 164 | 69 | 18 |   | X |

Example 8

Synergistic Effects with Lysozyme

Synergy between lytic peptides and lysozyme was assayed. Sterilized milk was inoculated with bacteria to $5 \times 10^5$ per ml. Peptide Shiva-10 (SEQ ID NO:4) was added to 10 µg/ml, and chicken lysozyme was added to 1 mg/ml. The percent killing of bacteria was determined.

TABLE 18

|   | Staph. aureus | Pseud. aeruginosa |
|---|---|---|
| Peptide and lysozyme | 0% | 100% |
| Peptide | 0% | 0% |
| Lysozyme | 0% | 0% |

Synergy between cecropin SB-37 (SEQ ID NO:5) and lysozyme was determined against *Pseudomonas syringae* pv. *tabaci* (PSPT), *Pseudomonas solanacearum* (PS), *Erwinia caratovora subsp. carotova* (EC), and *Xanthomonas campestris* pv. *campestris* (XC). $LD_{50}$ (µM) values were determined.

TABLE 19

|   | SB-37 | Lysozyme | SB-37 and Lysozyme |
|---|---|---|---|
| PSPT | 5.20 | > | 0.19 |
| PS | 64.0 | > | 16.0 |
| EC | 1.48 | > | 0.44 |
| XC | 0.57 | > | 0.027 |

> indicates greater than 1000.

Synergy between Shiva-1 and lysozyme was determined. The percent viability of *Pseudomonas aeruginosa* was determined relative to blank controls. Lysozyme was used at the same molar concentration as the peptide.

TABLE 20

| Peptide concentration (µM) | SB-37 | Shiva-1 | Lysozyme (1×) | Shiva-1 and Lysozyme (1×) |
|---|---|---|---|---|
| 0 | 100 | 100 | 100 | 100 |
| 0.01 | 100 | 100 | 100 | 56.6 |
| 0.1 | 79.4 | 69.6 | 82.2 | 25.8 |
| 1 | 48.8 | 37.9 | 52.1 | 4.4 |
| 5 | 38.5 | 1.5 | 7.9 | 0.2 |
| 7.5 | 0.7 | 0.1 | 0.6 | 0 |
| 25 | 0 | 0 | 0.4 | 0 |

Synergy between Shiva-1 and lysozyme was determined. The percent viability of gram positive *S. intermedius* 19930, *S. intermedius* 20034, and *S. aureus* was determined relative to blank controls. Lysozyme was used at ten times the molar concentration as the peptide.

TABLE 21

*S. intermedius* 19930

| Peptide concentration (µM) | SB-37 | Shiva-1 | Lysozyme (10×) | Shiva-1 and Lysozyme (10×) |
|---|---|---|---|---|
| 0 | 100 | 100 | 100 | 100 |
| 0.01 | 100 | 100 | 100 | 100 |
| 0.1 | 94.7 | 81.8 | 100 | 79.2 |
| 0.5 | 69.4 | 65.0 | 81.3 | 65.1 |
| 1 | 42.5 | 42.1 | 53 | 43 |
| 5 | 36.1 | 35.2 | 49.5 | 17.2 |
| 10 | 5.6 | 1.2 | 34.4 | 1.1 |
| 50 | 0 | 0 | 22 | 0 |

TABLE 22

*S. intermedius* 20034

| Peptide concentration (µM) | SB-37 | Shiva-1 | Lysozyme (10×) | Shiva-1 and Lysozyme (10×) |
|---|---|---|---|---|
| 0 | 100 | 100 | 100 | 100 |
| 0.01 | 100 | 100 | 100 | 100 |
| 0.25 | 85.4 | 87.1 | 100 | 85.1 |
| 0.5 | 68.0 | 80 | 59.0 | 53.4 |
| 0.75 | 62.2 | 60.1 | 42.3 | 41.0 |
| 5 | 35.1 | 4.1 | 38.3 | 4.3 |
| 50 | 0 | 0 | 10.0 | 0 |

TABLE 23

_S. aureus_

| Peptide concentration (μM) | SB-37 | Shiva-1 | Lysozyme (10×) | Shiva-1 and Lysozyme (10×) |
|---|---|---|---|---|
| 0 | 100 | 100 | 100 | 100 |
| 0.01 | 100 | 100 | 100 | 100 |
| 0.1 | 100 | 100 | 100 | 100 |
| 0.5 | 81.0 | 50.1 | 100 | 100 |
| 1 | 47.5 | 24.4 | 51.0 | 31.2 |
| 5 | 31.8 | 15.9 | 18.4 | 8.2 |
| 10 | 5.6 | 4.5 | 13.3 | 4.5 |
| 50 | 1.9 | 1.6 | 9.5 | 1.4 |

Synergy experiments can also be performed using peptides in the presence of EDTA, which potentiates the peptides additively or synergistically.

Example 9

Synergistic Effects with Antibiotics

Synergy between peptide Shiva-10 (SEQ ID NO:4) and various antimicrobial agents was investigated against _Escherichia coli_ 25922. The following table illustrates the beneficial effects of combining the peptide with the agents, where the numbers are the minimum bactericidal concentration (MBC; μ/mL).

TABLE 24

| Agent | Without peptide | With peptide |
|---|---|---|
| Shiva-10 | 50 | n/a |
| Ticarcillin | 100 | 50 (15 μg/mL peptide) |
| Cefoperazone | 150 | 2.5 (15 μg/mL peptide) |
| Doxycycline | 5 | 1 (15 μg/mL peptide) |
| Neomycin | 100 | 5 (5 μg/mL peptide) |
| Amikacin | 150 | 50 (5 μg/mL peptide) |
| Tetracycline | 10 | 2.5 (5 μg/mL peptide) |

Synergy between peptide Shiva-10 (SEQ ID NO:4) and various antimicrobial agents was investigated against _Staph. aureus_ 29213. The following table illustrates the beneficial effects of combining the peptide with the agents, where the numbers are the minimum bactericidal concentration (MBC; μg/mL).

TABLE 25

| Agent | Without peptide | With 5 μg/mL peptide |
|---|---|---|
| Shiva-10 | 200 | n/a |
| Ampicillin | 5 | 2.5 |
| Ticarcillin | 25 | 15 |
| Cefoperazone | 10 | 2.5 |
| Tobramycin | 25 | 10 |
| Tetracycline | 10 | 1 |

Synergy between peptide FLAK 26AM (P35; SEQ ID NO:17) and various antimicrobial agents was investigated against _Staph. aureus_ 29213 MBC. The following table illustrates the beneficial effects of combining the peptide with the agents, where the numbers are the minimum bactericidal concentration (MBC; μg/mL). This experiment determined the peptide MBC in the absence of the antimicrobial agent, or in the presence of the indicated concentration of antimicrobial agent

TABLE 26

| Agent | MBC of peptide |
|---|---|
| FLAK 26AM alone | 50 |
| Vancomycin (1 ppm) | 32 |
| Cefoperazone (0.25 ppm) | 20 |

Synergy between doxacycline and various peptides was investigated against _P. aeruginosa_ 27853. The following table illustrates the beneficial effects of combining doxacycline and the peptides, where the numbers are the minimum bactericidal concentration (MBC; μ/mL). When combined with the peptides, the doxacycline was held at 10 ppm concentration.

TABLE 27

| Agent | Without doxacycline | With doxacycline |
|---|---|---|
| Doxacycline | n/a | 100 |
| SB-37 (P5; SEQ ID NO: 3) | 200 | 30 |
| FLAK 26AM (P35; SEQ ID NO: 17) | 50 | 32 |

Synergy between tetracycline and various peptides was investigated against _Escherichia coli_ 25922 MBC. The following table illustrates the beneficial effects of combining tetracycline and the peptides, where the numbers are the minimum bactericidal concentration (MBC; μg/mL). When combined with the peptides, the concentration of tetracycline was held at 1.5 ppm.

TABLE 28

| Agent | Without tetracycline | With tetracycline |
|---|---|---|
| Tetracycline | n/a | 10 |
| FLAK 06AM (P27; SEQ ID NO: 12) | 75 | 25 |
| FLAK 26AM (P35; SEQ ID NO: 17) | 50 | 20 |

Example 10

Synergistic Effects with Chemotherapy Agents

Other investigators have reported that lytic peptides which are inhibitory to cancer cells will act synergistically with conventional cancer chemotherapy drugs. The FLAK peptides are no exception. Table 29 below demonstrates for example that selected FLAK peptides are synergistic with Tamoxifen in the inhibition of the MCF7 line of breast cancer cells. Table 30 lists other more active anti-cancer peptide candidates for synergistic application with Tamoxifen or other cancer therapy drugs.

Tables 29 and 30 also show toxicity of the selected peptides against RBCs, WBCs, and WI38 cells. When used at very low non-toxic levels selected anti-cancer peptides can synergistically potentiate other chemotherapy agents to permit their effective use at substantially lower dose levels with consequently fewer side effects.

TABLE 29

Synergy of FLAK peptides with tamoxifen on MCF7 cells

|  |  | Active agent | | LD50 on MCF7 cells | |
|---|---|---|---|---|---|
| SEQ ID NO:<br>(P No.) | Agent | MCF7<br>LD50 µg/ml | Peptide<br>conc. µg/ml | Tamox.<br>conc. µg/ml | Total conc.<br>µg/ml |
|  | Tamoxifen | 20 | 0 | 20 | 20 |
| 164 (69) | Alone With Tamox. | 79 | 2.5 | 4.6 | 7.1 |
| 145 (184) | Alone With Tamox. | 240 | 10 | 4 | 14 |
| 121 (160) | Alone With Tamox. | 240 | 11 | 3.7 | 14.7 |
| 106 (144) | Alone With Tamox. | 310 | 35 | 7.7 | 42.7 |

TABLE 30

Other highly active peptide candidates for synergistic anti-cancer applications

| SEQ ID NO:<br>(P No.) | MCF7 LD50<br>µg/ml | RBC LD50<br>µg/ml | WI38 LD50<br>µg/ml | WBC LD50<br>µg/ml |
|---|---|---|---|---|
| 17 (35) | 9 | 200 | 25 | 25 |
| 32 (50) | 32 | 420 | 40 | 420 |
| 20 (38) | 17 | 350 | 100 | 54 |

Example 11

Synergistic Effects with Growth Factors

It has been shown above in Example 4 and Table 11 that certain of the FLAK peptides are synergistic with other mitogens or growth factors in the stimulatory and/or proliferative properties of the peptides.

Example 12

Activity Against Drug Resistant Strains

Peptides were assayed for their activity against tobramycin sensitive and resistant strains. As shown in the following Table 31, peptides P56 (SEQ ID NO:36), P74 (SEQ ID NO:50), and P125 (SEQ ID NO:87) showed enhanced activity against tobramycin resistant (tr) *Pseudomonas* ATCC 13096 than against tobramycin sensitive (ts) *Pseudomonas* ATCC 27853. The same three peptides showed enhanced activity against clinical tobramycin resistant strain 960890198-3c (Table 31).

TABLE 31

| Peptide | tr *Pseudomonas* 13096 | ts *Pseudomonas* 27853 |
|---|---|---|
| SEQ ID NO: 36 (P56) | 16 | 125 |
| SEQ ID NO: 50 (P74) | 16 | 125 |
| SEQ ID NO: 87 (P125) | 4 | 31 |

TABLE 32

| Peptide | tr *Pseudomonas*<br>960890198-3c | ts *Pseudomonas* 27853 |
|---|---|---|
| SEQ ID NO: 36 (P56) | >50 | 125 |
| SEQ ID NO: 50 (P74) | 25 | 125 |
| SEQ ID NO: 87 (P92) | 50 | 63 |

Example 13

Wound Healing

The inventive peptides can be used in compositions for topical or systemic delivery in wound healing applications. The compositions can be a liquid, cream, paste, or other pharmaceutically acceptable formulation. The compositions may contain other biologically active agents. The compositions may contain pharmaceutically acceptable carriers.

Those peptides preferred for wound healing, shown in Table 33 below, are peptides which were preferred for either, or or both, leukocyte or fibroblast stimulation.

TABLE 33

Preferred peptides for wound healing

| SEQ ID NO: | P No. |
|---|---|
| 1 | 1 |
| 2 | 2 |
| 5 | 12 |
| 6 | 13 |
| 8 | 23 |
| 10 | 25 |
| 11 | 26 |
| 12 | 27 |
| 13 | 27B |
| 14 | 27C |
| 15 | 30 |
| 16 | 34 |
| 17 | 35 |
| 20 | 38 |
| 27 | 45 |
| 28 | 46 |
| 30 | 48 |
| 32 | 50 |
| 34 | 54 |
| 45 | 66 |
| 46 | 70 |
| 50 | 74 |
| 51 | 75 |
| 55 | 80 |
| 56 | 81 |
| 57 | 91 |
| 58 | 92 |
| 59 | 93 |
| 60 | 94 |
| 61 | 95 |
| 65 | 101 |
| 66 | 102 |
| 71 | 107 |
| 74 | 110 |
| 75 | 111 |
| 77 | 113 |
| 80 | 118 |
| 81 | 119 |
| 87 | 125 |
| 90 | 128 |

TABLE 33-continued

Preferred peptides for wound healing

| SEQ ID NO: | P No. |
|---|---|
| 91 | 129 |
| 92 | 130 |
| 93 | 131 |
| 115 | 153 |
| 116 | 154 |
| 126 | 165 |
| 127 | 166 |
| 129 | 168 |
| 132 | 171 |
| 137 | 176 |
| 138 | 177 |
| 139 | 178 |
| 140 | 179 |
| 141 | 180 |
| 142 | 181 |
| 143 | 182 |
| 144 | 183 |
| 145 | 184 |
| 159 | 508 |
| 162 | 67 |
| 164 | 69 |

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention.

---

What is claimed is:

1. A skin care composition comprising:
   an isolated peptide and
   a carrier;
   wherein the peptide is SEQ ID NO:11, SEQ ID NO:12, SEQ ID NO:13, SEQ ID NO:14, SEQ ID NO:16, SEQ ID NO:17, SEQ ID NO:18, SEQ ID NO:20, SEQ ID NO:21, SEQ ID NO:22, SEQ ID NO:23, SEQ ID NO:25, SEQ ID NO:26, SEQ ID NO:27, SEQ ID NO:28, SEQ ID NO:29, SEQ ID NO:31, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:43, SEQ ID NO:44, SEQ ID NO:45, SEQ ID NO:46, SEQ ID NO:47, SEQ ID NO:48, SEQ ID NO:50, SEQ ID NO:51, SEQ ID NO:52, SEQ ID NO:53, SEQ ID NO:54, SEQ ID NO:58, SEQ ID NO:59, SEQ ID NO:60, SEQ ID NO:61, SEQ ID NO:62, SEQ ID NO:65, SEQ ID NO:66, SEQ ID NO:67, SEQ ID NO:70, SEQ ID NO:73, SEQ ID NO:74, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:85, SEQ ID NO:90, SEQ ID NO:91, SEQ ID NO:98, SEQ ID NO:103, SEQ ID NO:106, SEQ ID NO:107, SEQ ID NO:110, SEQ ID NO:113, SEQ ID NO:114, SEQ ID NO:115, SEQ ID NO:126, SEQ ID NO:127, SEQ ID NO:128, SEQ ID NO:129, SEQ ID NO:130, SEQ ID NO:131, SEQ ID NO:132, SEQ ID NO:137, SEQ ID NO:138, SEQ ID NO:139, SEQ ID NO:142, SEQ ID NO:143, SEQ ID NO:164, or SEQ ID NO:165.

2. The composition of claim 1, wherein the composition is an anti-acne composition that reduces or eliminates the appearance of acne lesions when applied to skin.

3. The composition of claim 1, wherein the composition is a liquid.

4. The composition of claim 1, wherein the composition is a cream, gel, ointment, lotion, or paste.

5. The composition of claim 1, wherein the concentration of the peptide in the composition is 0.01 μM to 500 μM.

6. The composition of claim 1, wherein the peptide is antimicrobial, antifungal, anticancer, or which promotes stimulation and/or proliferation of normal mammalian cells.

7. The composition of claim 1, wherein the peptide comprises at least 90% phenylalanine, leucine, alanine, and lysine residues.

8. The composition of claim 1, wherein the peptide comprises at least 95% phenylalanine, leucine, alanine, and lysine residues.

9. The composition of claim 1, wherein the peptide consists of phenylalanine, leucine, alanine, and lysine residues.

10. The composition of claim 1, wherein the peptide is further defined as SEQ ID NO:11, SEQ ID NO:12, SEQ ID NO:13, SEQ ID NO:14, SEQ ID NO:16, SEQ ID NO:17, SEQ ID NO:18, SEQ ID NO:20, SEQ ID NO:21, SEQ ID NO:22, SEQ ID NO:23, SEQ ID NO:25, SEQ ID NO:26, SEQ ID NO:27, SEQ ID NO:28, SEQ ID NO:29, SEQ ID NO:31, SEQ ID NO:34, SEQ ID NO:35, SEQ ID NO:36, SEQ ID NO:39, SEQ ID NO:40, SEQ ID NO:41, SEQ ID NO:43, SEQ ID NO:45, SEQ ID NO:46, SEQ ID NO:47, SEQ ID NO:48, SEQ ID NO:50, SEQ ID NO:51, SEQ ID NO:52, SEQ ID NO:53, SEQ ID NO:54, SEQ ID NO:58, SEQ ID NO:60, SEQ ID NO:61, SEQ ID NO:65, SEQ ID NO:66, SEQ ID NO:67, SEQ ID NO:70, SEQ ID NO:73, SEQ ID NO:74, SEQ ID NO:77, SEQ ID NO:78, SEQ ID NO:80, SEQ ID NO:81, SEQ ID NO:103, SEQ ID NO:106, SEQ ID NO:115, SEQ ID NO:126, SEQ ID NO:128, SEQ ID NO:131, SEQ ID NO:138, SEQ ID NO:164, or SEQ ID NO:165.

11. The composition of claim 1, wherein the peptide is further defined as SEQ ID NO:37, SEQ ID NO:38, SEQ ID NO:44, SEQ ID NO:59, SEQ ID NO:62, SEQ ID NO:76, SEQ ID NO:82, SEQ ID NO:83, SEQ ID NO:85, SEQ ID NO:90, SEQ ID NO:91, SEQ ID NO:98, SEQ ID NO:127, SEQ ID NO:129, SEQ ID NO:130, SEQ ID NO:132, SEQ ID NO:137, SEQ ID NO:139, SEQ ID NO:142, or SEQ ID NO:143.

12. The composition of claim 1, wherein the peptide is further defined as SEQ ID NO:79, SEQ ID NO:107, SEQ ID NO:110, SEQ ID NO:113, or SEQ ID NO:114.

13. A skin care composition comprising an isolated peptide of SEQ ID NO:68, SEQ ID NO:86, SEQ ID NO:87, SEQ ID NO:88, SEQ ID NO:89, SEQ ID NO:92, SEQ ID NO:140, or SEQ ID NO:153, and a carrier.

* * * * *

SEQUENCE LISTING

```
<160> NUMBER OF SEQ ID NOS: 165

<210> SEQ ID NO 1
<211> LENGTH: 23
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 1

Phe Ala Leu Ala Leu Lys Ala Leu Lys Lys Ala Leu Lys Lys Leu Lys
 1               5                  10                  15

Lys Ala Leu Lys Lys Ala Leu
            20

<210> SEQ ID NO 2
<211> LENGTH: 23
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (23)
<223> OTHER INFORMATION: AMIDATION

<400> SEQUENCE: 2

Phe Ala Leu Ala Leu Lys Ala Leu Lys Lys Ala Leu Lys Lys Leu Lys
 1               5                  10                  15

Lys Ala Leu Lys Lys Ala Leu
            20

<210> SEQ ID NO 3
<211> LENGTH: 38
<212> TYPE: PRT
<213> ORGANISM: ARTIFICIAL SEQUENCE
```

```
<220> FEATURE:
<223> OTHER INFORMATION: SYNTHETIC SEQUENCE

<400> SEQUENCE: 3

Met Pro Lys Trp Lys Val Phe Lys Lys Ile Glu Lys Val Gly Arg Asn
 1               5                  10                  15

Ile Arg Asn Gly Ile Val Lys Ala Gly Pro Ala Ile Ala Val Leu Gly
                20                  25                  30

Glu Ala Lys Ala Leu Gly
            35

<210> SEQ ID NO 4
<211> LENGTH: 23
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (23)
<223> OTHER INFORMATION: AMIDATION

<400> SEQUENCE: 4

Phe Ala Lys Lys Leu Ala Lys Lys Leu Lys Lys Leu Ala Lys Lys Leu
 1               5                  10                  15

Ala Lys Leu Ala Leu Ala Leu
            20

<210> SEQ ID NO 5
<211> LENGTH: 38
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (38)
<223> OTHER INFORMATION: AMIDATION

<400> SEQUENCE: 5

Met Pro Lys Trp Lys Val Phe Lys Lys Ile Glu Lys Val Gly Arg Asn
 1               5                  10                  15

Ile Arg Asn Gly Ile Val Lys Ala Gly Pro Ala Ile Ala Val Leu Gly
                20                  25                  30

Glu Ala Lys Ala Leu Gly
            35

<210> SEQ ID NO 6
<211> LENGTH: 23
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 6

Phe Ala Lys Lys Leu Ala Lys Lys Leu Lys Lys Leu Ala Lys Lys Leu
 1               5                  10                  15

Ala Lys Leu Ala Leu Ala Leu
            20

<210> SEQ ID NO 7
<211> LENGTH: 23
<212> TYPE: PRT
<213> ORGANISM: ARTIFICIAL SEQUENCE
<220> FEATURE:
```

<223> OTHER INFORMATION: SYNTHETIC SEQUENCE
<220> FEATURE:
<221> NAME/KEY: MOD_RES
<222> LOCATION: (23)
<223> OTHER INFORMATION: AMIDATION

<400> SEQUENCE: 7

Gly Ile Gly Lys Phe Leu His Ser Ala Lys Lys Phe Gly Lys Ala Phe
1               5                   10                  15

Val Gly Gly Ile Met Asn Ser
            20

<210> SEQ ID NO 8
<211> LENGTH: 23
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (23)
<223> OTHER INFORMATION: AMIDATION

<400> SEQUENCE: 8

Phe Ala Leu Ala Ala Lys Ala Leu Lys Lys Leu Ala Lys Lys Leu Lys
1               5                   10                  15

Lys Leu Ala Lys Lys Ala Leu
            20

<210> SEQ ID NO 9
<211> LENGTH: 23
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (23)
<223> OTHER INFORMATION: AMIDATION

<400> SEQUENCE: 9

Phe Ala Leu Ala Leu Lys Ala Leu Lys Lys Leu Leu Lys Lys Leu Lys
1               5                   10                  15

Lys Leu Ala Lys Lys Ala Leu
            20

<210> SEQ ID NO 10
<211> LENGTH: 23
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (23)
<223> OTHER INFORMATION: AMIDATION

<400> SEQUENCE: 10

Phe Ala Leu Ala Leu Lys Ala Leu Lys Lys Leu Ala Lys Lys Leu Lys
1               5                   10                  15

Lys Leu Ala Lys Lys Ala Leu
            20

<210> SEQ ID NO 11
<211> LENGTH: 21
<212> TYPE: PRT
<213> ORGANISM: ARTIFICIAL SEQUENCE

```
<220> FEATURE:
<223> OTHER INFORMATION: SYNTHETIC SEQUENCE
<220> FEATURE:
<221> NAME/KEY: MOD_RES
<222> LOCATION: (21)
<223> OTHER INFORMATION: AMIDATION

<400> SEQUENCE: 11

Phe Ala Leu Ala Lys Leu Ala Lys Lys Ala Lys Ala Lys Leu Lys Lys
 1               5                  10                  15

Ala Leu Lys Ala Leu
            20

<210> SEQ ID NO 12
<211> LENGTH: 19
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (19)
<223> OTHER INFORMATION: AMIDATION

<400> SEQUENCE: 12

Phe Ala Leu Ala Leu Lys Ala Leu Lys Lys Leu Lys Lys Ala Leu Lys
 1               5                  10                  15

Lys Ala Leu

<210> SEQ ID NO 13
<211> LENGTH: 19
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 13

Phe Ala Leu Ala Leu Lys Ala Leu Lys Lys Leu Lys Lys Ala Leu Lys
 1               5                  10                  15

Lys Ala Leu

<210> SEQ ID NO 14
<211> LENGTH: 19
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 14

Phe Ala Lys Lys Leu Ala Lys Lys Leu Lys Lys Leu Ala Lys Leu Ala
 1               5                  10                  15

Leu Ala Leu

<210> SEQ ID NO 15
<211> LENGTH: 23
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (23)
<223> OTHER INFORMATION: AMIDATION

<400> SEQUENCE: 15

Val Ala Leu Ala Leu Lys Ala Leu Lys Lys Ala Leu Lys Lys Leu Lys
```

Lys Ala Leu Lys Lys Ala Leu
            20

<210> SEQ ID NO 16
<211> LENGTH: 16
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (16)
<223> OTHER INFORMATION: AMIDATION

<400> SEQUENCE: 16

Phe Ala Leu Ala Leu Lys Lys Ala Leu Lys Ala Leu Lys Lys Ala Leu
1               5                   10                  15

<210> SEQ ID NO 17
<211> LENGTH: 17
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (17)
<223> OTHER INFORMATION: AMIDATION

<400> SEQUENCE: 17

Phe Ala Lys Lys Leu Ala Lys Leu Ala Lys Lys Leu Ala Lys Leu Ala
1               5                   10                  15
Leu

<210> SEQ ID NO 18
<211> LENGTH: 19
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (19)
<223> OTHER INFORMATION: AMIDATION

<400> SEQUENCE: 18

Phe Ala Lys Lys Leu Ala Lys Leu Ala Lys Lys Leu Ala Lys Leu Ala
1               5                   10                  15
Leu Ala Leu

<210> SEQ ID NO 19
<211> LENGTH: 23
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (13)..(14)
<223> OTHER INFORMATION: Xaa = D-lysine

<400> SEQUENCE: 19

Phe Ala Leu Ala Leu Lys Ala Leu Lys Lys Ala Leu Xaa Xaa Leu Lys
1               5                   10                  15
Lys Ala Leu Lys Lys Ala Leu
            20

```
<210> SEQ ID NO 20
<211> LENGTH: 15
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (15)
<223> OTHER INFORMATION: AMIDATION

<400> SEQUENCE: 20

Phe Ala Lys Lys Leu Ala Lys Leu Ala Lys Lys Leu Leu Ala Leu
 1               5                  10                  15

<210> SEQ ID NO 21
<211> LENGTH: 15
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (15)
<223> OTHER INFORMATION: AMIDATION

<400> SEQUENCE: 21

Phe Ala Lys Lys Leu Ala Lys Leu Ala Lys Lys Ala Leu Ala Leu
 1               5                  10                  15

<210> SEQ ID NO 22
<211> LENGTH: 15
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (15)
<223> OTHER INFORMATION: AMIDATION

<400> SEQUENCE: 22

Phe Ala Leu Ala Lys Lys Ala Leu Lys Lys Ala Lys Lys Ala Leu
 1               5                  10                  15

<210> SEQ ID NO 23
<211> LENGTH: 19
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (19)
<223> OTHER INFORMATION: AMIDATION

<400> SEQUENCE: 23

Phe Ala Lys Lys Leu Ala Lys Lys Leu Leu Lys Leu Ala Lys Leu Ala
 1               5                  10                  15

Leu Ala Lys

<210> SEQ ID NO 24
<211> LENGTH: 22
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
```

```
<221> NAME/KEY: MOD_RES
<222> LOCATION: (22)
<223> OTHER INFORMATION: AMIDATION

<400> SEQUENCE: 24

Gly Ile Gly Lys Phe Leu Lys Lys Ala Lys Lys Phe Gly Lys Ala Phe
 1               5                  10                  15
Val Lys Ile Leu Lys Lys
             20

<210> SEQ ID NO 25
<211> LENGTH: 13
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (13)
<223> OTHER INFORMATION: AMIDATION

<400> SEQUENCE: 25

Phe Ala Lys Leu Leu Ala Lys Leu Ala Lys Lys Leu Leu
 1               5                  10

<210> SEQ ID NO 26
<211> LENGTH: 15
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (15)
<223> OTHER INFORMATION: AMIDATION

<400> SEQUENCE: 26

Phe Ala Lys Lys Leu Ala Lys Leu Ala Leu Lys Leu Ala Lys Leu
 1               5                  10                  15

<210> SEQ ID NO 27
<211> LENGTH: 14
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (14)
<223> OTHER INFORMATION: AMIDATION

<400> SEQUENCE: 27

Phe Ala Lys Lys Leu Ala Lys Lys Leu Ala Lys Leu Ala Leu
 1               5                  10

<210> SEQ ID NO 28
<211> LENGTH: 15
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (15)
<223> OTHER INFORMATION: AMIDATION

<400> SEQUENCE: 28

Phe Ala Lys Lys Leu Lys Lys Leu Ala Lys Leu Ala Lys Lys Leu
 1               5                  10                  15
```

```
<210> SEQ ID NO 29
<211> LENGTH: 12
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (12)
<223> OTHER INFORMATION: AMIDATION

<400> SEQUENCE: 29

Phe Ala Lys Lys Ala Leu Lys Ala Leu Lys Lys Leu
 1               5                  10

<210> SEQ ID NO 30
<211> LENGTH: 13
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (13)
<223> OTHER INFORMATION: AMIDATION

<400> SEQUENCE: 30

Val Ala Lys Leu Leu Ala Lys Leu Ala Lys Lys Leu Leu
 1               5                  10

<210> SEQ ID NO 31
<211> LENGTH: 12
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (12)
<223> OTHER INFORMATION: AMIDATION

<400> SEQUENCE: 31

Phe Ala Lys Leu Leu Ala Lys Leu Ala Lys Lys Leu
 1               5                  10

<210> SEQ ID NO 32
<211> LENGTH: 17
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (17)
<223> OTHER INFORMATION: AMIDATION

<400> SEQUENCE: 32

Val Ala Lys Lys Leu Ala Lys Leu Ala Lys Lys Leu Ala Lys Leu Ala
 1               5                  10                  15

Leu

<210> SEQ ID NO 33
<211> LENGTH: 15
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
```

```
<221> NAME/KEY: MOD_RES
<222> LOCATION: (15)
<223> OTHER INFORMATION: AMIDATION

<400> SEQUENCE: 33

Lys Trp Lys Leu Phe Lys Lys Ile Gly Ala Val Leu Lys Val Leu
 1               5                  10                  15

<210> SEQ ID NO 34
<211> LENGTH: 13
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (13)
<223> OTHER INFORMATION: AMIDATION

<400> SEQUENCE: 34

Phe Ala Lys Leu Leu Ala Lys Leu Ala Lys Lys Ala Leu
 1               5                  10

<210> SEQ ID NO 35
<211> LENGTH: 13
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (13)
<223> OTHER INFORMATION: AMIDATION

<400> SEQUENCE: 35

Phe Ala Lys Leu Leu Ala Lys Ala Leu Lys Lys Leu Leu
 1               5                  10

<210> SEQ ID NO 36
<211> LENGTH: 13
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (13)
<223> OTHER INFORMATION: AMIDATION

<400> SEQUENCE: 36

Phe Ala Lys Leu Leu Lys Leu Ala Ala Lys Lys Leu Leu
 1               5                  10

<210> SEQ ID NO 37
<211> LENGTH: 10
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (10)
<223> OTHER INFORMATION: AMIDATION

<400> SEQUENCE: 37

Phe Ala Lys Leu Leu Ala Lys Lys Leu Leu
 1               5                  10

<210> SEQ ID NO 38
```

```
<211> LENGTH: 10
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (10)
<223> OTHER INFORMATION: AMIDATION

<400> SEQUENCE: 38

Phe Ala Lys Lys Leu Ala Lys Ala Leu Leu
 1               5                  10

<210> SEQ ID NO 39
<211> LENGTH: 10
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (10)
<223> OTHER INFORMATION: AMIDATION

<400> SEQUENCE: 39

Phe Ala Lys Lys Leu Ala Lys Lys Leu Leu
 1               5                  10

<210> SEQ ID NO 40
<211> LENGTH: 9
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (9)
<223> OTHER INFORMATION: AMIDATION

<400> SEQUENCE: 40

Phe Ala Lys Leu Ala Lys Lys Leu Leu
 1               5

<210> SEQ ID NO 41
<211> LENGTH: 17
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 41

Phe Ala Lys Lys Leu Ala Lys Leu Ala Lys Lys Leu Ala Lys Leu Ala
 1               5                  10                  15

Leu

<210> SEQ ID NO 42
<211> LENGTH: 13
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (13)
<223> OTHER INFORMATION: AMIDATION

<400> SEQUENCE: 42

Ile Leu Pro Trp Lys Trp Pro Trp Trp Pro Trp Arg Arg
```

<210> SEQ ID NO 43
<211> LENGTH: 15
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (15)
<223> OTHER INFORMATION: AMIDATION

<400> SEQUENCE: 43

Phe Ala Lys Ala Leu Lys Ala Leu Leu Lys Ala Leu Lys Ala Leu
 1               5                  10                  15

<210> SEQ ID NO 44
<211> LENGTH: 13
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (13)
<223> OTHER INFORMATION: AMIDATION

<400> SEQUENCE: 44

Phe Ala Lys Leu Leu Ala Lys Leu Ala Lys Ala Lys Leu
 1               5                  10

<210> SEQ ID NO 45
<211> LENGTH: 13
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (13)
<223> OTHER INFORMATION: AMIDATION

<400> SEQUENCE: 45

Phe Ala Lys Leu Leu Ala Lys Leu Ala Lys Leu Lys Leu
 1               5                  10

<210> SEQ ID NO 46
<211> LENGTH: 22
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (22)
<223> OTHER INFORMATION: AMIDATION

<400> SEQUENCE: 46

Phe Ala Lys Lys Leu Ala Lys Lys Leu Lys Lys Leu Ala Lys Lys Leu
 1               5                  10                  15

Ala Lys Lys Trp Lys Leu
                20

<210> SEQ ID NO 47
<211> LENGTH: 18
<212> TYPE: PRT
<213> ORGANISM: ARTIFICIAL SEQUENCE
<220> FEATURE:

```
<223> OTHER INFORMATION: SYNTHETIC SEQUENCE

<400> SEQUENCE: 47

Phe Ala Lys Lys Leu Ala Lys Lys Leu Lys Lys Leu Ala Lys Lys Leu
 1               5                  10                  15

Ala Lys

<210> SEQ ID NO 48
<211> LENGTH: 22
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 48

Phe Ala Lys Lys Leu Ala Lys Lys Leu Lys Lys Leu Ala Lys Lys Leu
 1               5                  10                  15

Ala Lys Lys Trp Lys Leu
             20

<210> SEQ ID NO 49
<211> LENGTH: 23
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (23)
<223> OTHER INFORMATION: AMIDATION

<400> SEQUENCE: 49

Lys Trp Lys Leu Phe Lys Lys Lys Thr Lys Leu Phe Lys Lys Phe Ala
 1               5                  10                  15

Lys Lys Leu Ala Lys Lys Leu
             20

<210> SEQ ID NO 50
<211> LENGTH: 13
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (13)
<223> OTHER INFORMATION: AMIDATION

<400> SEQUENCE: 50

Phe Ala Lys Lys Leu Ala Lys Lys Leu Ala Lys Ala Leu
 1               5                  10

<210> SEQ ID NO 51
<211> LENGTH: 13
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (13)
<223> OTHER INFORMATION: AMIDATION

<400> SEQUENCE: 51

Phe Ala Lys Lys Leu Ala Lys Lys Leu Ala Lys Leu Leu
 1               5                  10
```

<210> SEQ ID NO 52
<211> LENGTH: 14
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (14)
<223> OTHER INFORMATION: AMIDATION

<400> SEQUENCE: 52

Phe Ala Lys Lys Leu Ala Lys Lys Leu Ala Lys Ala Ala Leu
 1               5                  10

<210> SEQ ID NO 53
<211> LENGTH: 15
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (15)
<223> OTHER INFORMATION: AMIDATION

<400> SEQUENCE: 53

Phe Ala Lys Lys Leu Ala Lys Lys Ala Lys Leu Ala Lys Lys Leu
 1               5                  10                  15

<210> SEQ ID NO 54
<211> LENGTH: 12
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (12)
<223> OTHER INFORMATION: AMIDATION

<400> SEQUENCE: 54

Phe Ala Lys Lys Leu Lys Lys Leu Ala Lys Lys Leu
 1               5                  10

<210> SEQ ID NO 55
<211> LENGTH: 23
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 55

Lys Thr Lys Leu Phe Lys Lys Phe Ala Lys Lys Leu Ala Lys Leu
 1               5                  10                  15
Lys Lys Leu Ala Lys Lys Leu
                20

<210> SEQ ID NO 56
<211> LENGTH: 23
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 56

Lys Trp Lys Leu Phe Lys Lys Lys Thr Lys Leu Phe Lys Lys Phe Ala
 1               5                  10                  15

```
Lys Lys Leu Ala Lys Lys Leu
         20

<210> SEQ ID NO 57
<211> LENGTH: 13
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 57

Ile Leu Pro Trp Lys Trp Pro Trp Trp Pro Trp Arg Arg
 1               5                  10

<210> SEQ ID NO 58
<211> LENGTH: 13
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (13)
<223> OTHER INFORMATION: AMIDATION

<400> SEQUENCE: 58

Phe Ala Lys Ala Leu Ala Lys Leu Ala Lys Lys Leu Leu
 1               5                  10

<210> SEQ ID NO 59
<211> LENGTH: 13
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (13)
<223> OTHER INFORMATION: AMIDATION

<400> SEQUENCE: 59

Phe Ala Lys Leu Leu Ala Lys Leu Ala Lys Lys Ala Ala
 1               5                  10

<210> SEQ ID NO 60
<211> LENGTH: 13
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (13)
<223> OTHER INFORMATION: AMIDATION

<400> SEQUENCE: 60

Phe Ala Lys Leu Leu Ala Leu Ala Leu Lys Leu Lys Leu
 1               5                  10

<210> SEQ ID NO 61
<211> LENGTH: 13
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (13)
<223> OTHER INFORMATION: AMIDATION
```

```
<400> SEQUENCE: 61

Phe Ala Lys Leu Leu Ala Lys Leu Ala Lys Ala Lys Ala
 1               5                  10

<210> SEQ ID NO 62
<211> LENGTH: 13
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (13)
<223> OTHER INFORMATION: AMIDATION

<400> SEQUENCE: 62

Phe Ala Lys Leu Leu Ala Lys Leu Ala Lys Ala Lys Gly
 1               5                  10

<210> SEQ ID NO 63
<211> LENGTH: 31
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (31)
<223> OTHER INFORMATION: AMIDATION

<400> SEQUENCE: 63

Phe Ala Lys Lys Leu Ala Lys Lys Leu Lys Lys Leu Ala Lys Lys Leu
 1               5                  10                  15

Ala Lys Leu Ala Leu Ala Leu Lys Ala Leu Ala Leu Lys Ala Leu
                20                  25                  30

<210> SEQ ID NO 64
<211> LENGTH: 23
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 64

Phe Ala Lys Lys Leu Ala Lys Lys Leu Lys Lys Leu Ala Lys Lys Leu
 1               5                  10                  15

Ile Gly Ala Val Leu Lys Val
                20

<210> SEQ ID NO 65
<211> LENGTH: 13
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (13)
<223> OTHER INFORMATION: AMIDATION

<400> SEQUENCE: 65

Phe Ala Lys Leu Leu Ala Lys Ala Leu Lys Leu Lys Leu
 1               5                  10

<210> SEQ ID NO 66
<211> LENGTH: 13
```

```
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (13)
<223> OTHER INFORMATION: AMIDATION

<400> SEQUENCE: 66

Phe Ala Lys Leu Leu Ala Lys Ala Leu Lys Lys Ala Leu
 1               5                  10

<210> SEQ ID NO 67
<211> LENGTH: 12
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (12)
<223> OTHER INFORMATION: AMIDATION

<400> SEQUENCE: 67

Phe Ala Lys Leu Leu Ala Lys Ala Leu Lys Lys Leu
 1               5                  10

<210> SEQ ID NO 68
<211> LENGTH: 20
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (20)
<223> OTHER INFORMATION: AMIDATION

<400> SEQUENCE: 68

Lys Trp Lys Leu Phe Lys Lys Ala Leu Lys Lys Leu Lys Lys Ala Leu
 1               5                  10                  15

Lys Lys Ala Leu
            20

<210> SEQ ID NO 69
<211> LENGTH: 23
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (23)
<223> OTHER INFORMATION: AMIDATION

<400> SEQUENCE: 69

Lys Ile Ala Lys Val Ala Leu Ala Lys Leu Gly Ile Gly Ala Val Leu
 1               5                  10                  15

Lys Val Leu Thr Thr Gly Leu
            20

<210> SEQ ID NO 70
<211> LENGTH: 12
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
```

```
<221> NAME/KEY: MOD_RES
<222> LOCATION: (12)
<223> OTHER INFORMATION: AMIDATION

<400> SEQUENCE: 70

Phe Ala Lys Lys Leu Ala Lys Leu Ala Lys Lys Leu
 1               5                  10

<210> SEQ ID NO 71
<211> LENGTH: 19
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (19)
<223> OTHER INFORMATION: AMIDATION

<400> SEQUENCE: 71

Met Pro Lys Glu Lys Val Phe Leu Lys Ile Glu Lys Met Gly Arg Asn
 1               5                  10                  15

Ile Arg Asn

<210> SEQ ID NO 72
<211> LENGTH: 26
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (26)
<223> OTHER INFORMATION: AMIDATION

<400> SEQUENCE: 72

Gly Ile Gly Ala Val Leu Lys Val Leu Thr Thr Gly Leu Pro Ala Leu
 1               5                  10                  15

Ile Ser Trp Ile Lys Arg Lys Arg Gln Gln
                 20                  25

<210> SEQ ID NO 73
<211> LENGTH: 16
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (16)
<223> OTHER INFORMATION: AMIDATION

<400> SEQUENCE: 73

Phe Ala Lys Lys Leu Ala Lys Leu Ala Lys Lys Leu Ala Lys Ala Leu
 1               5                  10                  15

<210> SEQ ID NO 74
<211> LENGTH: 12
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (12)
<223> OTHER INFORMATION: AMIDATION

<400> SEQUENCE: 74
```

```
Phe Ala Lys Lys Leu Leu Ala Lys Ala Leu Lys Leu
  1               5                  10
```

<210> SEQ ID NO 75
<211> LENGTH: 13
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (13)
<223> OTHER INFORMATION: AMIDATION

<400> SEQUENCE: 75

```
Phe Ala Lys Phe Leu Ala Lys Phe Leu Lys Lys Ala Leu
  1               5                  10
```

<210> SEQ ID NO 76
<211> LENGTH: 13
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (13)
<223> OTHER INFORMATION: AMIDATION

<400> SEQUENCE: 76

```
Phe Ala Lys Leu Leu Phe Lys Ala Leu Lys Lys Ala Leu
  1               5                  10
```

<210> SEQ ID NO 77
<211> LENGTH: 13
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (13)
<223> OTHER INFORMATION: AMIDATION

<400> SEQUENCE: 77

```
Phe Ala Lys Leu Leu Ala Lys Phe Leu Lys Lys Ala Leu
  1               5                  10
```

<210> SEQ ID NO 78
<211> LENGTH: 13
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (13)
<223> OTHER INFORMATION: AMIDATION

<400> SEQUENCE: 78

```
Phe Ala Lys Leu Leu Ala Lys Ala Phe Lys Lys Ala Leu
  1               5                  10
```

<210> SEQ ID NO 79
<211> LENGTH: 13
<212> TYPE: PRT
<213> ORGANISM: ARTIFICIAL SEQUENCE
<220> FEATURE:
<223> OTHER INFORMATION: SYNTHETIC SEQUENCE
<220> FEATURE:

```
<221> NAME/KEY: MOD_RES
<222> LOCATION: (13)
<223> OTHER INFORMATION: AMIDATION

<400> SEQUENCE: 79

Phe Ala Lys Leu Phe Ala Lys Ala Phe Lys Lys Ala Leu
 1               5                  10

<210> SEQ ID NO 80
<211> LENGTH: 13
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (13)
<223> OTHER INFORMATION: AMIDATION

<400> SEQUENCE: 80

Phe Ala Lys Leu Leu Ala Lys Ala Leu Lys Lys Phe Leu
 1               5                  10

<210> SEQ ID NO 81
<211> LENGTH: 14
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (14)
<223> OTHER INFORMATION: AMIDATION

<400> SEQUENCE: 81

Phe Ala Lys Leu Leu Ala Lys Ala Leu Lys Lys Phe Ala Leu
 1               5                  10

<210> SEQ ID NO 82
<211> LENGTH: 14
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (14)
<223> OTHER INFORMATION: AMIDATION

<400> SEQUENCE: 82

Phe Ala Lys Leu Leu Ala Lys Leu Ala Lys Lys Phe Ala Leu
 1               5                  10

<210> SEQ ID NO 83
<211> LENGTH: 14
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (14)
<223> OTHER INFORMATION: AMIDATION

<400> SEQUENCE: 83

Phe Ala Lys Leu Phe Ala Lys Leu Ala Lys Lys Phe Ala Leu
 1               5                  10

<210> SEQ ID NO 84
```

```
<211> LENGTH: 13
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (13)
<223> OTHER INFORMATION: AMIDATION

<400> SEQUENCE: 84

Phe Lys Leu Ala Phe Lys Leu Ala Lys Lys Ala Phe Leu
 1               5                  10

<210> SEQ ID NO 85
<211> LENGTH: 10
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (10)
<223> OTHER INFORMATION: AMIDATION

<400> SEQUENCE: 85

Phe Ala Lys Leu Leu Ala Lys Leu Ala Lys
 1               5                  10

<210> SEQ ID NO 86
<211> LENGTH: 13
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (13)
<223> OTHER INFORMATION: AMIDATION

<400> SEQUENCE: 86

Phe Ala Lys Leu Leu Ala Lys Leu Ala Lys Lys Val Leu
 1               5                  10

<210> SEQ ID NO 87
<211> LENGTH: 13
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (13)
<223> OTHER INFORMATION: AMIDATION

<400> SEQUENCE: 87

Phe Ala Lys Leu Leu Ala Lys Leu Ala Lys Lys Ile Leu
 1               5                  10

<210> SEQ ID NO 88
<211> LENGTH: 13
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (13)
<223> OTHER INFORMATION: AMIDATION

<400> SEQUENCE: 88
```

Phe Ala Lys Leu Leu Ala Lys Leu Ala Lys Lys Glu Leu
 1               5                  10

<210> SEQ ID NO 89
<211> LENGTH: 13
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (13)
<223> OTHER INFORMATION: AMIDATION

<400> SEQUENCE: 89

Phe Ala Lys Leu Leu Ala Lys Leu Ala Lys Lys Ser Leu
 1               5                  10

<210> SEQ ID NO 90
<211> LENGTH: 5
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (5)
<223> OTHER INFORMATION: AMIDATION

<400> SEQUENCE: 90

Phe Ala Lys Leu Ala
 1               5

<210> SEQ ID NO 91
<211> LENGTH: 5
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (5)
<223> OTHER INFORMATION: AMIDATION

<400> SEQUENCE: 91

Phe Ala Lys Leu Phe
 1               5

<210> SEQ ID NO 92
<211> LENGTH: 5
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (5)
<223> OTHER INFORMATION: AMIDATION

<400> SEQUENCE: 92

Lys Ala Lys Leu Phe
 1               5

<210> SEQ ID NO 93
<211> LENGTH: 5
<212> TYPE: PRT
<213> ORGANISM: ARTIFICIAL SEQUENCE
<220> FEATURE:
<223> OTHER INFORMATION: SYNTHETIC SEQUENCE

```
<220> FEATURE:
<221> NAME/KEY: MOD_RES
<222> LOCATION: (5)
<223> OTHER INFORMATION: AMIDATION

<400> SEQUENCE: 93

Lys Trp Lys Leu Phe
 1               5

<210> SEQ ID NO 94
<211> LENGTH: 13
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (13)
<223> OTHER INFORMATION: AMIDATION

<400> SEQUENCE: 94

Phe Gly Lys Gly Ile Gly Lys Val Gly Lys Lys Leu Leu
 1               5                  10

<210> SEQ ID NO 95
<211> LENGTH: 15
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (15)
<223> OTHER INFORMATION: AMIDATION

<400> SEQUENCE: 95

Phe Ala Phe Gly Lys Gly Ile Gly Lys Val Gly Lys Lys Leu Leu
 1               5                  10                  15

<210> SEQ ID NO 96
<211> LENGTH: 22
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (22)
<223> OTHER INFORMATION: AMIDATION

<400> SEQUENCE: 96

Phe Ala Lys Ala Ile Ala Lys Ile Ala Phe Gly Lys Gly Ile Gly Lys
 1               5                  10                  15

Val Gly Lys Lys Leu Leu
                 20

<210> SEQ ID NO 97
<211> LENGTH: 22
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (22)
<223> OTHER INFORMATION: AMIDATION

<400> SEQUENCE: 97

Phe Ala Lys Leu Trp Ala Lys Leu Ala Phe Gly Lys Gly Ile Gly Lys
```

```
                1               5              10              15
Val Gly Lys Lys Leu Leu
            20

<210> SEQ ID NO 98
<211> LENGTH: 12
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (12)
<223> OTHER INFORMATION: AMIDATION

<400> SEQUENCE: 98

Phe Ala Lys Leu Trp Ala Lys Leu Ala Lys Lys Leu
  1               5                  10

<210> SEQ ID NO 99
<211> LENGTH: 13
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (13)
<223> OTHER INFORMATION: AMIDATION

<400> SEQUENCE: 99

Phe Ala Lys Gly Val Gly Lys Val Gly Lys Lys Ala Leu
  1               5                  10

<210> SEQ ID NO 100
<211> LENGTH: 15
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (15)
<223> OTHER INFORMATION: AMIDATION

<400> SEQUENCE: 100

Phe Ala Phe Gly Lys Gly Ile Gly Lys Ile Gly Lys Lys Gly Leu
  1               5                  10                  15

<210> SEQ ID NO 101
<211> LENGTH: 16
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (16)
<223> OTHER INFORMATION: AMIDATION

<400> SEQUENCE: 101

Phe Ala Lys Ile Ile Ala Lys Ile Ala Lys Ile Ala Lys Lys Ile Leu
  1               5                  10                  15

<210> SEQ ID NO 102
<211> LENGTH: 15
<212> TYPE: PRT
<213> ORGANISM: ARTIFICIAL SEQUENCE
<220> FEATURE:
```

```
<223> OTHER INFORMATION: SYNTHETIC SEQUENCE
<220> FEATURE:
<221> NAME/KEY: MOD_RES
<222> LOCATION: (15)
<223> OTHER INFORMATION: AMIDATION

<400> SEQUENCE: 102

Phe Ala Phe Ala Lys Ile Ile Ala Lys Ile Ala Lys Lys Ile Ile
 1               5                  10                  15

<210> SEQ ID NO 103
<211> LENGTH: 7
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (7)
<223> OTHER INFORMATION: AMIDATION

<400> SEQUENCE: 103

Phe Ala Leu Ala Leu Lys Ala
 1               5

<210> SEQ ID NO 104
<211> LENGTH: 12
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (12)
<223> OTHER INFORMATION: AMIDATION

<400> SEQUENCE: 104

Lys Trp Lys Leu Ala Lys Lys Ala Leu Ala Leu Leu
 1               5                  10

<210> SEQ ID NO 105
<211> LENGTH: 12
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (12)
<223> OTHER INFORMATION: AMIDATION

<400> SEQUENCE: 105

Phe Ala Lys Ile Ile Ala Lys Ile Ala Lys Lys Ile
 1               5                  10

<210> SEQ ID NO 106
<211> LENGTH: 12
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (12)
<223> OTHER INFORMATION: AMIDATION

<400> SEQUENCE: 106

Phe Ala Leu Ala Leu Lys Ala Leu Lys Lys Ala Leu
 1               5                  10
```

```
<210> SEQ ID NO 107
<211> LENGTH: 8
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (8)
<223> OTHER INFORMATION: AMIDATION

<400> SEQUENCE: 107

Phe Ala Leu Lys Ala Leu Lys Lys
 1               5

<210> SEQ ID NO 108
<211> LENGTH: 13
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (13)
<223> OTHER INFORMATION: AMIDATION

<400> SEQUENCE: 108

Lys Tyr Lys Lys Ala Leu Lys Lys Leu Ala Lys Leu Leu
 1               5                  10

<210> SEQ ID NO 109
<211> LENGTH: 17
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (17)
<223> OTHER INFORMATION: AMIDATION

<400> SEQUENCE: 109

Phe Lys Arg Leu Ala Lys Ile Lys Val Leu Arg Leu Ala Lys Ile Lys
 1               5                  10                  15

Arg

<210> SEQ ID NO 110
<211> LENGTH: 13
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (13)
<223> OTHER INFORMATION: AMIDATION

<400> SEQUENCE: 110

Phe Ala Lys Leu Ala Lys Lys Ala Leu Ala Lys Leu Leu
 1               5                  10

<210> SEQ ID NO 111
<211> LENGTH: 13
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
```

<222> LOCATION: (13)
<223> OTHER INFORMATION: AMIDATION
<220> FEATURE:
<221> NAME/KEY: MOD_RES
<222> LOCATION: (13)
<223> OTHER INFORMATION: AMIDATION

<400> SEQUENCE: 111

Lys Ala Lys Leu Ala Lys Lys Ala Leu Ala Lys Leu Leu
1               5                   10

<210> SEQ ID NO 112
<211> LENGTH: 17
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (17)
<223> OTHER INFORMATION: AMIDATION

<400> SEQUENCE: 112

Lys Leu Ala Leu Lys Leu Ala Leu Lys Ala Leu Lys Ala Ala Lys Leu
1               5                   10                  15

Ala

<210> SEQ ID NO 113
<211> LENGTH: 11
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (11)
<223> OTHER INFORMATION: AMIDATION

<400> SEQUENCE: 113

Phe Ala Lys Leu Leu Ala Lys Leu Ala Lys Lys
1               5                   10

<210> SEQ ID NO 114
<211> LENGTH: 13
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (13)
<223> OTHER INFORMATION: AMIDATION

<400> SEQUENCE: 114

Phe Ala Lys Leu Leu Ala Lys Leu Ala Lys Lys Gly Leu
1               5                   10

<210> SEQ ID NO 115
<211> LENGTH: 17
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (17)
<223> OTHER INFORMATION: AMIDATION

<400> SEQUENCE: 115

```
Phe Ala Leu Lys Ala Leu Lys Lys Leu Lys Ala Leu Lys Lys Ala
1               5                   10                  15
Leu
```

<210> SEQ ID NO 116
<211> LENGTH: 13
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (13)
<223> OTHER INFORMATION: AMIDATION

<400> SEQUENCE: 116

```
Val Ala Lys Leu Leu Ala Lys Leu Ala Lys Lys Val Leu
1               5                   10
```

<210> SEQ ID NO 117
<211> LENGTH: 13
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (13)
<223> OTHER INFORMATION: AMIDATION

<400> SEQUENCE: 117

```
Tyr Ala Lys Leu Leu Ala Lys Leu Ala Lys Lys Ala Leu
1               5                   10
```

<210> SEQ ID NO 118
<211> LENGTH: 17
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (17)
<223> OTHER INFORMATION: AMIDATION

<400> SEQUENCE: 118

```
Lys Leu Leu Lys Leu Leu Leu Lys Leu Tyr Lys Lys Leu Leu Lys Leu
1               5                   10                  15
Leu
```

<210> SEQ ID NO 119
<211> LENGTH: 26
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (26)
<223> OTHER INFORMATION: AMIDATION

<400> SEQUENCE: 119

```
Phe Ala Val Gly Leu Arg Ala Ile Lys Arg Ala Leu Lys Lys Leu Arg
1               5                   10                  15
Arg Gly Val Arg Lys Val Ala Lys Asp Leu
                20                  25
```

```
<210> SEQ ID NO 120
<211> LENGTH: 16
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (16)
<223> OTHER INFORMATION: AMIDATION

<400> SEQUENCE: 120

Lys Leu Ala Lys Lys Leu Ala Lys Leu Ala Lys Leu Ala Lys Ala Leu
 1               5                  10                  15

<210> SEQ ID NO 121
<211> LENGTH: 16
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 121

Lys Leu Ala Lys Lys Leu Ala Lys Leu Ala Lys Leu Ala Lys Ala Leu
 1               5                  10                  15

<210> SEQ ID NO 122
<211> LENGTH: 9
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (9)
<223> OTHER INFORMATION: AMIDATION

<400> SEQUENCE: 122

Lys Trp Lys Lys Leu Ala Lys Lys Trp
 1               5

<210> SEQ ID NO 123
<211> LENGTH: 9
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 123

Lys Trp Lys Lys Leu Ala Lys Lys Trp
 1               5

<210> SEQ ID NO 124
<211> LENGTH: 17
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (17)
<223> OTHER INFORMATION: AMIDATION

<400> SEQUENCE: 124

Lys Leu Trp Lys Lys Trp Ala Lys Lys Trp Leu Lys Leu Trp Lys Ala
 1               5                  10                  15

Trp
```

```
<210> SEQ ID NO 125
<211> LENGTH: 16
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 125

Lys Leu Trp Lys Lys Trp Ala Lys Lys Trp Leu Lys Leu Trp Lys Ala
 1               5                  10                  15

<210> SEQ ID NO 126
<211> LENGTH: 11
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (11)
<223> OTHER INFORMATION: AMIDATION

<400> SEQUENCE: 126

Phe Ala Leu Ala Leu Lys Ala Leu Lys Lys Leu
 1               5                  10

<210> SEQ ID NO 127
<211> LENGTH: 11
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (11)
<223> OTHER INFORMATION: AMIDATION

<400> SEQUENCE: 127

Phe Ala Leu Ala Lys Ala Leu Lys Lys Ala Leu
 1               5                  10

<210> SEQ ID NO 128
<211> LENGTH: 12
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (12)
<223> OTHER INFORMATION: AMIDATION

<400> SEQUENCE: 128

Phe Ala Leu Ala Leu Lys Leu Ala Lys Lys Ala Leu
 1               5                  10

<210> SEQ ID NO 129
<211> LENGTH: 6
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (6)
<223> OTHER INFORMATION: AMIDATION

<400> SEQUENCE: 129

Phe Ala Leu Leu Lys Leu
 1               5
```

```
<210> SEQ ID NO 130
<211> LENGTH: 10
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (10)
<223> OTHER INFORMATION: AMIDATION

<400> SEQUENCE: 130

Phe Ala Leu Ala Leu Lys Ala Leu Lys Lys
 1               5                  10

<210> SEQ ID NO 131
<211> LENGTH: 10
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (10)
<223> OTHER INFORMATION: AMIDATION

<400> SEQUENCE: 131

Phe Ala Leu Lys Ala Leu Lys Lys Ala Leu
 1               5                  10

<210> SEQ ID NO 132
<211> LENGTH: 11
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (11)
<223> OTHER INFORMATION: AMIDATION

<400> SEQUENCE: 132

Phe Ala Leu Leu Lys Ala Leu Lys Lys Ala Leu
 1               5                  10

<210> SEQ ID NO 133
<211> LENGTH: 4
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (4)
<223> OTHER INFORMATION: AMIDATION

<400> SEQUENCE: 133

Lys Trp Lys Lys
 1

<210> SEQ ID NO 134
<211> LENGTH: 5
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (5)
```

```
<223> OTHER INFORMATION: AMIDATION

<400> SEQUENCE: 134

Lys Trp Lys Lys Leu
 1               5

<210> SEQ ID NO 135
<211> LENGTH: 9
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (9)
<223> OTHER INFORMATION: AMIDATION

<400> SEQUENCE: 135

Lys Phe Lys Lys Leu Ala Lys Lys Phe
 1               5

<210> SEQ ID NO 136
<211> LENGTH: 9
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (9)
<223> OTHER INFORMATION: AMIDATION

<400> SEQUENCE: 136

Lys Phe Lys Lys Leu Ala Lys Lys Trp
 1               5

<210> SEQ ID NO 137
<211> LENGTH: 11
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (11)
<223> OTHER INFORMATION: AMIDATION

<400> SEQUENCE: 137

Phe Ala Leu Ala Leu Lys Ala Leu Lys Lys Ala
 1               5                  10

<210> SEQ ID NO 138
<211> LENGTH: 12
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (12)
<223> OTHER INFORMATION: AMIDATION

<400> SEQUENCE: 138

Phe Ala Leu Leu Lys Ala Leu Leu Lys Lys Ala Leu
 1               5                  10

<210> SEQ ID NO 139
<211> LENGTH: 11
<212> TYPE: PRT
```

```
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (11)
<223> OTHER INFORMATION: AMIDATION

<400> SEQUENCE: 139

Phe Ala Leu Ala Leu Lys Leu Ala Lys Lys Leu
 1               5                  10

<210> SEQ ID NO 140
<211> LENGTH: 11
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (11)
<223> OTHER INFORMATION: AMIDATION

<400> SEQUENCE: 140

Leu Lys Lys Leu Ala Lys Leu Ala Leu Ala Phe
 1               5                  10

<210> SEQ ID NO 141
<211> LENGTH: 11
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (11)
<223> OTHER INFORMATION: AMIDATION

<400> SEQUENCE: 141

Val Ala Leu Ala Leu Lys Ala Leu Lys Lys Leu
 1               5                  10

<210> SEQ ID NO 142
<211> LENGTH: 10
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (10)
<223> OTHER INFORMATION: AMIDATION

<400> SEQUENCE: 142

Phe Ala Leu Ala Leu Lys Leu Lys Lys Leu
 1               5                  10

<210> SEQ ID NO 143
<211> LENGTH: 10
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (10)
<223> OTHER INFORMATION: AMIDATION

<400> SEQUENCE: 143

Phe Ala Leu Ala Leu Lys Ala Lys Lys Leu
```

```
                1               5                   10
```

<210> SEQ ID NO 144
<211> LENGTH: 4
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (4)
<223> OTHER INFORMATION: AMIDATION

<400> SEQUENCE: 144

```
Phe Ala Leu Ala
  1
```

<210> SEQ ID NO 145
<211> LENGTH: 5
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (5)
<223> OTHER INFORMATION: AMIDATION

<400> SEQUENCE: 145

```
Trp Ala Leu Ala Leu
  1               5
```

<210> SEQ ID NO 146
<211> LENGTH: 23
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (23)
<223> OTHER INFORMATION: AMIDATION

<400> SEQUENCE: 146

```
Gly Ile Gly Lys Phe Leu His Ala Ala Lys Lys Phe Ala Lys Ala Phe
  1               5                  10                  15

Val Ala Glu Ile Met Asn Ser
             20
```

<210> SEQ ID NO 147
<211> LENGTH: 23
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (23)
<223> OTHER INFORMATION: AMIDATION

<400> SEQUENCE: 147

```
Phe Ala Lys Lys Phe Ala Lys Lys Phe Lys Lys Phe Ala Lys Lys Phe
  1               5                  10                  15

Ala Lys Phe Ala Phe Ala Phe
             20
```

<210> SEQ ID NO 148
<211> LENGTH: 10

```
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (10)
<223> OTHER INFORMATION: AMIDATION

<400> SEQUENCE: 148

Lys Lys Val Val Phe Lys Val Lys Phe Lys
 1               5                  10

<210> SEQ ID NO 149
<211> LENGTH: 10
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (10)
<223> OTHER INFORMATION: AMIDATION

<400> SEQUENCE: 149

Phe Lys Val Lys Phe Lys Val Lys Val Lys
 1               5                  10

<210> SEQ ID NO 150
<211> LENGTH: 38
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (38)
<223> OTHER INFORMATION: AMIDATION

<400> SEQUENCE: 150

Leu Pro Lys Trp Lys Val Phe Lys Lys Ile Glu Lys Val Gly Arg Asn
 1               5                  10                  15

Ile Arg Asn Gly Ile Val Lys Ala Gly Pro Ala Ile Ala Val Leu Gly
                20                  25                  30

Glu Ala Lys Ala Leu Gly
            35

<210> SEQ ID NO 151
<211> LENGTH: 23
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (23)
<223> OTHER INFORMATION: AMIDATION

<400> SEQUENCE: 151

Phe Ala Lys Lys Leu Ala Lys Lys Leu Lys Lys Leu Ala Lys Lys Leu
 1               5                  10                  15

Ala Lys Leu Ala Lys Lys Leu
                20

<210> SEQ ID NO 152
<211> LENGTH: 15
<212> TYPE: PRT
<213> ORGANISM: ARTIFICIAL SEQUENCE
```

```
<220> FEATURE:
<223> OTHER INFORMATION: SYNTHETIC SEQUENCE
<220> FEATURE:
<221> NAME/KEY: MOD_RES
<222> LOCATION: (15)
<223> OTHER INFORMATION: AMIDATION

<400> SEQUENCE: 152

Val Ala Lys Ala Leu Lys Ala Leu Leu Lys Ala Leu Lys Ala Leu
 1               5                  10                  15

<210> SEQ ID NO 153
<211> LENGTH: 13
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (13)
<223> OTHER INFORMATION: AMIDATION

<400> SEQUENCE: 153

Val Ala Lys Phe Leu Ala Lys Phe Leu Lys Lys Ala Leu
 1               5                  10

<210> SEQ ID NO 154
<211> LENGTH: 23
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (23)
<223> OTHER INFORMATION: AMIDATION

<400> SEQUENCE: 154

Val Ala Lys Lys Phe Ala Lys Lys Phe Lys Lys Phe Ala Lys Lys Phe
 1               5                  10                  15

Ala Lys Phe Ala Phe Ala Phe
            20

<210> SEQ ID NO 155
<211> LENGTH: 19
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (19)
<223> OTHER INFORMATION: AMIDATION

<400> SEQUENCE: 155

Val Ala Lys Lys Leu Ala Lys Leu Ala Lys Lys Leu Ala Lys Leu Ala
 1               5                  10                  15

Leu Ala Leu

<210> SEQ ID NO 156
<211> LENGTH: 15
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (15)
<223> OTHER INFORMATION: AMIDATION
```

```
<400> SEQUENCE: 156

Val Ala Lys Lys Leu Ala Lys Leu Ala Lys Lys Leu Leu Ala Leu
 1               5                  10                  15

<210> SEQ ID NO 157
<211> LENGTH: 13
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (13)
<223> OTHER INFORMATION: AMIDATION

<400> SEQUENCE: 157

Val Ala Lys Leu Leu Ala Lys Ala Leu Lys Lys Leu Leu
 1               5                  10

<210> SEQ ID NO 158
<211> LENGTH: 23
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (23)
<223> OTHER INFORMATION: AMIDATION

<400> SEQUENCE: 158

Val Ala Leu Ala Leu Lys Ala Leu Lys Lys Ala Leu Lys Lys Leu Lys
 1               5                  10                  15

Lys Ala Leu Lys Lys Ala Leu
                 20

<210> SEQ ID NO 159
<211> LENGTH: 23
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 159

Val Ala Leu Ala Leu Lys Ala Leu Lys Lys Ala Leu Lys Lys Leu Lys
 1               5                  10                  15

Lys Ala Leu Lys Lys Ala Leu
                 20

<210> SEQ ID NO 160
<211> LENGTH: 23
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (23)
<223> OTHER INFORMATION: AMIDATION

<400> SEQUENCE: 160

Val Ala Leu Ala Leu Lys Ala Leu Lys Lys Ala Leu Lys Lys Leu Lys
 1               5                  10                  15

Lys Leu Ala Lys Lys Ala Leu
                 20
```

<210> SEQ ID NO 161
<211> LENGTH: 23
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (23)
<223> OTHER INFORMATION: AMIDATION

<400> SEQUENCE: 161

Val Ala Leu Ala Leu Lys Ala Leu Lys Lys Leu Leu Lys Lys Leu Lys
 1               5                  10                  15

Lys Leu Ala Lys Lys Ala Leu
            20

<210> SEQ ID NO 162
<211> LENGTH: 23
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 162

Phe Ala Lys Lys Leu Ala Lys Lys Leu Lys Lys Leu Ala Lys Lys Leu
 1               5                  10                  15

Ala Lys Leu Ala Leu Ala Leu
            20

<210> SEQ ID NO 163
<211> LENGTH: 30
<212> TYPE: PRT
<213> ORGANISM: ARTIFICIAL SEQUENCE
<220> FEATURE:
<223> OTHER INFORMATION: SYNTHETIC SEQUENCE

<400> SEQUENCE: 163

Phe Ala Lys Lys Leu Ala Lys Lys Leu Lys Lys Leu Ala Lys Lys Leu
 1               5                  10                  15

Ala Lys Leu Ala Leu Ala Leu Lys Ala Leu Ala Leu Lys Ala
            20                  25                  30

<210> SEQ ID NO 164
<211> LENGTH: 18
<212> TYPE: PRT
<213> ORGANISM: ARTIFICIAL SEQUENCE
<220> FEATURE:
<223> OTHER INFORMATION: SYNTHETIC SEQUENCE
<220> FEATURE:
<221> NAME/KEY: MOD_RES
<222> LOCATION: (18)
<223> OTHER INFORMATION: AMIDATION

<400> SEQUENCE: 164

Phe Ala Lys Lys Leu Ala Lys Lys Leu Lys Lys Leu Ala Lys Lys Leu
 1               5                  10                  15

Ala Lys

<210> SEQ ID NO 165
<211> LENGTH: 13
<212> TYPE: PRT
<213> ORGANISM: ARTIFICIAL SEQUENCE
<220> FEATURE:
<223> OTHER INFORMATION: SYNTHETIC SEQUENCE
<220> FEATURE:

-continued

```
<221> NAME/KEY: MOD_RES
<222> LOCATION: (13)
<223> OTHER INFORMATION: AMIDATION

<400> SEQUENCE: 165

Phe Ala Lys Leu Leu Ala Leu Ala Leu Lys Lys Ala Leu
 1               5                  10
```